(12) United States Patent
Crump et al.

(10) Patent No.: US 10,494,415 B2
(45) Date of Patent: Dec. 3, 2019

(54) INSULIN-LIKE GROWTH FACTOR 2 (IGF2) BINDING AGENTS

(71) Applicant: Cancer Research Technology Limited, London (GB)

(72) Inventors: Matthew Philip Crump, Bristol (GB); Andrew Bassim Hassan, Chesterton (GB)

(73) Assignee: Oxford University Innovation, Oxford (GB)

( * ) Notice: Subject to any disclaimer, the term of this patent is extended or adjusted under 35 U.S.C. 154(b) by 0 days.

(21) Appl. No.: 15/752,320

(22) PCT Filed: Aug. 8, 2016

(86) PCT No.: PCT/EP2016/068904
§ 371 (c)(1),
(2) Date: Feb. 13, 2018

(87) PCT Pub. No.: WO2017/029148
PCT Pub. Date: Feb. 23, 2017

(65) Prior Publication Data
US 2018/0237497 A1 Aug. 23, 2018

(30) Foreign Application Priority Data

Aug. 14, 2015 (GB) .................................. 1514531.1
Apr. 5, 2016 (GB) .................................. 1605820.8

(51) Int. Cl.
| | |
|---|---|
| *C07K 14/435* | (2006.01) |
| *A61K 38/00* | (2006.01) |
| *C07K 14/71* | (2006.01) |
| *A61P 35/00* | (2006.01) |
| *A61K 31/5377* | (2006.01) |
| *A61K 38/17* | (2006.01) |

(52) U.S. Cl.
CPC .......... *C07K 14/71* (2013.01); *A61K 31/5377* (2013.01); *A61K 38/179* (2013.01); *A61P 35/00* (2018.01); *C07K 14/435* (2013.01); *A61K 38/00* (2013.01); *C07K 2319/00* (2013.01); *C07K 2319/20* (2013.01); *C07K 2319/30* (2013.01)

(58) Field of Classification Search
None
See application file for complete search history.

(56) References Cited

U.S. PATENT DOCUMENTS 8,293,875 B2 * 10/2012 Hassan ................. C07K 14/71
435/320.1

FOREIGN PATENT DOCUMENTS

| WO | WO 2007/020402 A1 | 2/2007 |
|---|---|---|
| WO | WO 2013/013017 A2 | 1/2013 |

OTHER PUBLICATIONS

Sivaramakrishna et al., International Journal of Biological Macromolecules 44 (2009) 435-440.*
UniProt UPI0001C5F204. Nov. 16, 2011.
Moschos et al., The role of the IGF system in cancer: from basic to clinical studies and clinical applications. Oncology. 2002;63(4):317-32.

* cited by examiner

*Primary Examiner* — Marianne P Allen
(74) *Attorney, Agent, or Firm* — Wolf, Greenfield & Sacks, P.C.

(57) ABSTRACT

This invention relates to mutant polypeptides comprising the IGF2 binding domain of the Insulin-like Growth Factor 2 Receptor (IGF2R) with residue P1597 is substituted for a different residue, for example H or K. Other residues which may be mutated include S1543, E1544, K1545, G1546, L1547, Q1569, S1602, G1603 and/or K1631. These IGF2 binding domains display dramatically increased binding affinity for IGF2 compared to both the wild-type and previously identified mutants and may be useful for example in cancer therapy.

10 Claims, 19 Drawing Sheets

Specification includes a Sequence Listing.

INSULIN-LIKE GROWTH FACTOR 2 (IGF2) BINDING AGENTS

RELATED APPLICATION

This application is a national stage filing under 35 U.S.C. § 371 of international application number PCT/EP2016/068904, filed Aug. 8, 2016, the contents of which is incorporated by reference herein in its entirety.

FIELD

This invention relates to binding agents for use in the sequestration of Insulin-like Growth Factor 2 (IGF2), for example, in the treatment of cancer.

BACKGROUND

Insulin-like Growth Factor 2 (IGF2) is a small mitogenic peptide hormone that functions principally during embryonic growth, where its activity is tightly regulated, but is also frequently deregulated in tumours, which predominantly express IGF2 rather than IGF1. Like IGF1, IGF2 exerts its mitogenic affect predominantly by signalling through the IGF1 receptor (IGF1R), but also unlike IGF1 through isoform A of the Insulin receptor, both leading to tyrosine kinase activation and stimulation of both the mitogen-activated protein (MAP) kinase and PKB/AKT signalling.

Many therapies targeting IGF1R have failed in the clinic. This failure may be due to redundancy, as IGF2 still functions through the Insulin receptor. Furthermore, inhibition of IGF1 signalling causes a feedback loop via the pituitary gland, which produces more growth hormone, which in turn tells the liver to produce more IGF1 [1]. Inhibition of IGF2 signalling does not cause such a feedback loop and preferential targeting of IGF2 over IGF1 may reduce negative feedback effects.

The genes Igf2 and Igf2r are imprinted in mammals, and code for the ligand and cell growth promoter, insulin-like growth factor 2 (IGF2) and the mannose 6-phosphate/IGF2 receptor (M6P/IGF2R or IGF2R), respectively [2, 3]. As imprinted genes, both genes are mono-allelically expressed.

Unlike products of other mammalian imprinted genes, IGF2 and M6P/IGF2R are unusual because they specifically bind with high affinity[4-10]. IGF2 binding is specific for domain 11 of the 15 extra-cellular domains of IGF2R. Membrane bound IGF2R acts to negatively regulate free IGF2 levels by receptor internalisation and intra-cellular degradation of IGF2 [2].

Loss of function of Igf2r through disruption of the maternal allele results in Igf2 dependent overgrowth and fatality [11-15]. Loss of function of IGF2R and gain of function of IGF2 through somatic mutation and increased expression, respectively, are also frequently observed in human cancer [16-20]. Conversely, titration of IGF2 via gain of function of Igf2r, for example by bi-allelic expression, leads to an Igf2 dependent growth reduction [21]. The effects of Igf2r on Igf2 dependent growth are thus modified by two fold changes in allelic dosage, suggesting also that the normal capacity of IGF2R to reduce IGF2 bioavailability depends on the affinity of domain 11 for IGF2.

Wild-type IGF2R domain 11 is selective for IGF2 over IGF1 because of a key specific interaction with threonine 19 of IGF2. The IGF2 binding site within domain 11 of human IGF2R consists of a hydrophobic pocket centred on the CD loop, surrounded by polar and charged residues in the AB, FG and HI loops that complement surface charge on IGF2 [3]. The exception to this is an otherwise unfavourable charge-charge interaction between E1544 on the AB loop and D23 on IGF2 [6, 22, 23]. Domain 13 interacts with the AB loop of domain 11, breaking this interaction in the full length receptor and thus contributes to the stability of the complex by decreasing the 'off-rate' ($k_{off}$) of the IGF2 interaction compared to domain 11 alone [22]. Mutations in this structurally sensitive AB loop have, however, resulted in isolated domain 11 analogues with increased affinity for IGF2 (e.g. domain $11^{E1544K, K1545S, L1547V}$ or clone AB3, $K_D$=15 nM) [3, 23],[57]. The higher affinity domain $11^{AB3}$ AB loop mutant also led to the solution structure of a stable 24.2 kDa complex (IGF2: domain $11^{AB3}$)[3]. Domain $11^{AB3}$ retains a relatively fixed conformation of the CD loop upon complex formation, and the mutated AB loop moves to accommodate IGF2 helix 1 and the packing of IGF2 residues T16 and F19. The FG loop also repositions between helices 2 and 3 of IGF2 to accommodate burial of IGF2 residue L53 in the domain $11^{AB3}$ binding site. All three of these IGF2 residues are critical for IGF2R binding [22, 24]. Both conformational changes also allow the formation of complementary hydrophobic surfaces and support a range of H-bonding and salt bridging interactions with amino acids in the other loops[3].

Importantly, IGF2 binding to domain 11 co-evolved with the evolution of mammals, as in primitive mammals (monotremes) IGF2 binds with ten-fold lower affinity ($K_D$=250-400 μM vs domain $11^{WT}$ $K_D$=40-60 nM) [3-5, 10]. The structural evolution of domain 11 suggests that the IGF2 binding site has fully evolved in mammals[3].

SUMMARY

The present inventors have unexpectedly identified combinations of mutations in the IGF2 binding domain of the Insulin-like Growth Factor 2 Receptor (IGF2R) which dramatically increase the binding affinity for IGF2 compared to both the wild-type and previously identified mutants.

One aspect of the invention provides a mutant IGF2 binding domain comprising the amino acid sequence of residues 1511 to 1650 of human IGF2R with 30 or fewer, 20 or fewer, 15 or fewer or 10 or fewer of said residues mutated, wherein residue P1597 of said amino acid sequence is substituted for a different residue.

Another aspect of the invention provides a mutant IGF2 binding domain comprising an amino acid sequence which has at least 80% sequence identity, at least 90% sequence identity or at least 95% sequence identity with residues 1511 to 1650 of human IGF2R, wherein residue P1597 of said amino acid sequence is substituted for a different residue.

Another aspect of the invention provides a mutant IGF2 binding domain consisting of the amino acid sequence of residues 1511 to 1650 of human IGF2R with residue P1597 and at least five residues selected from S1543, E1544, K1545, G1546, L1547, Q1569, S1602, G1603 and K1631 substituted for different residues.

Another aspect of the invention provides a mutant IGF2 binding domain consisting of the amino acid sequence of residues 1511 to 1650 of human IGF2R with one of the following sets of substitutions;
1) S1543A, E1544K, K1545G, G1546W, L1547G, Q1569R, P1597H and S1602H
2) S1543A, E1544K, K1545G, G1546W, L1547G, Q1569R, P1597K and S1602H
3) S1543A, E1544K, K1545G, G1546W, L1547G, Q1569R, P1597H and G1603K 4) S1543A, E1544K, K1545G, G1546W, L1547G, Q1569R, P1597K and G1603K
5) E1544K, K1545S, L1547V, Q1569R, P1597H, and S1602H
6) E1544K, K1545S, L1547V, Q1569R, P1597K, and S1602H
7) E1544K, K1545S, L1547V, Q1569R, P1597H, S1602H, and G1603K
8) E1544K, K1545S, L1547V, Q1569R, P1597K, S1602H, and G1603K.

Other aspects of the invention provide polypeptides comprising mutant IGF2 binding domains described herein, nucleic acids encoding mutant IGF2 binding domains described herein and methods and uses of such domains, polypeptides and nucleic acids in therapy, for example in the treatment of cancer.

BRIEF DESCRIPTION OF FIGURES

(FIG. 12A-12B) IGF2-TRAP reduces IGF2 dependent xenograft growth (SKNMC-IGF2$^{1-67}$). 5×10$^6$ per injection site in CD-1 nude mice, single infused concentration of IGF2-TRAP (40 mg kg-1 per week) (green, n=10) or PBS control (blue, n=7, n=2 injection error, n=1 unexplained death). (p=0.002, Wilcoxon test across all time points). (FIG. 12C) IGF2-TRAP resulted in reduced levels of serum IGF2 independent of IGF1, Growth Hormone (GH) or IGFBP levels (Day 28, control PBS n=10 out of 10, IGF2-TRAP n=6 out of 7).

DETAILED DESCRIPTION

Figure 1:
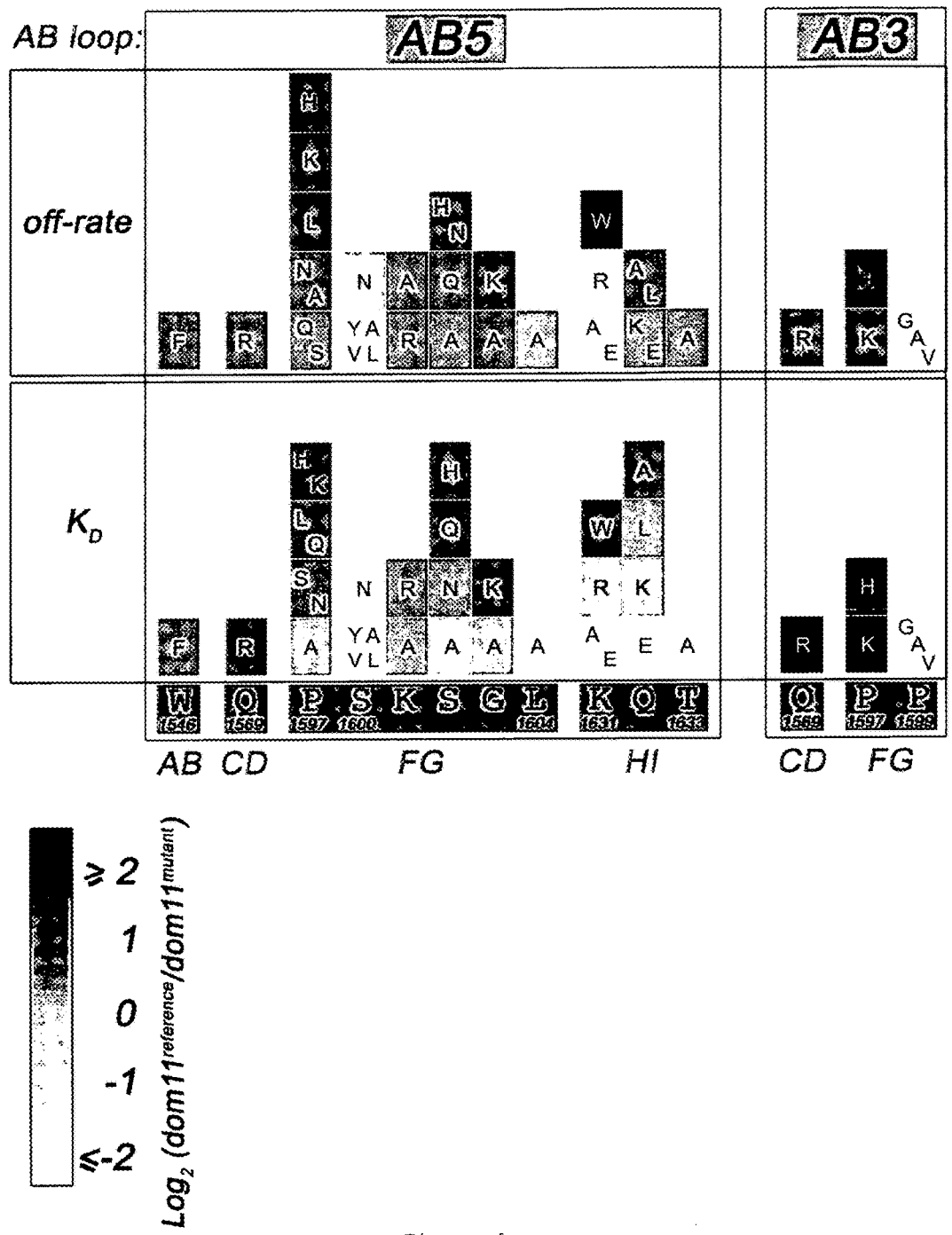
FIG. 1 shows a heat map of $IGF2^{1-67}$ binding to single point mutants in loops of domain $11^{AB5}$ (left) and domain $11^{AB3}$ (right) relative to their respective AB loop background. Top panel, effect on the $k_{off}$. Bottom panel, effect on the $K_D$. The scale represents the $\log_2$ of the domain $11^{reference}$/domain $11^{mutant}$ parameter ratio, where domain $11^{reference}$ is dom (FIG. 11A) IGF2-TRAP decreases the cell viability of IGF2-autocrine SKNMC-IGF2$^{1-67}$ cell line compared to luciferase only SKNMC control.
Figure 2:
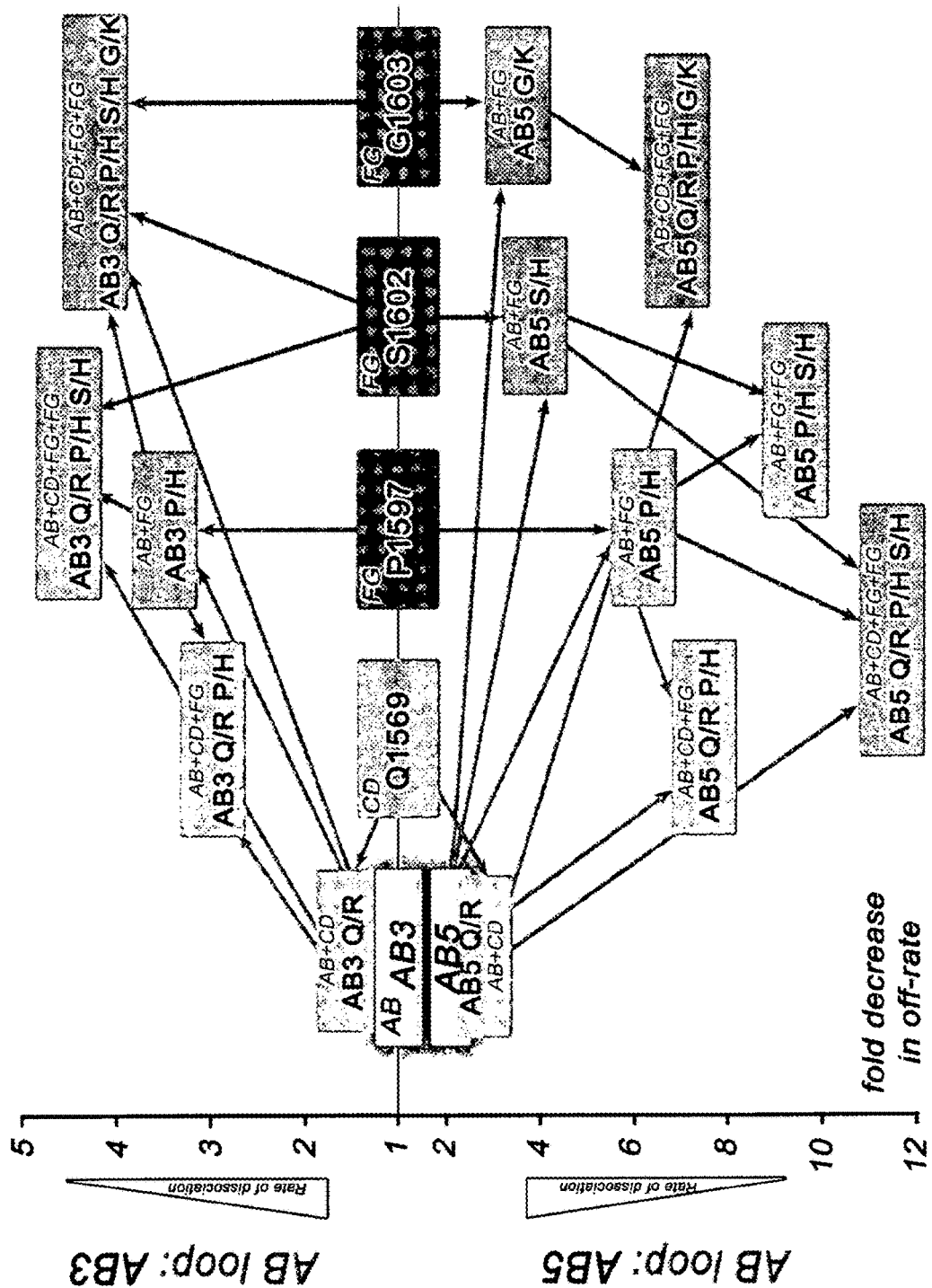
Figure 3:
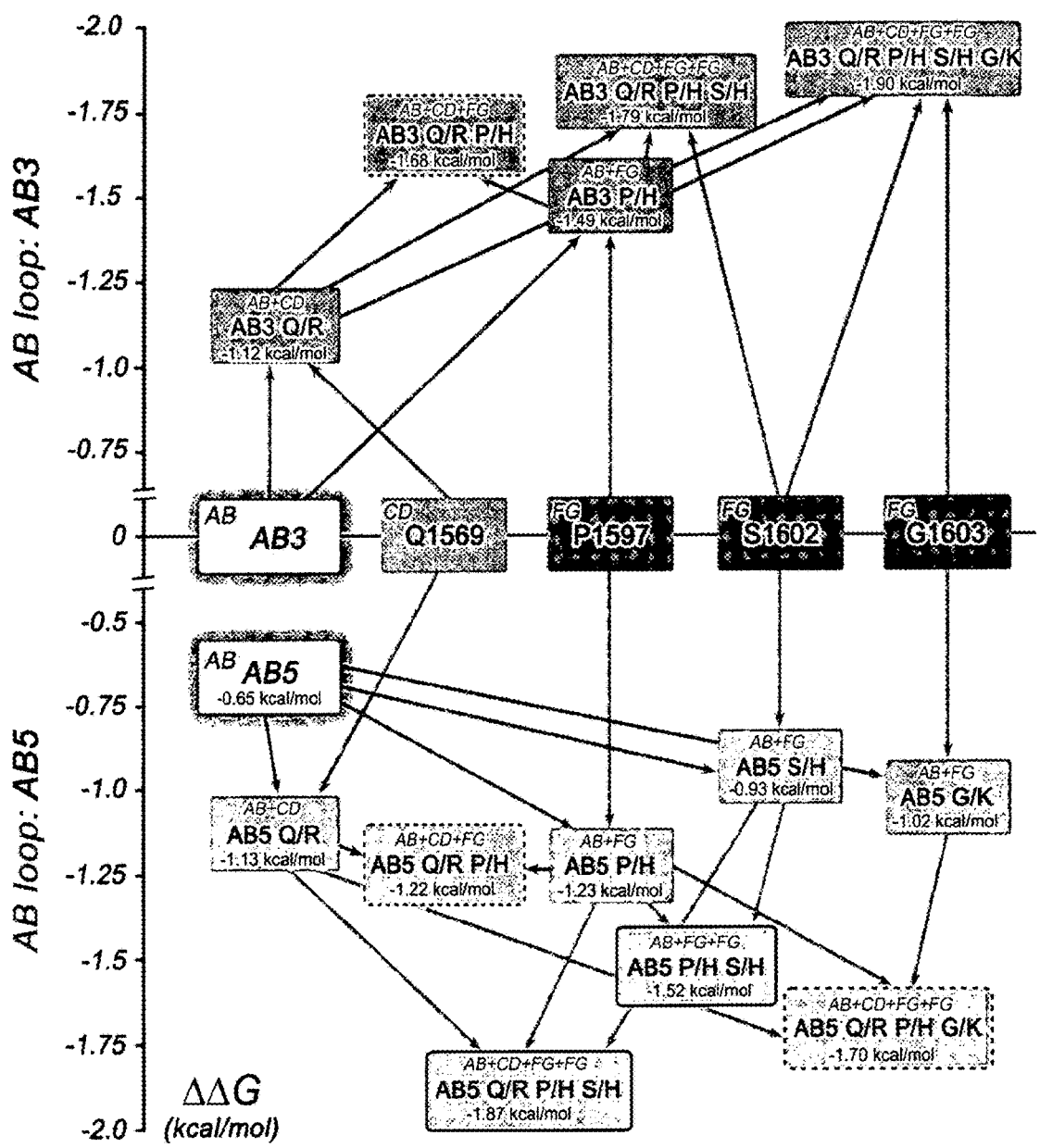
Figure 4:
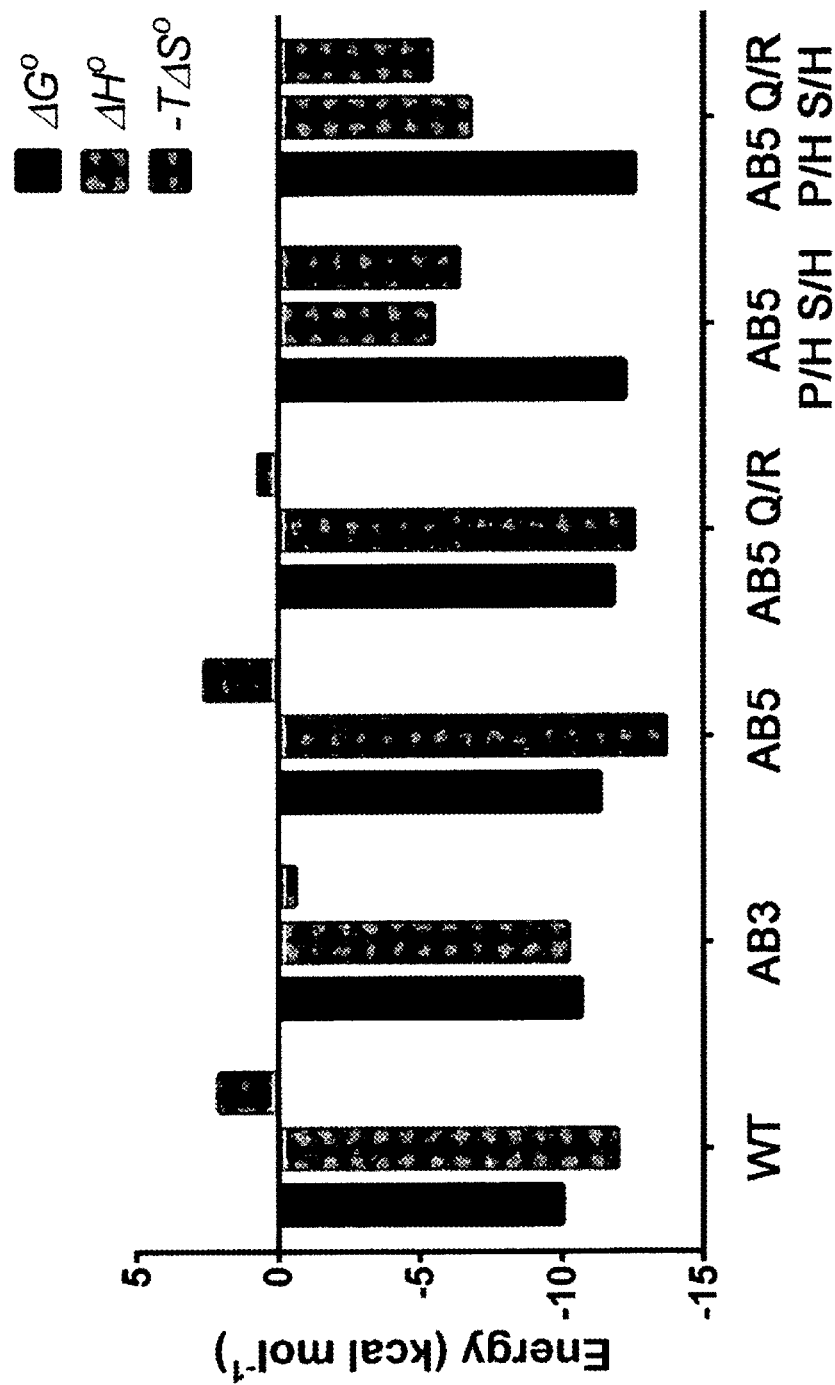
Figure 5:
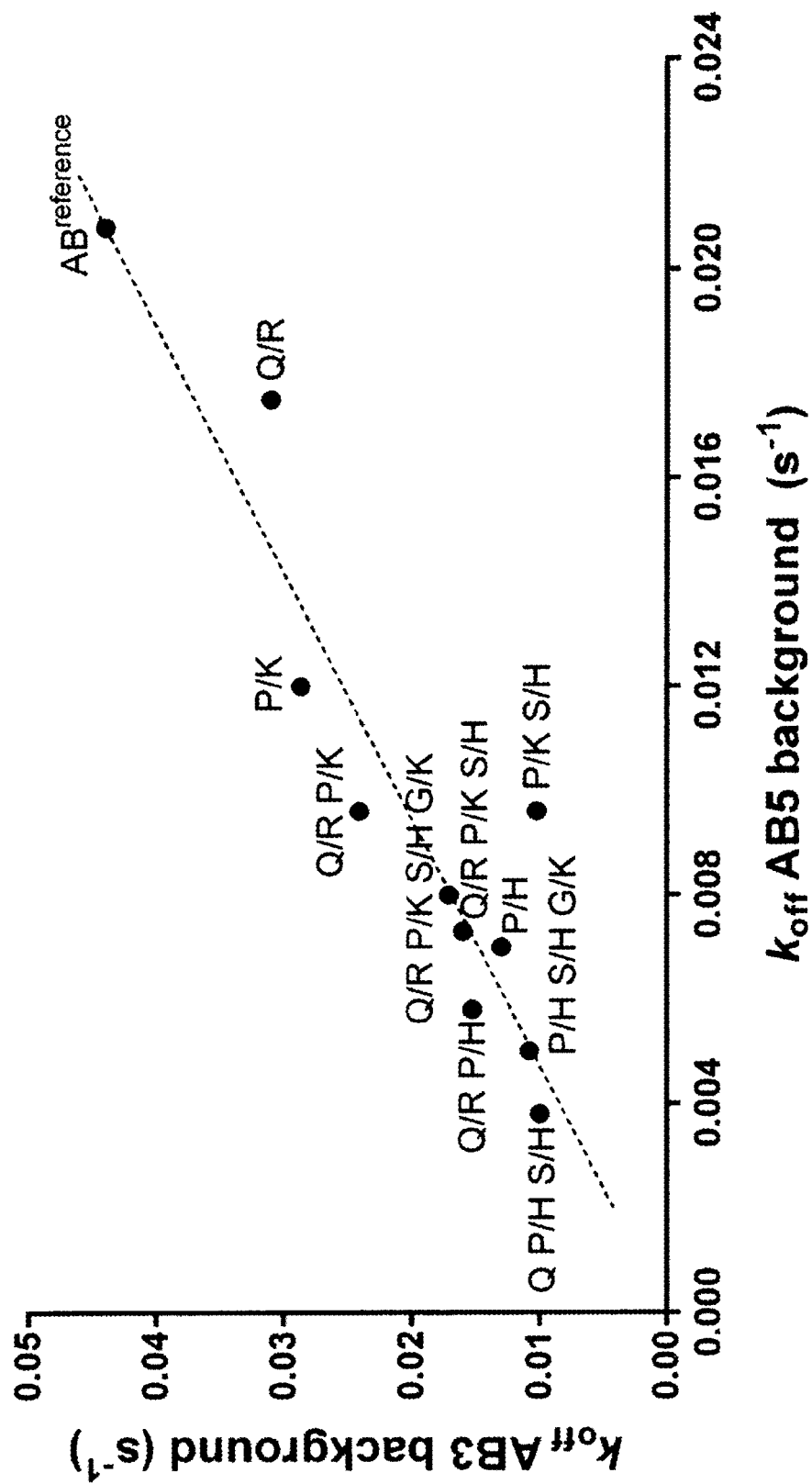
Figure 6A:
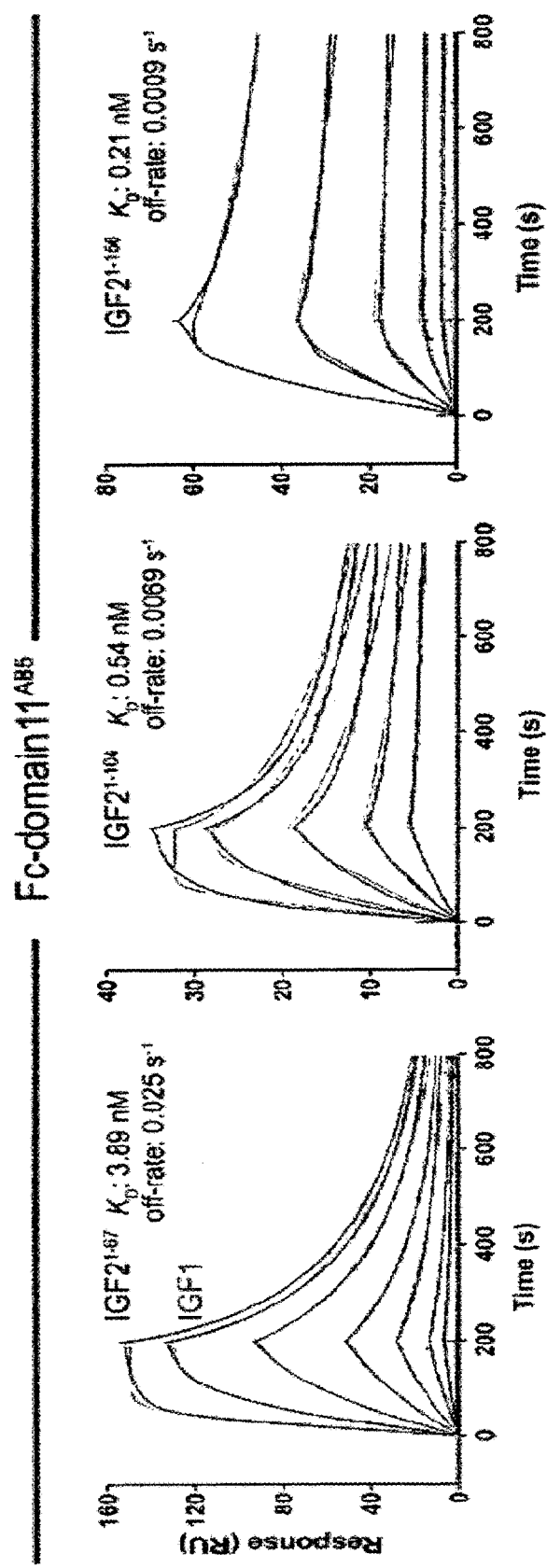
Figure 6B:
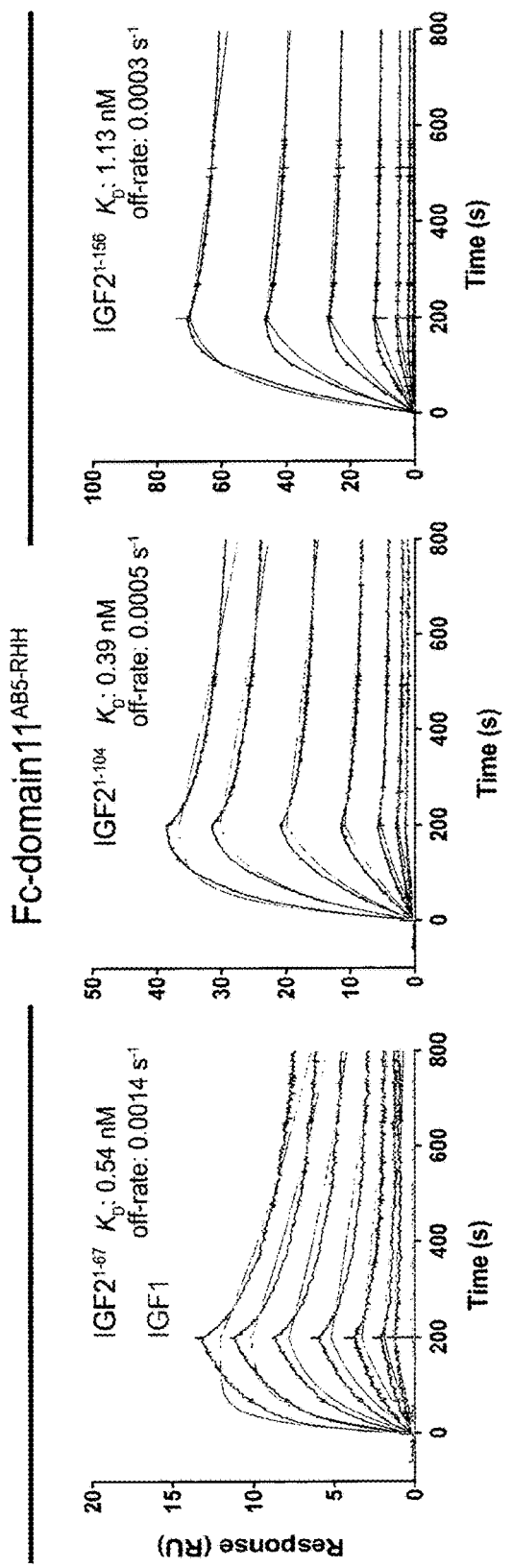
Figure 6C:
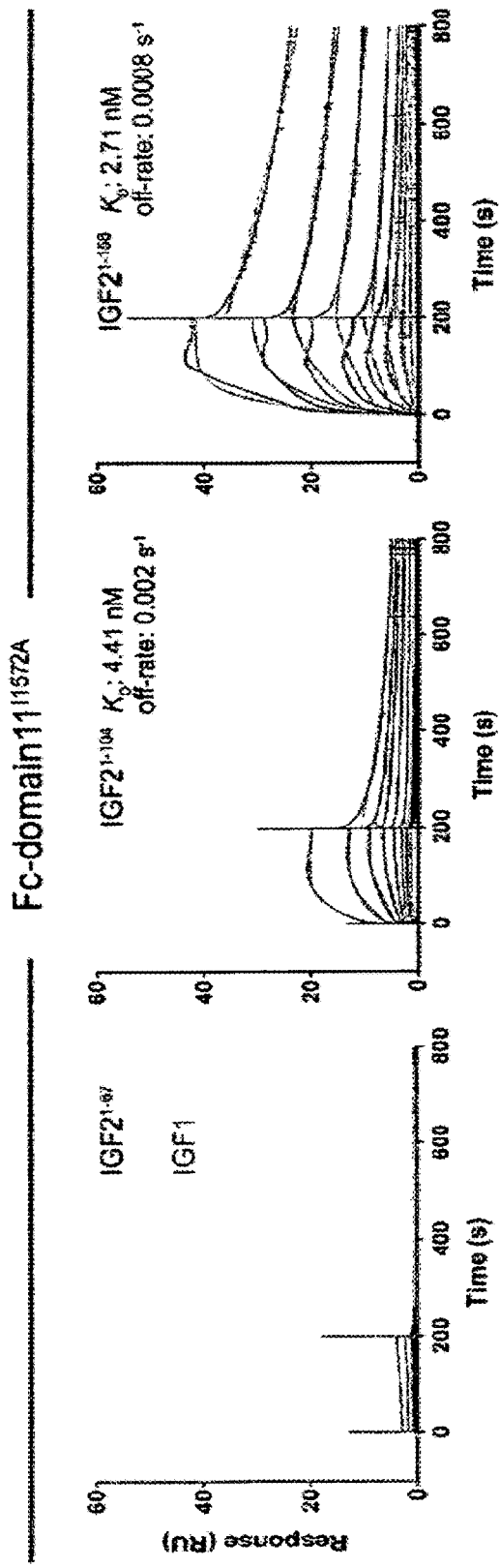
Figure 7:
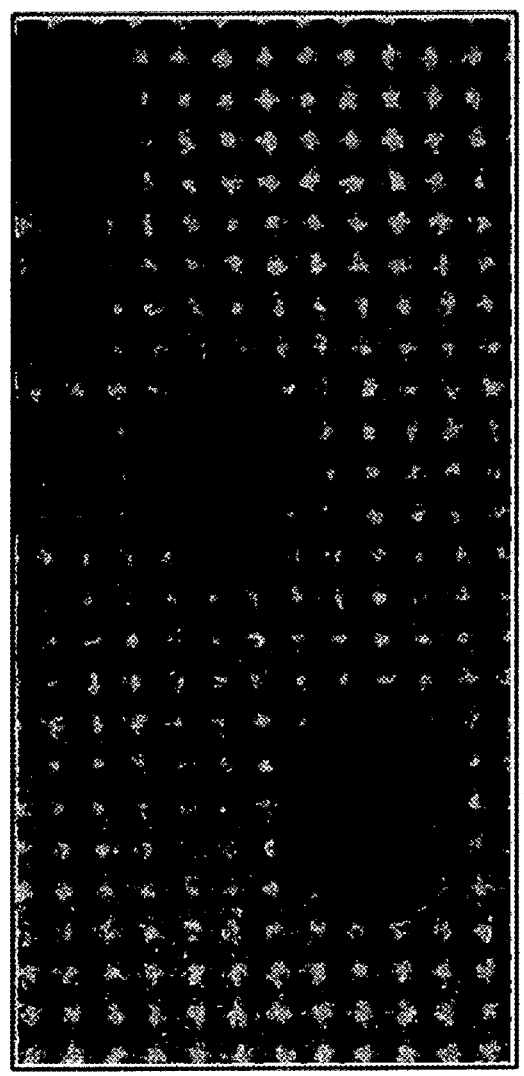
Figure 8:
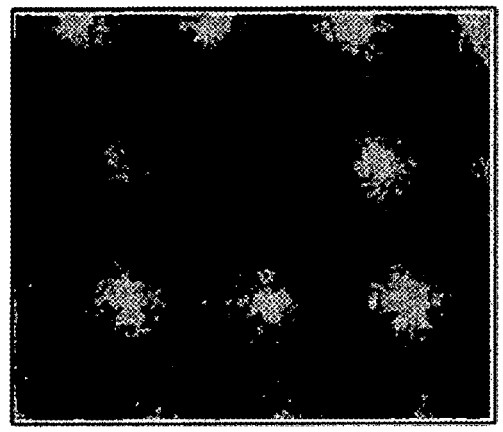
Figure 8:
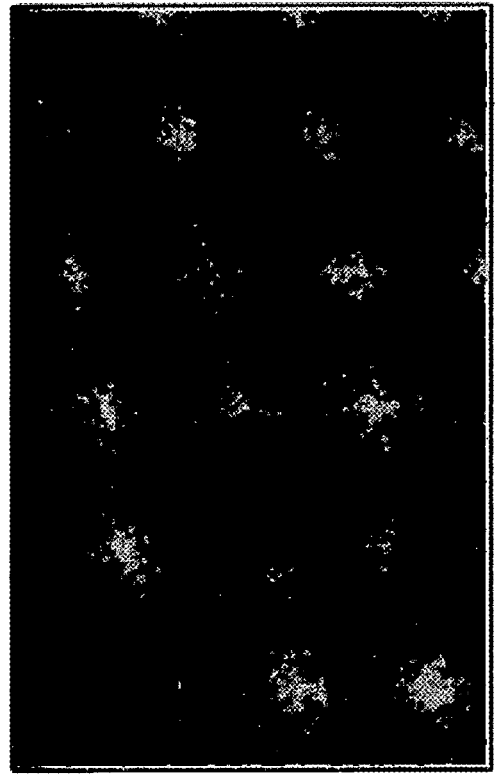
Figure 9:
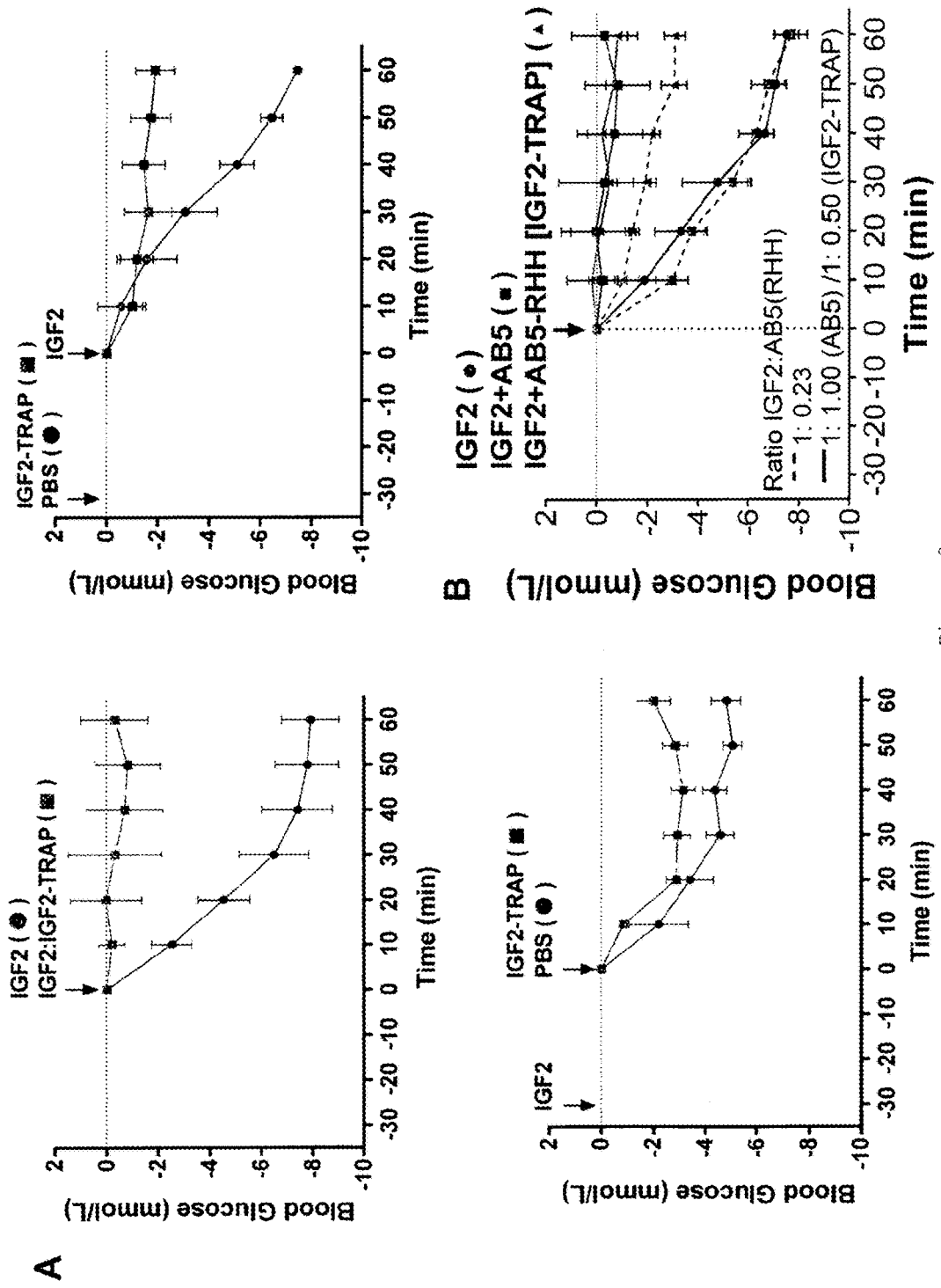
Figure 10A:
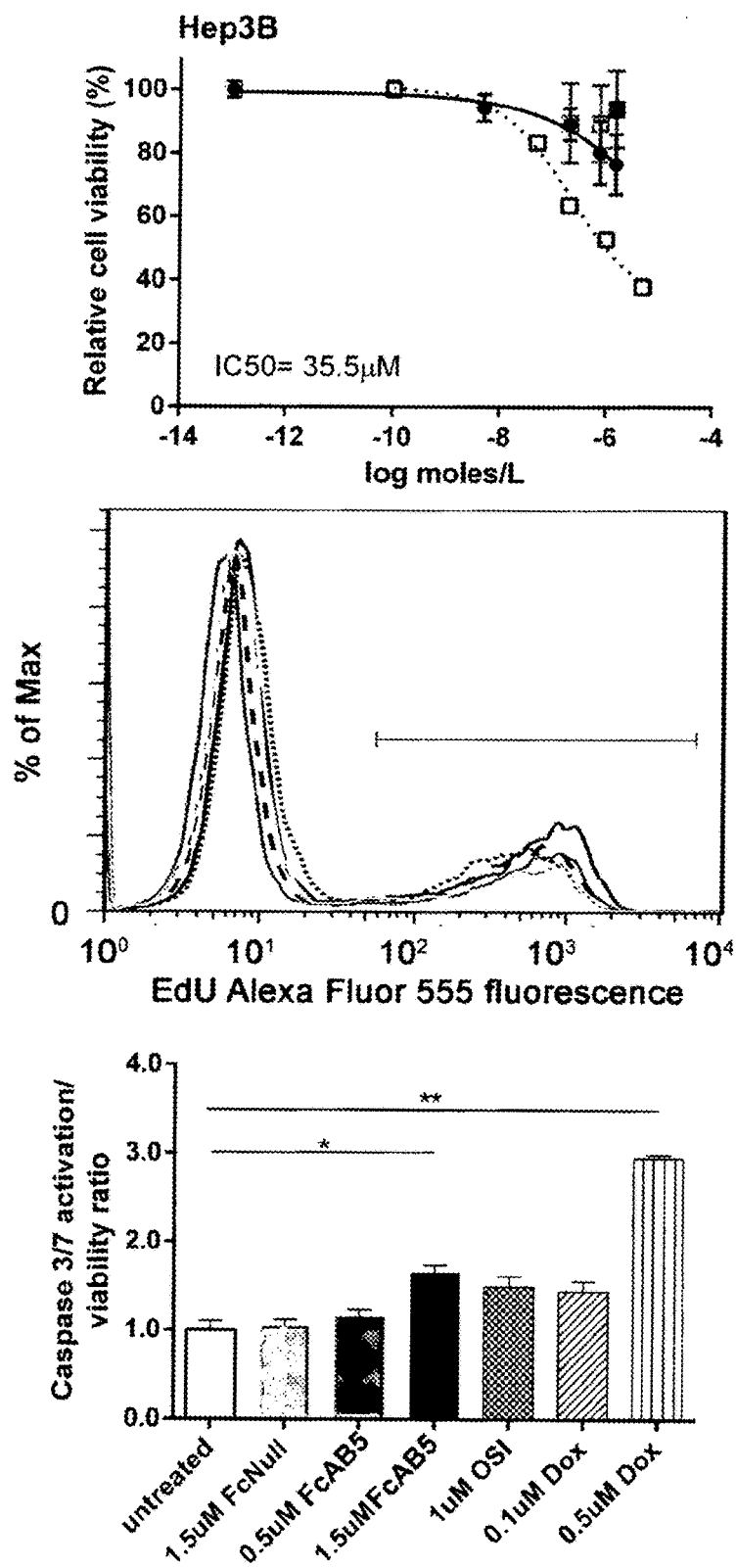
Figure 10B:
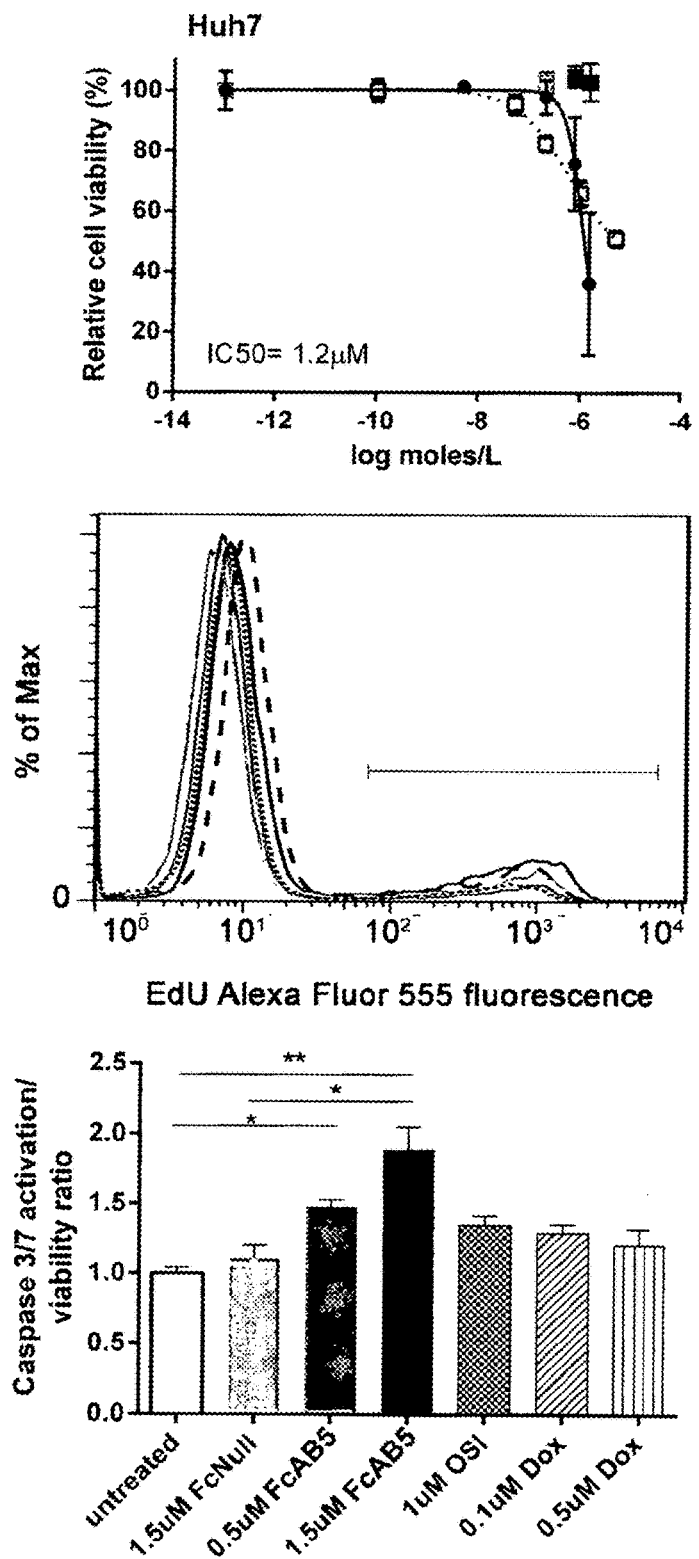
Figure 11:
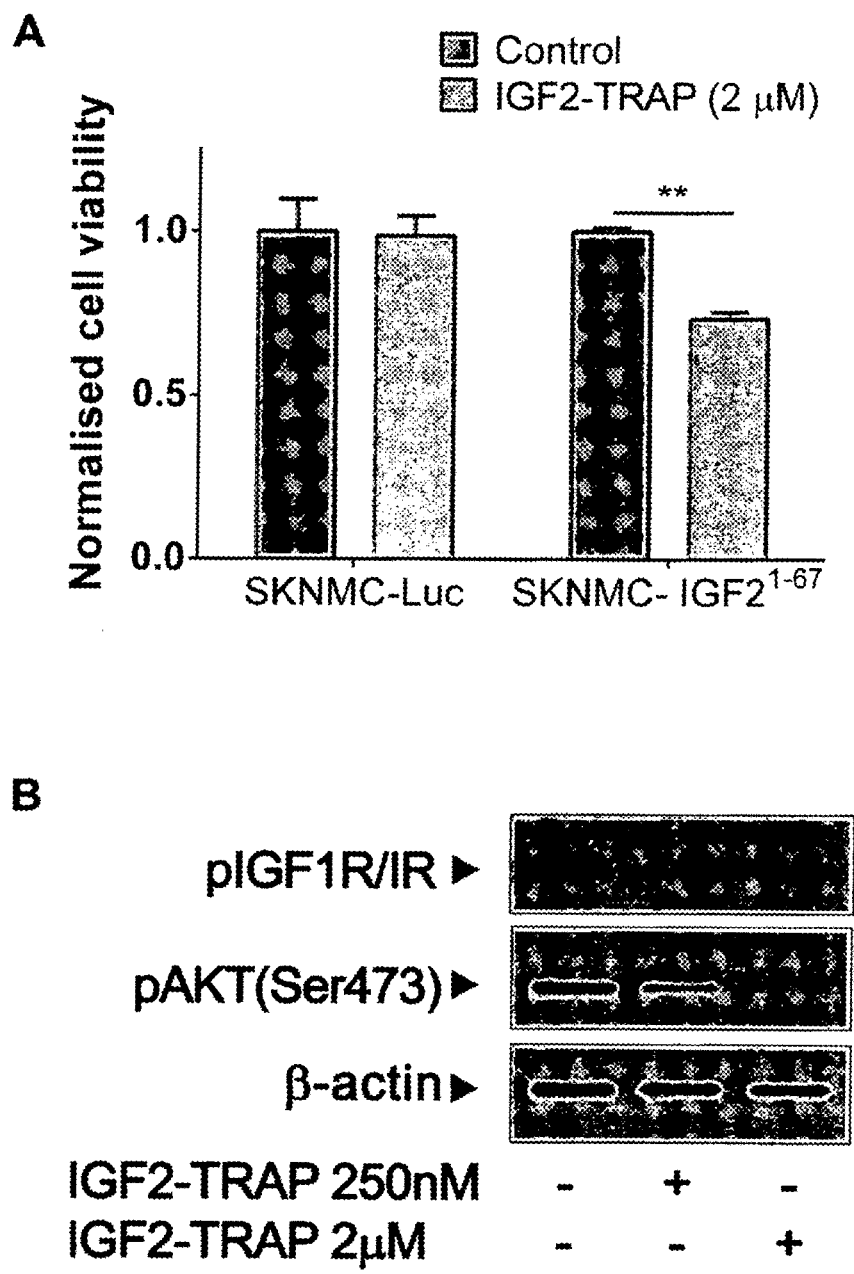
(FIG. 11B) Western blot of Fc-domain IGF2-TRAP effect on IGF2 dependent phosphorylation of IGF1R and IR-A, and of AKTS473, in SKNMC-IGF2$^{1-67}$.
Figure 12A:
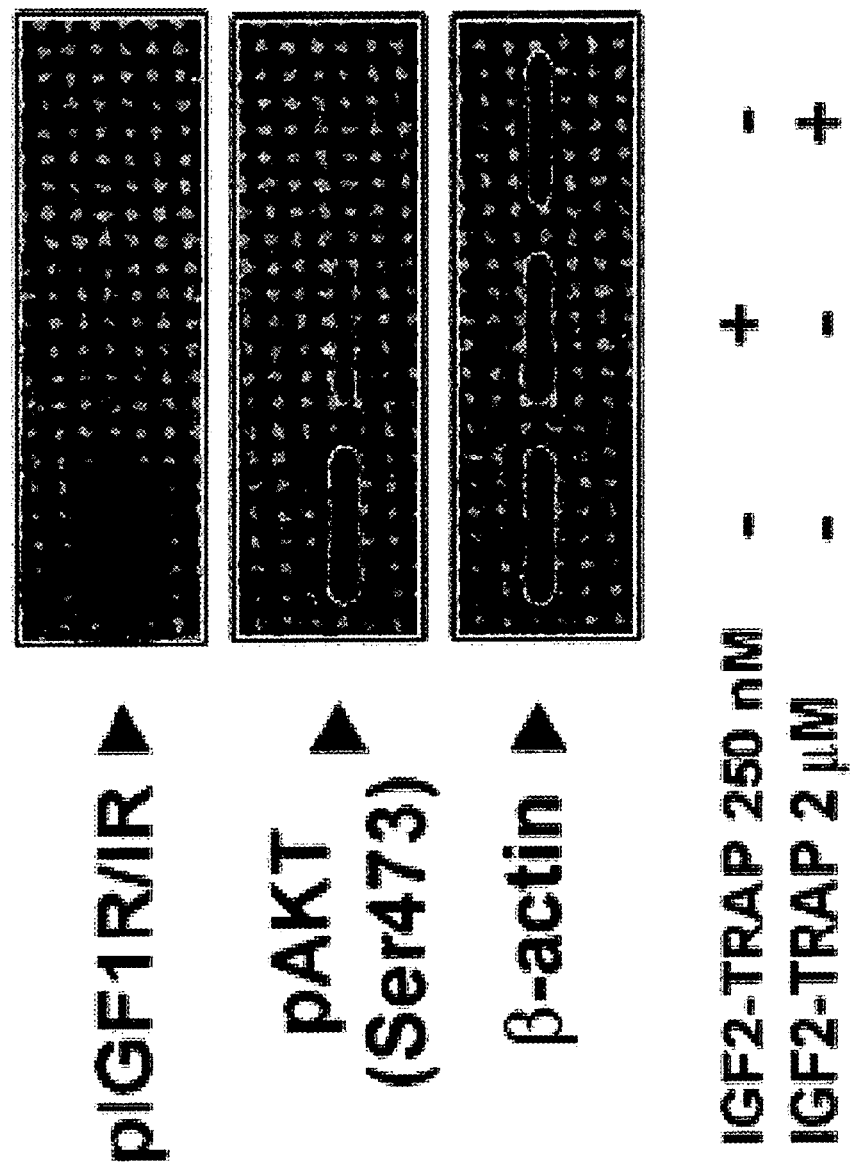
FIGS. 12A-12C show Fc-domain 11$^{AB5-RHH}$ (IGF2-TRAP) inhibition of IGF2 signalling in vivo.
Figure 12B:
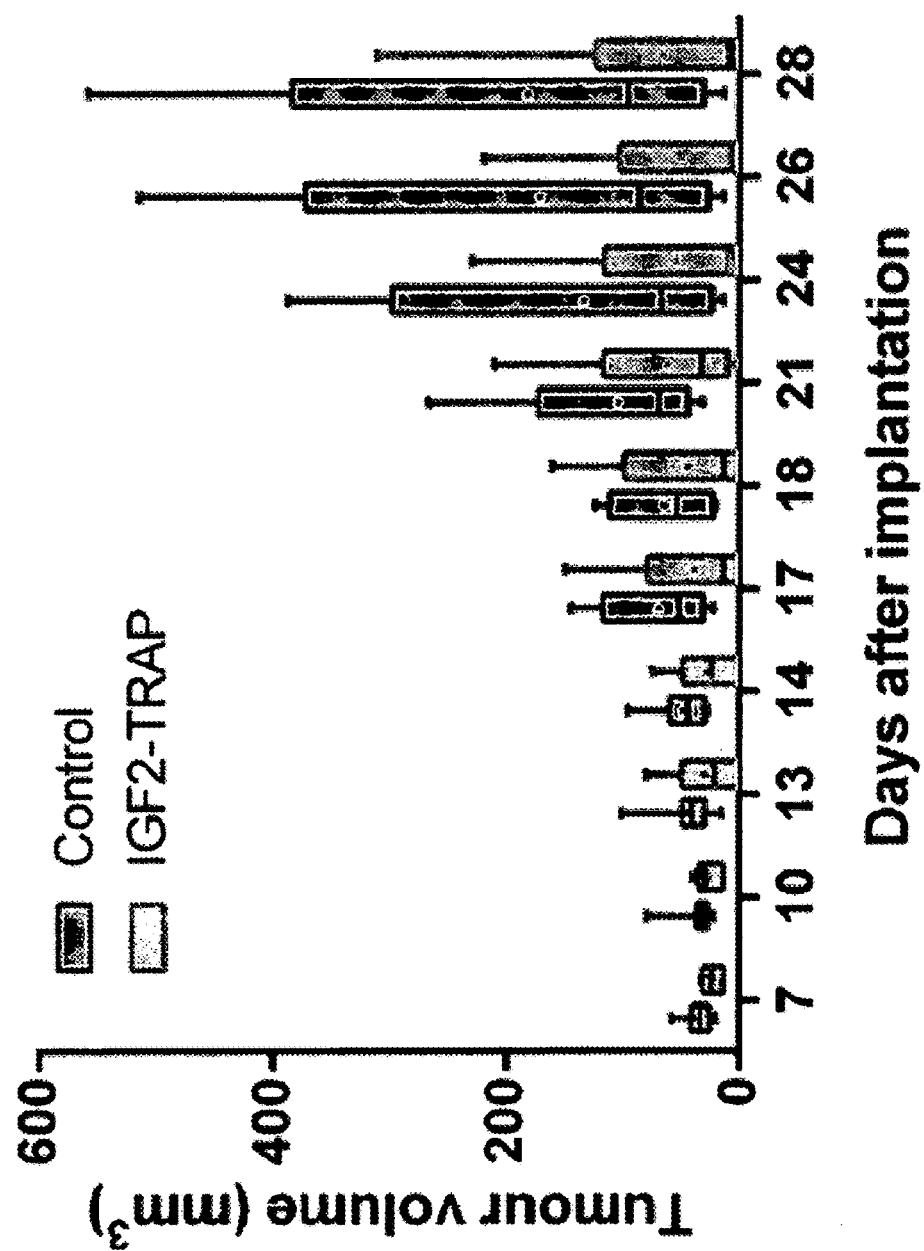
Figure 12C:
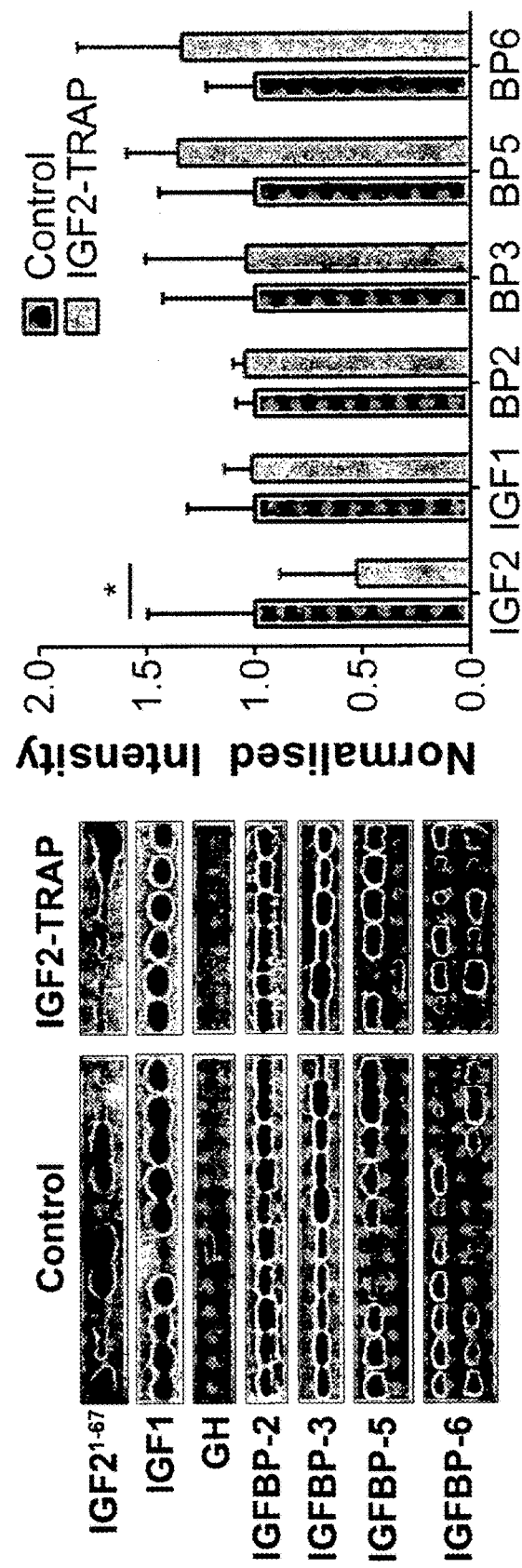

This invention relates to mutant IGF2 binding domains in which residue P1597 and optionally one or more other residues are mutated. Proline has an important structural function in proteins, so the beneficial effect of mutation at P1597 was unexpected.

The mutant IGF2 binding domains have increased affinity for IGF2 compared to the wild-type IGF2 binding domain (residues 1511 to 1650) of human IGF2R, for example 20 fold or greater, 30 fold or greater, 50 fold or greater, 75 fold or greater or 100 fold or more greater affinity. In some embodiments, a mutant IGF2 binding domain may have 50 to 75 fold greater affinity for IGF2 than the wild-type human IGF2 binding domain.

A mutant IGF2 binding domain described herein may bind to IGF2 with a lower dissociation constant ($K_D$) than the wild-type IGF2 binding domain of IGF2R ($K_D$ of 40-60 nM). For example, a mutant IGF binding domain may bind IGF2 with a Kd of 10 nM or less, 5 nM or less or 1 nM or less. In some embodiments, a mutant IGF2 binding domain may bind IGF2 with a Kd of 0.1 nM to 1 nM, preferably 0.5 nM to 1 nM.

Preferably, the specificity of the mutant IGF2 binding domain is similar to that of the wild-type IGF2 binding domain (residues 1511 to 1650) of human IGF2R, i.e. it binds to IGF2 and shows no binding or substantially no binding to IGF1.

Wild-type human IGF2R has the amino acid sequence of SEQ ID NO: 1 and database entry NP_000867.1 GI: 4504611 and is encoded by the nucleotide sequence of SEQ ID NO: 2 and database entry (NM_000876.1 GI: 4504610).

The IGF2 binding domain is located at residues 1511 to 1650 of the full length human IGF2R sequence (SEQ ID NO: 1). The amino acid sequence of residues 1511 to 1650 of human IGF2R is shown in SEQ ID NO: 3.

Residues are numbered herein with reference to the full length human IGF2R sequence of SEQ ID NO: 1 unless otherwise stated. A residue identified by its position in the human IGF2R sequence may easily be identified in a truncated or variant IGF2R sequence, such as the IGF2 binding domain sequence shown in SEQ ID NO: 3, or variants thereof, using standard sequence analysis tools.

A mutant IGF2 binding domain described herein may consist of the amino acid sequence of residues 1511 to 1650 of wild-type human IGF2R with 30 or fewer amino acid residues mutated or otherwise altered, preferably 20 or fewer, 15 or fewer, 10 or fewer, or 8 or fewer. The mutated amino acid residues in the mutant IGF2 binding domain may include substitution at residue P1597 and optionally further substitutions at one or more of residues S1543, E1544, K1545, G1546, L1547, Q1569, S1602, G1603 and K1631 as described herein.

Unless otherwise stated, an amino acid residue in the mutant IGF2 binding domain may be mutated by insertion, deletion or substitution of one or more amino acids relative to the wild-type IGF2R amino acid sequence. Such alterations may be caused by one or more of addition, insertion, deletion or substitution of one or more nucleotides in the encoding nucleic acid.

In some embodiments, one or both of residues F1567 and I1572 are not mutated in the mutant IGF2 binding domain.

Preferably, the mutant IGF-II domain retains the β-barrel structure of the wild-type domain.

In some preferred embodiments, the IGF2 binding domain may consist of the amino acid sequence of residues 1511 to 1650 of human IGF2R with residue P1597 substituted for a different residue and one, two, three, four, five, six, seven, eight or all nine residues selected from S1543, E1544, K1545, G1546, L1547, Q1569, S1602, G1603 and K1631 substituted for different residues.

The mutant IGF2 binding domain may share at least 80% sequence identity with the wild-type amino acid sequence of residues 1511 to 1650 of human IGF2R, at least 85%, at least 90%, at least 95% or at least 98%. The sequence may share at least 80% sequence similarity with the wild-type sequence, at least 85% similarity, at least 90% similarity, at least 95% similarity or at least 99% similarity.

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine.

Sequence similarity and identity are commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST or TBLASTN (which use the method of Altschul et al. (1990) *J. Mol. Biol.* 215: 405-410), NBLAST and XBLAST (Altschul et al., 1991, *Nucleic Acids Res.*, 25:3389-3402), FASTA (which uses the method of Pearson and Lipman (1988) *PNAS USA* 85: 2444-2448), the Smith-Waterman algorithm (Smith and Waterman (1981) *J. Mol Biol.* 147: 195-197), Gapped BLAST, BLAST-2, WU-BLAST-2 (Altschul et al., 1996,

*Methods in Enzymology*, 266:460-480), ALIGN, ALIGN-2 (Genentech, Calif. USA), Megalign (DNASTAR), and the Bestfit program (Wisconsin Sequence Analysis Package, Genetics Computer Group, WI USA 53711), generally employing default parameters.

Sequence comparisons are preferably made over the full-length of the relevant sequence described herein.

In the mutant IGF2 binding domain, residue P1597 may be substituted for an uncharged polar residue, such as S, N or Q, an aliphatic residue such as L, or a basic residue, such as K, R or H. Preferably, residue P1597 is substituted for K or H.

In addition to substitution at residue P1597, residues Q1569, S1602 and/or G1603 of said amino acid sequence may also be substituted for a different residue.

For example, Q1569 of said amino acid sequence may be substituted for a basic residue, such as K, R or H, most preferably R. S1602 of said amino acid sequence may be substituted for N or Q or a basic residue, such as K, R or H, most preferably H. G1603 of said amino acid sequence may be substituted for a basic residue, such as K, R or H, most preferably K.

In addition to substitution at P1597 and optionally Q1569, S1602 and/or G1603, the mutant IGF2 binding domains described herein may further comprise one, two, three or more substitutions in the AB loop at residues 1542 to 1547 of the wild type IGF2R amino acid sequence.

In some embodiments, the AB loop of the mutant IGF2 binding domain may contain no more than eight substituted amino acid residues in total.

S1543 of the wild-type IGF2R amino acid sequence may be substituted for a different residue, for example an aliphatic residue, such as G, A, V, L or I, most preferably A.

E1544 of the wild type IGF2R amino acid sequence may be substituted for an aliphatic residue such as A, V, L or I, a basic residue such as K, R or H, a sulphur containing residue such as C or M, or a hydroxyl residue, such as S or T. More preferably, E1544 may be substituted for a polar residue, such as S, or a basic residue, such as K, R or H. For example, the mutant IGF2 binding domain may include a K, R, H or S residue at position 1544 (position 34 in SEQ ID NO: 3). In some embodiments, E1544 is substituted for R or K, preferably K. In other embodiments, E1544 is not mutated.

K1545 of the wild type IGF2R amino acid sequence may be substituted for a different residue, most preferably G or S.

G1546 of the wild type IGF2R amino acid sequence may be substituted for a different residue, most preferably a hydrophobic residue, such as W.

L1547 of the wild type IGF2R amino acid sequence may be substituted for a different residue, most preferably an aliphatic residue, such as G or V.

In some embodiments, the mutant IGF2 binding domain may comprise the substitutions S1543A, E1544K, K1545G, G1546W and L1547G i.e. the mutant IGF2 binding domain may comprise the sequence YAKGWG at residues 1542 to 1547 (i.e. the AB loop region).

In other embodiments, the mutant IGF2 binding domain may comprise the substitutions E1544K, K1545S, and L1547V i.e. the mutant IGF2 binding domain described herein may further comprise the sequence YSKSGV at residues 1542 to 1547 (i.e. the AB loop region).

In preferred embodiments, a mutant IGF2 binding domain may comprise substitutions at 6 or more, 7 or more or 8 or more positions selected from S1543, E1544, K1545, G1546, L1547, Q1569, P1597, S1602 and G1603 of the wild-type IGF2R sequence.

In a first group of preferred embodiments, a mutant IGF2 binding domain may comprise substitutions at S1543, E1544, K1545, G1546, L1547, Q1569, P1597 and S1602 of the wild-type IGF2R sequence. For example, a mutant IGF2 binding domain may comprise the substitutions S1543A, E1544K, K1545G, G1546W, L1547G, Q1569R P1597H and S1602H or the substitutions S1543A, E1544K, K1545G, G1546W, L1547G, Q1569R, P1597K and S1602H. Suitable mutant IGF2 binding domains may comprise the amino acid sequence of residues 1511 to 1650 of human IGF2R with 30 or fewer of said residues mutated; or an amino acid sequence which has at least 80% sequence identity with residues 1511 to 1650 of human IGF2R, as described above.

In some embodiments, the mutant IGF2 binding domain may consist of the amino acid sequence of residues 1511 to 1650 of human IGF2R with the substitutions S1543A, E1544K, K1545G, G1546W, L1547G, Q1569R, P1597H and S1602H or the substitutions S1543A, E1544K, K1545G, G1546W, L1547G, Q1569R, P1597K and S1602H.

In a second group of preferred embodiments, a mutant IGF2 binding domain may comprise substitutions at S1543, E1544, K1545, G1546, L1547, Q1569, P1597 and G1603. For example, a mutant domain may comprise the substitutions S1543A, E1544K, K1545G, G1546W, L154G, Q1569R, P1597H and G1603K or the substitutions S1543A, E1544K, K1545G, G1546W, L154G, Q1569R, P1597K and G1603K. Suitable mutant IGF2 binding domains may comprise the amino acid sequence of residues 1511 to 1650 of human IGF2R with 30 or fewer of said residues mutated; or an amino acid sequence which has at least 80% sequence identity with residues 1511 to 1650 of human IGF2R, as described above.

In some embodiments, the mutant IGF2 binding domain may consist of the amino acid sequence of residues 1511 to 1650 of human IGF2R with the substitutions S1543A, E1544K, K1545G, G1546W, L154G, Q1569R, P1597H and G1603K or the substitutions S1543A, E1544K, K1545G, G1546W, L154G, Q1569R, P1597K and G1603K.

In a third group of preferred embodiments, a mutant IGF2 binding domain may comprise substitutions at E1544, K1545, L1547, Q1569, P1597 and S1602 of the wild-type IGF2R sequence. For example, a mutant domain may comprise the substitutions E1544K, K1545S, L1547V, Q1569R, P1597H and S1602H or the substitutions E1544K, K1545S, L1547V, Q1569R, P1597K and S1602H. Suitable mutant IGF2 binding domains may comprise the amino acid sequence of residues 1511 to 1650 of human IGF2R with 30 or fewer of said residues mutated; or an amino acid sequence which has at least 80% sequence identity with residues 1511 to 1650 of human IGF2R, as described above.

In some embodiments, the mutant IGF2 binding domain may consist of the amino acid sequence of residues 1511 to 1650 of human IGF2R with the substitutions E1544K, K1545S, L1547V, Q1569R, P1597H, and S1602H or the substitutions E1544K, K1545S, L1547V, Q1569R, P1597K and S1602H.

In a fourth group of preferred embodiments, a mutant IGF2 binding domain may comprise substitutions at E1544, K1545, L1547, Q1569, P1597, S1602 and G1603 of the wild-type IGF2R sequence. For example, a mutant domain may comprise the substitutions E1544K, K1545S, L1547V, Q1569R, P1597H, S1602H and G1603K or the substitutions E1544K, K1545S, L1547V, Q1569R, P1597K, S1602H and G1603K. Suitable mutant IGF2 binding domains may comprise the amino acid sequence of residues 1511 to 1650 of human IGF2R with 30 or fewer of said residues mutated; or an amino acid sequence which has at least 80% sequence identity with residues 1511 to 1650 of human IGF2R, as described above.

In some embodiments, the mutant IGF2 binding domain may consist of the amino acid sequence of residues 1511 to 1650 of human IGF2R with the substitutions E1544K, K1545S, L1547V, Q1569R, P1597H, S1602H and G1603K or the substitutions E1544K, K1545S, L1547V, Q1569R, P1597K, S1602H and G1603K.

A mutant IGF2 binding domain as described herein may comprise one or more non-natural amino acids, modified amino acids or d-amino acids. The use of such amino acids is well-known to those of skill in the art.

A mutant IGF2 domain as described above may be comprised within a polypeptide.

The polypeptide may comprise multiple IGF2 binding domains, including, for example, one or more mutant IGF2 binding domains as described herein. For example, a polypeptide may comprise two, three, four or more IGF2 binding domains. The presence of multiple domains may increase the ability of the polypeptide to bind to IGF2. The domains may be identical (i.e. copies) or may be non-identical (i.e. they may differ at one or more amino acid residues).

The mutant IGF2 binding domains may be directly connected without linkers or may be linked by amino acid sequences from human IGF2R, synthetic amino acid sequences, synthetic organic molecules or polypeptides that multimerise or assemble into polymeric structures. In some embodiments, the IGF2 binding domains may be linked via biotin-streptavidin tags.

The polypeptide may further comprise one or more amino acid sequences additional to the one or more mutant IGF2 binding domains. For example, the IGF2 binding polypeptide may comprise one or more additional domains.

Additional domains may include domains of human IGF2R, such as domain 13 (residues 1800 to 1991 of the IGF2R sequence), and domain 12 (residues 1651 to 1799 of the IGF2R sequence) or domains from other polypeptides (i.e. heterologous domains) which improve the stability, pharmacokinetic, targeting, affinity, purification and production properties of the polypeptide, such as an immunoglobulin Fc domain, which confers improved stability/pharmacokinetic parameters in biological fluid.

A mutant IGF2 binding domain may be linked to an immunoglobulin, such as IgG1 or IgG2, or part of an immunoglobulin, such as an Fc domain. Suitable immunoglobulins include human immunoglobulins.

In some embodiments, the polypeptide may comprise an affinity tag, which may, for example, be useful for purification. An affinity tag is a heterologous peptide sequence which forms one member of a specific binding pair. Polypeptides containing the tag may be purified by the binding of the other member of the specific binding pair to the polypeptide, for example in an affinity column. For example, the tag sequence may form an epitope which is bound by an antibody molecule.

Suitable affinity tags include for example, glutathione-S-transferase, (GST), maltose binding domain (MBD), MRGS (H)$_6$, DYKDDDDK (FLAG™), T7-, S-(KETAAAKFER-QHMDS), poly-Arg (R$_{5-6}$), poly-His (H$_{2-10}$), poly-Cys (C$_4$) poly-Phe(F$_{11}$) poly-Asp(D5-16), Strept-tag II (WSH-PQFEK), c-myc (EQKLISEEDL), Influenza-HA tag [25], Glu-Glu-Phe tag [26], SPY-TAG (AHIVMVDAYKPTK; [52]) Tag. 100 (Qiagen; 12 aa tag derived from mammalian MAP kinase 2), Cruz tag 09™ (MKAEFRRQESDR, Santa Cruz Biotechnology Inc.) and Cruz tag 22™ (MRDALDRL-DRLA, Santa Cruz Biotechnology Inc.). Known tag sequences are reviewed in Terpe et al (2003) [53].

In preferred embodiments, a FLAG™ or poly-His tag such as (H)$_6$ or MRGS(H)$_6$ may be used.

The affinity tag sequence may be removed after purification, for example, using site-specific proteases.

In some embodiments, the polypeptide may be coupled to an appropriate signal leader peptide to direct secretion from cell into the culture medium. A range of suitable signal leader peptides are known in the art. The signal leader peptide may be heterologous to the IGF binding domain i.e. it may be a non-IGF2R signal sequence. For example, an α-factor secretion signal may be employed. Preferably, the signal peptide is removed by post-translational processing after expression of the polypeptide.

Preferably, a polypeptide comprising or consisting of one or more IGF2 binding domains is soluble. A soluble polypeptide does not naturally associate with membranes after expression and does not form aggregates in aqueous solution under physiological conditions. A soluble polypeptide may, for example, lack a transmembrane domain.

In some embodiments, the polypeptide may be immobilised. For example, the polypeptide may be covalently or non-covalently attached to an insoluble support. The support may be in particulate or solid form and may include a plate, a test tube, beads, a ball, a filter or a membrane. A polypeptide may, for example, be fixed to an insoluble support that is suitable for use in affinity chromatography. Methods for fixing polypeptides to insoluble supports are known to those skilled in the art. A polypeptide may be immobilised, for example, to isolate IGF2 from a sample.

Mutant IGF2 binding domains and polypeptides may be generated wholly or partly by chemical synthesis. For example, the domains and polypeptides may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof. Chemical synthesis of polypeptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A Users Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A 10 Practical Approach. IRL Press 1989 and in G. B. Fields, (Ed.) Solid Phase Peptide Synthesis (Methods in Enzymology Vol. 289). Academic Press, New York and London 1997).

In some embodiments, a polypeptide comprising or consisting of one or more IGF2 binding domains may be labelled with a detectable or functional label.

Detectable labels may include radionuclides, such as iodine-131, yttrium-90, indium-111 and technicium-99, which may be attached to polypeptides of the invention using conventional chemistry known in the art. A polypeptide labelled with a radioactive isotope may be used to selectively deliver radiation to a specific target, such as a tumour. This may be useful in imaging the tumour or in delivering a cytotoxic dose of radiation, as described below.

Other detectable labels may include enzyme labels such as horseradish peroxidase, chemical moieties such as biotin which may be detected via binding to a specific cognate detectable moiety, e.g. labelled avidin, fluorochromes such as fluorescein, rhodamine, phycoerythrin and Texas Red and near infrared fluorophores, including cyanine dye derivatives such as Cy7 (Amersham Pharmacia) and Alexa750 (Molecular probes).

In some embodiments, a polypeptide comprising or consisting of one or more IGF2 binding domains may be linked to a reactive moiety for the covalent attachment of additional molecules. Suitable reactive moieties include photoaffinity groups, such as cyclopropenones, e.g. for click chemistry reactions.

Mutant IGF2 binding domains and polypeptides may be generated wholly or partly by recombinant techniques. For example, a nucleic acid encoding a mutant IGF2 binding domain or polypeptide may be expressed in a host cell and the expressed polypeptide isolated and/or purified from the cell culture.

Another aspect of the invention provides a nucleic acid encoding a polypeptide comprising or consisting of one or more mutant IGF2 binding domains as described herein, and optionally one or more additional domains, as described above.

Nucleic acid encoding a polypeptide may be comprised in a vector. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in mammalian cells. A vector may also comprise sequences, such as origins of replication and selectable markers, which allow for its selection and replication in bacterial hosts such as *E. coli*.

Vectors may be plasmids, viral e.g. 'phage, or phagemid, as appropriate. For further details see, for example, Molecular Cloning: a Laboratory Manual: 3rd edition, Russell et al., 2001, Cold Spring Harbour Laboratory Press. Many known techniques and protocols for manipulation of nucleic acid, for example in preparation of nucleic acid constructs, mutagenesis, sequencing, introduction of DNA into cells and gene expression, are described in detail in Current Protocols in Molecular Biology, Ausubel et al. eds. John Wiley & Sons, 1992.

A nucleic acid or vector as described herein may be introduced into a host cell.

A range of host cells suitable for the production of recombinant polypeptides are known in the art. Suitable host cells may include prokaryotic cells, in particular bacteria such as *E. coli*, and eukaryotic cells, including mammalian cells such as CHO and CHO-derived cell lines (Lec cells), HeLa, COS, and HEK293 cells, amphibian cells such as *Xenopus* oocytes, insect cells such as *Trichoplusia ni*, Sf9 and Sf21 and yeast cells, such as *Pichia pastoris*.

Techniques for the introduction of nucleic acid into cells are well established in the art and any suitable technique may be employed, in accordance with the particular circumstances. For eukaryotic cells, suitable techniques may include calcium phosphate transfection, DEAE-Dextran, electroporation, liposome-mediated transfection and transduction using retrovirus or other virus, e.g. adenovirus, AAV, lentivirus or vaccinia. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduced nucleic acid may be on an extra-chromosomal vector within the cell or the nucleic acid may be integrated into the genome of the host cell. Integration may be promoted by inclusion of sequences within the nucleic acid or vector which promote recombination with the genome, in accordance with standard techniques.

The introduction may be followed by expression of the nucleic acid to produce the encoded polypeptide comprising or consisting of one or more mutant IGF2 binding domains. In some embodiments, host cells (which may include cells actually transformed although more likely the cells will be descendants of the transformed cells) may be cultured in vitro under conditions for expression of the nucleic acid, so that the encoded IGF2 binding polypeptide is produced. When an inducible promoter is used, expression may require the activation of the inducible promoter.

The expressed polypeptide comprising or consisting of one or more mutant IGF2 binding domains may be isolated and/or purified, after production. This may be achieved using any convenient method known in the art. Techniques for the purification of recombinant polypeptides are well known in the art and include, for example HPLC, FPLC or affinity chromatography. In some embodiments, purification may be performed using an affinity tag on the polypeptide as described above.

Polypeptides comprising or consisting of one or more mutant IGF2 binding domains which are produced as described may be investigated further, for example the pharmacological properties and/or activity may be determined. Methods and means of protein analysis are well-known in the art.

In some embodiments, a nucleic acid or vector as described herein may be introduced into a host cell that is suitable for administration and expression of the mutant IGF2 binding domain or polypeptide in an individual.

Another aspect of the invention provides a polypeptide comprising or consisting of one or more mutant IGF2 binding domains, a nucleic acid, or a host cell as described herein for use in a method of treatment of the human or animal body by therapy. For example, the polypeptide comprising a mutant IGF2 binding domain, nucleic acid or host cell as described herein may be used in a method of treatment of cancer.

Another aspect of the invention provides the use of a polypeptide comprising or consisting of one or more mutant IGF2 binding domains, a nucleic acid, or a host cell as described herein in the manufacture of a medicament for use in the treatment of cancer.

Cancers which may be treated as described herein include cancers characterised by up-regulation of IGF2 or the down-regulation of IGF2R, for example colorectal cancers such as intestinal adenoma, cervical cancers such as cervical carcinoma, lung cancers such as lung carcinoma, kidney cancers such as Wilms' tumour, muscle cancers such as rhabdomyosarcoma, bone cancers such as Ewing's sarcoma, endocrine cancers such as phaeochromocytoma, liver cancers such as hepatocellular carcinoma, brain tumours such as glioblastoma, breast cancers such as inflammatory breast cancers, upper gastrointestinal cancers such as pancreatic cancer, haematological cancers such as myeloma, soft tissue sarcomas, such as haemangiopericytoma, and cancers that either result in tumour related hypoglycaemia (Non-Islet cell tumour associated hypoglycaemia, or NICTH, or IGF2 syndrome, due to high circulating supply of big-IGF2 isoforms) related to increased circulating levels of IGF2 and/or express the IGF2 gene at high levels.

Another aspect of the invention provides a polypeptide comprising or consisting of one or more mutant IGF2 binding domains, a nucleic acid, or a host cell as described herein for use in a method of treatment of a non-cancer disorder characterised by up-regulation of IGF2 or the down-regulation of IGF2R, for example a disorder associated with proliferative vascular growth, such as diabetic retinopathy, a growth disorder associated with aberrant expression of IGF2, such as Beckwith-Wiedemann syndrome, or a bone-related metabolic disorder, such as hepatitis C-associated osteosclerosis (HCAO).

Another aspect of the invention provides the use of a polypeptide comprising or consisting of one or more mutant IGF2 binding domains, a nucleic acid, or a host cell as described herein in the manufacture of a medicament for use in the treatment of a disorder associated with proliferative vascular growth such diabetic retinopathy, a growth disorder associated with aberrant expression of IGF2, such as Beckwith-Wiedemann syndrome, or a bone-related metabolic disorder, such as hepatitis C-associated osteosclerosis (HCAO).

An individual with cancer or another condition who is suitable for treatment with a polypeptide comprising or consisting of one or more mutant IGF2 binding domains, a nucleic acid, or a host cell as described herein may display increased IGF2 protein expression, increased IGF2 mRNA expression, the presence of pro-forms of IGF2 and/or low blood glucose.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or leporid) may be employed.

In some embodiments, the individual may have minimal residual disease (MRD) after an initial cancer treatment.

An individual with cancer may display at least one identifiable sign, symptom, or laboratory finding that is sufficient to make a diagnosis of cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual. In some embodiments, the individual may have been previously identified or diagnosed with cancer or a method of the invention may comprise identifying or diagnosing cancer in the individual for example by determining the presence of an identifiable sign, symptom, or laboratory finding indicative of cancer in the individual.

Mutant IGF2 binding domains and polypeptides as described herein may also be useful as cancer-targeting agents to deliver other anti-cancer molecules to tumours, radiolabels to detect and treat tumours, and sensitising agents that sensitise tumours to other cancer therapies, including chemotherapy and radiotherapy.

Whilst a polypeptide comprising or consisting of one or more mutant IGF2 binding domains, a nucleic acid, or a host cell as described herein may be administered alone, it is preferable to present it as a pharmaceutical composition (e.g. formulation) which comprises the polypeptide, nucleic acid or cell, together with one or more pharmaceutically acceptable carriers, adjuvants, excipients, diluents, fillers, buffers, stabilisers, preservatives, lubricants, or other materials well known to those skilled in the art and, optionally, other therapeutic or prophylactic agents. Such materials should be non-toxic and should not interfere with the efficacy of the active compound. The precise nature of the carrier or other material will depend on the route of administration, which may be by bolus, infusion, injection or any other suitable route, as discussed below. Suitable materials will be sterile and pyrogen-free, with a suitable isotonicity and stability. Examples include sterile saline (e.g. 0.9% NaCl), water, dextrose, glycerol, ethanol or the like or combinations thereof. The composition may further contain auxiliary substances such as wetting agents, emulsifying agents, pH buffering agents or the like.

Methods of the invention may therefore comprise the step of formulating a polypeptide comprising or consisting of one or more mutant IGF2 binding domains, a nucleic acid, or a host cell as described herein with a pharmaceutically acceptable carrier, adjuvant or excipient.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be oral or by injection, e.g. cutaneous, subcutaneous, or intravenous or intraocular, for example intraorbital.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Suitable carriers, excipients, etc. can be found in standard pharmaceutical texts, for example, Remington's Pharmaceutical Sciences, 18th edition, Mack Publishing Company, Easton, Pa., 1990.

The pharmaceutical compositions and formulations may conveniently be presented in unit dosage form and may be prepared by any methods well known in the art of pharmacy.

Such methods include the step of bringing into association the mutant IGF2 binding domain, polypeptide, nucleic acid or host cell with the carrier which constitutes one or more accessory ingredients. In general, the compositions are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Whether it is a mutant IGF2 binding domain, polypeptide, nucleic acid or host cell according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the circumstances of the individual to be treated.

The mutant IGF2 binding domain or polypeptide or pharmaceutical composition comprising the mutant IGF2 binding domain or polypeptide may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal, preferably subcutaneous or intraorbital; by implant of a depot, for example, subcutaneously or intramuscularly. Usually administration will be by the oral route, although other routes such as intraperitoneal, subcutaneous, transdermal, intravenous, nasal, intramuscular or other convenient routes are not excluded.

The pharmaceutical compositions comprising the active compounds may be formulated in a dosage unit formulation that is appropriate for the intended route of administration.

Treatment may be any treatment or therapy, whether of a human or an animal (e.g. in veterinary applications), in which some desired therapeutic effect is achieved, for example, the inhibition or delay of the onset or progress of the condition, and includes a reduction in the rate of progress, a halt in the rate of progress, inhibition of metastasis, amelioration of the condition, cure or remission (whether partial or total) of the condition, preventing, delaying, abating or arresting one or more symptoms and/or signs of the condition or prolonging survival of a subject or individual beyond that expected in the absence of treatment.

Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), delayed tumor growth, or destruction of tumor vasculature. Administration of a mutant IGF2 binding domain as described herein in an individual with cancer, as described herein may improve the capacity of the individual to resist cancer growth, in particular growth of a cancer already present the subject and/or decrease the propensity for cancer growth in the individual.

Treatment as described herein may include prophylactic treatment (i.e. prophylaxis) i.e. the individual being treated may not have or may not be diagnosed as having a cancer at the time of treatment. For example, an individual susceptible to or at risk of the occurrence or re-occurrence of cancer may be treated as described herein. Such treatment may prevent or delay the occurrence or re-occurrence of cancer in the individual or reduce its symptoms or severity after occurrence or re-occurrence. In some embodiments, the individual may have been previously identified as having increased susceptibility or risk of cancer compared to the general population or a method may comprise identifying an individual who has increased susceptibility or risk of cancer. Prophylactic or preventative treatment may be preferred in some embodiments.

A mutant IGF2 binding domain may be administered as described herein in therapeutically-effective amounts.

The term "therapeutically-effective amount" as used herein, pertains to that amount of an active compound, or a combination, material, composition or dosage form comprising an active compound, which is effective for producing some desired therapeutic effect, commensurate with a reasonable benefit/risk ratio.

The appropriate dosage of an active compound may vary from individual to individual. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the individual. The amount of active compounds and route of administration will ultimately be at the discretion of the physician, although generally the dosage will be to achieve therapeutic plasma concentrations of the active compound without causing substantial harmful or deleterious side-effects.

In general, a suitable dose of the active compound is in the range of about 100 μg to about 400 mg per kilogram body weight of the subject per day, preferably 200 μg to about 200 mg per kilogram body weight of the subject per day, for example 5-10 mg/kg/day. Where the active compound is a salt, an ester, prodrug, or the like, the amount administered is calculated on the basis of the parent compound and so the actual weight to be used is increased proportionately.

Administration in vivo can be effected in one dose, continuously or intermittently (e.g., in divided doses at appropriate intervals).

Methods of determining the most effective means and dosage of administration are well known in the art and will vary with the formulation used for therapy, the purpose of the therapy, the target cell being treated, and the subject being treated. Single or multiple administrations can be carried out with the dose level and pattern being selected by the physician.

Multiple doses of the mutant IGF2 binding domain may be administered, for example 2, 3, 4, 5 or more than 5 doses may be administered. The administration of the mutant IGF2 binding domain may continue for sustained periods of time.

For example treatment with the mutant IGF2 binding domain may be continued for at least 1 week, at least 2 weeks, at least 3 weeks, at least 1 month or at least 2 months. Treatment with the mutant IGF2 binding domain may be continued for as long as is necessary to reduce cancer symptoms or achieve complete remission.

The mutant IGF2 binding domain may be administered alone or in combination with other treatments, either simultaneously or sequentially dependent upon the individual circumstances. For example, a mutant IGF2 binding domain as described herein may be administered in combination with one or more additional active compounds.

For example, a mutant IGF2 binding domain as described herein may be administered in combination with a phosphatidylinositol 3-kinase (PI3 kinase) inhibitor.

Suitable PI3 kinase inhibitors are well-known in the art and include F-04691502 ([2-amino-8-[trans-4-(2-hydroxyethoxy)cyclohexyl]-6-(6-methoxypyridin-3-yl)-4-methylpyrido-[2,3-d]pyrimidin-7(8H)-one), Pictilisib (GDC-0941; 4-[2-(1H-indazol-4-yl)-6-[(4-methylsulfonylpiperazin-1-yl) methyl]thieno[3,2-d]pyrimidin-4-yl]morpholine), perifosine (1,1-Dimethylpiperidinium-4-yl octadecyl phosphate), idelalsib (5-Fluoro-3-phenyl-2-[(1S)-1-(7H-purin-6-ylamino)propyl]-4(3H)-quinazolinone), PX866 ((1E,4S,4aR,5R,6aS,9aR)-5-(acetyloxy)-1-[(di-2-propen-1-ylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione), duvelisib (S)-3-(1-((9H-purin-6-yl)amino)ethyl)-8-chloro-2-phenylisoquinolin-1(2H)-one), copanlisib (2-Amino-N-[7-methoxy-8-(3-morpholin-4-ylpropoxy)-2,3-dihydroimidazo[1,2-c] quinazolin-5-yl]pyrimidine-5-carboxamide), pilaralisib (N-(3-{[(3-{[2-chloro-5-(methoxy)phenyl]amino}quinoxalin-2-yl)amino]sulfonyl}phenyl)-2-methylalaninamide); XL-765 (N-[2-[(3,5-Dimethoxyphenyl)amino]quinoxalin-3-yl]-4-[(4-methyl-3-methoxyphenyl)carbonyl]aminophenyl-sulfonamide) and BEZ-235 (2-methyl-2-(4-(3-methyl-2-oxo-8-(quinolin-3-yl)-2,3-dihydro-1H-imidazo[4,5-c] quinolin-1-yl)phenyl)propanenitrile).

Preferred PI3 kinase inhibitors include F-04691502 and pictilisib.

Other aspects of the invention provide a method of treating cancer or a non-cancer disorder characterised by up-regulation of IGF2 or the down-regulation of IGF2R comprising; administering a polypeptide comprising or consisting of one or more mutant IGF2 binding domains, a nucleic acid, or a host cell as described above to an individual in need thereof in combination with a PI3 kinase inhibitor.

Another aspect of the invention provides a polypeptide comprising or consisting of one or more mutant IGF2 binding domains, a nucleic acid, or a host cell as described above for use in a method of treating cancer or a non-cancer disorder characterised by up-regulation of IGF2 or the down-regulation of IGF2R, wherein the method comprises administering the polypeptide, nucleic acid or host cell in combination with a PI3 kinase inhibitor.

Another aspect of the invention provides a PI3 kinase inhibitor for use in a method of treating cancer or a non-cancer disorder characterised by up-regulation of IGF2 or the down-regulation of IGF2R, wherein the method comprises administering the PI3 kinase inhibitor with a polypeptide comprising or consisting of one or more mutant IGF2 binding domains, a nucleic acid, or a host cell as described above.

Another aspect of the invention provides a polypeptide comprising or consisting of one or more mutant IGF2 binding domains, a nucleic acid, or a host cell as described above and a PI3 kinase inhibitor for use in a method of treating cancer or a non-cancer disorder characterised by up-regulation of IGF2 or the down-regulation of IGF2R.

A mutant IGF2 binding domain as described herein may be useful in binding IGF2 in in vitro assays. For example, an assay may comprise contacting a mutant IGF2 binding domain as described herein with a sample that comprises IGF2 or is to be tested for the presence of IGF2, such that IGF2 in the sample binds to the mutant IGF2 binding domain to form a complex. The complex may be washed following binding of the IGF2 and the mutant IGF2 binding domain. The IGF2 may be separated from the mutant IGF2 binding domain following washing and subjected to further analysis. The amount of IGF2 may be determined, for example by mass spectrometry or immunostaining, before or after release from the complex.

The mutant IGF2 binding domain may be immobilised, for example on a bead or column.

In vitro binding assays using a mutant IGF2 binding domain may be useful in improving the assessment of the level of IGF2 in an individual, for example in IGF2 quantification prior to patient selection for treatment, the diagnosis of NICTH and the detection of exogenous administration of IGF2, such as in doping screens for athletes.

Another aspect of the invention provides the use of a mutant IGF2 binding domain to bind IGF2 in vitro.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above and the tables described below.

Table 1 shows the affinity kinetics of site directed mutants following structural predictions (domain $11^{AB3}$: IGF2). Surface plasmon resonance (SPR) binding analysis of recombinant M6P/IGF2R domain 11 mutants interaction with IGF2. Kon indicates association (on) rate; koff, dissociation (off) rate; RU, response units. Binding to IGF2 assessed with BIAcore T200 using purified biotinylated IGF2 and IGF1 on a streptavidin biosensor chip. Recombinant proteins were expressed either in *E. coli* and/or *P. pastoris*. All the mutants in the FG and CD loops are on the domain $11^{AB5}$ background for the AB loop unless otherwise stated. All experiments were carried out at 25° C. in HBS-EP buffer (pH 7.4), were repeated 2-5 times on two independent BIAcore chips. nd=not determined. Data for KD expressed as mean of each experiment, and means of kon and koff are shown.

Table 2 shows HI Loop mutagenesis library directed screen and domain $11^{AB3}$ random mutant characterisation.

Table 3 shows Affinity kinetics of combined CD, FG and HI, loop mutants with AB loop backgrounds domain $11^{AB3}$ and domain $11^{AB5}$. Measurements were carried out at 25° C. in HBS-EP buffer (pH 7.4) (nd=not determined, np=no protein). Data for KD expressed as mean of each experiment, and means of kon and koff are shown.

Table 4 shows pH dependent affinity kinetics of combined CD, FG and HI, loop mutants with AB loop backgrounds domain $11^{AB3}$ and domain $11^{AB5}$ (pH 6.5). Measurements were carried out at 25° C. in MES-EP buffer, 20 mM MES pH 6.5, 150 mM NaCl, 3 mM EDTA, and 0.005% (v/v) surfactant P20). Data for KD expressed as mean of each experiment, and means of kon and koff are shown.

Table 5 shows the affinity of IGF1 and the different forms of IGF2 ($IGF2^{1-67}$, $IGF2^{1-104}$ and $IGF2^{1-156}$) for the Fc domain $11^{AB5}$ and Fc-domain $11^{I1572A}$ fusion proteins. SPR analysis of the interaction of recombinant IGF1 and IGF2 forms with Fc-domain 11 proteins immobilised by antibody capture (CM5 chip containing monoclonal mouse anti-human IgG antibody immobilised by amine coupling). Measurements were carried out at 25° C. in HBS-EP buffer (pH 7.4).

EXPERIMENTS

Materials and Methods

Construction of Plasmids for Yeast Surface Display of IGF2R Domain 11 and Loop-Specific Mutagenesis The yeast surface display vector, pPICFlagDomain 11-Agα1, was generated by ligating IGF2R domain 11 (residues 1508-1654) into the EcoRI and AvrII restriction sites of pPIC9K preceded by the Flag peptide and followed by the C-terminal region of the *Saccharomyces cerevisiae* AGα1 gene. The resulting protein is a N-terminal Flag tagged fusion of domain 11 and the C-terminal domain (residues 311-650) of α-agglutinin, which targets the fusion protein to the cell surface through the secretory pathway, where it is attached by a GPI anchor [27]. The pLITMUS-Domain 11 vector was also generated by ligation of the Domain 11 insert into the EcoRI and AvrII restriction sites in the multipurpose cloning pLITMUS28i vector.

Construction of Loop-Specific Mutant Libraries

Loop-specific mutant libraries were generated by either whole plasmid PCR (using Kappa HiFi HotStart DNA polymerase, Kappa Biosystems, or Phusion Polymerase, Finnzymes), using tail-to-tail mutagenic primers pairs and the pPICFlagDomain11-Agα1 vector or the pLITMUS-Domain 11 vector as template for the AB loop and the HI loop libraries, respectively. The PCR product was treated with DpnI in order to remove the template, self-ligated and then transformed into XL10-Gold® ultra-competent *E. coli* cells (Stratagene) to generate the *E. coli* libraries. The presence of random amino acid mutations in the desired positions was confirmed by sequencing of 50 different clones of each library. In the case of the HI loop library, a midiprep of the *E. coli* pLITMUS-Domain $11^{HI}$ library (containing $8.3\times10^6$ clones and therefore covering the number of possible mutants by more than 10-fold) was digested with EcoRI and AvrII and the excised HI loop-mutated domain 11 was then ligated into the pPICFlag-Agα1 and transformed into the ultra-competent *E. coli* cells to generate the *E. coli* pPICFlagDomain $11^{HI}$-Agα library (containing $1.32\times10^6$ mutants). pPICFlagDomain $11^{AB}$-Agα1 and pPICFlagDomain $11^{HI}$-Agα1 were linearised within the HIS4 gene by SalI digestion. Targeted integration of the expression constructs into the HIS4 locus of the *P. pastoris* genome was achieved by electroporation of the SalI linearised vector into the histidine auxothrophic *P. pastoris* strain GS115 as described by [28]. For selection, *P pastoris* libraries were grown in histidine deficient minimal medium MD (1.34% yeast nitrogen base (YNB), $4\times10^{-5}$% biotin, 2% dextrose).

Induction of Surface Display

For surface display expression, *P. pastoris* yeast libraries selected on histidine-deficient medium for 72 hr were kept at 4° C. for a further 24 hr. The libraries were passaged on MD and an excess of at least 10-fold of the library size of freshly grown cells was grown at 30° C. in BMGY (1% yeast extract, 2% peptone, 1.34% yeast nitrogen base (YNB), 4×10−5% biotin, 1% (v/v) glycerol, 100 mM potassium phosphate, pH 6.0) for 24-48 hr. Surface display of the mutated domain 11 was induced by transfer to BMMY (1% yeast extract, 2% peptone, 1.34% YNB, 4×10−5% biotin, 0.5% (v/v) methanol, 100 mM potassium phosphate, pH 6.0). For maintained induction, cultures were supplemented with methanol to a concentration of 1% (v/v) every 24 hr for three days. Yeast cultures of control proteins (domain $11^{WT}$, domain $11^{AB3}$ and domain $11^{I1572A}$) were induced in the same manner.

FACS Screening Validation

Freshly induced yeast cells displaying domain $11^{WT}$, domain $11^{AB3}$ and domain $11^{I1572A}$ were pelleted and washed with PBSA (PBS+0.5% (v/v) BSA). Aliquots of $5\times10^5$ cells were incubated in PBSA for 1 hr at room temperature with anti-Flag M2 antibody (1:1000 dilution, Sigma) and increasing concentrations of biotinylated IGF2 ranging from 15 pM to 1.5 μM in a total volume such that a 10-fold molar excess of IGF2 over the domain 11 displayed on the surface was maintained (assuming a maximum of $5\times10^4$ molecules per cell) [29]. The cells were then pelleted, washed 3 times with cold PBSA and labelled with Alexa Fluor 488 goat anti-mouse IgG1 (Invitrogen) and Alexa Fluor® 647 streptavidin (Invitrogen) at 20 μg $mL^{-1}$ in a volume of 50 μL for 30 min at 4° C. Negative controls with secondary only and a positive control with anti-Flag+Alexa Fluor 488 only were also included. The cells were pelleted, washed 3 times with cold PBSA and resuspended in 1 mL of PBSA and run in CyAn ADP Cytometer (Dako). The yeast population was gated on forward- and side-scatter channels to remove debris and the percentage of double positive cells was measured for each IGF2 concentration.

FACS Library Screening

For the yeast loop libraries sorting, a 10-fold excess of the library population diversity was labelled in a similar manner, alongside the yeast cells displaying domain $11^{AB3}$. The cells were pelleted, washed with PBSA and incubated first with the Anti-Flag M2 antibody (0.76 μg/$10^6$ cells, Sigma) for 1 hr at room temperature followed by 3×PBSA washes. The subsequent incubation with 5 nM IGF2, maintaining a 10-fold molar excess of IGF2 over domain 11, was also carried out for 1 hr at room temperature. After 3×PBSA washes, the yeast cells were incubated with Alexa Fluor 488 goat anti-mouse IgG1 (0.02 μg/$10^6$ cells, Invitrogen) and Alexa Fluor® 647 streptavidin (2 μg/$10^6$ cells, Invitrogen) for 30 min-1 hr at 4° C. Negative and positive controls ($1\times10^6$ cells) were similarly labelled and used, together with the yeast cells displaying domain $11^{AB3}$ (also labelled with 5 nM IGF2), to gate the library yeast cells that should display higher affinity binders on the surface [29].

Biacore 3000 Screen

FACS gated cells were grown for 48 hr in YPD (1% yeast extract, 2% peptone, 2% dextrose) containing 100 U mL$^{-1}$ penicillin, 100 µg mL$^{-1}$ streptomycin, 100 µg mL$^{-1}$ kanamycin and 0.5 mg mL$^{-1}$ Geneticin. Genomic DNA was extracted using the YeaStar Genomic DNA kit (Zymoresearch). Mutated domain 11 was amplified by PCR from the genomic DNA using primers that incorporated EcoRI and AvrII restriction sites into the pPIC-HIS vector in frame with the α-factor secretion signal to generate pPIC-Domain 11 construct of the mutants [23]. The vector was then linearised with SalI and integrated into the HIS4 locus of the *P. pastoris* genome by electroporation [28]. Yeast cells incorporating domain 11 into their genome were selected at 30° C. on MD plates. Single yeast colonies were inoculated into 96 well plates containing 500 µl of BMGY and grown at 30° C. for 24 hr (covered with a sterile breathable seal). Each plate contained a set of controls, including non-transformed cells and cells secreting domain $11^{WT}$, domain $11^{AB3}$ and domain $11^{I1572A}$ mutants. The medium was replaced with BMMY and induction was sustained by supplementing with methanol to a final concentration of 1% (v/v) every 24 hr for two days.

100 µl of the supernatants, containing the secreted domain 11 mutants, were transferred to a 96 well plate, diluted with 100 µL of HBS-EP (10 mM HEPES pH 7.4, 150 mM NaCl, 3 mM EDTA, and 0.005% (v/v) surfactant P20) and screened for IGF2 binding ability by SPR on a Biacore 3000. Biotinylated IGF2 (GroPep, Aus) was immobilized on the flow cells of the sensor chip SA by affinity capture to streptavidin after pre-conditioning the sensor surface with three 1 min injections of 1 M NaCl, 50 mM NaOH. Kinetic experiments were performed at 25° C. in HBS-EP at a flow-rate of 40 µL min$^{-1}$ and consisted of a 2 min injection of diluted supernatant followed by a 2 min dissociation phase in HBS-EP running buffer, after which the binding surface was regenerated with a 2 min injection of 2M MgCl$_2$. The resulting sensorgrams were visually analysed using the standard BiaEvaluation software version 4.0.1 for Biacore 3000. Additionally, the dissociation phase was fitted to a first order exponential decay curve ($Y=Y_0 \cdot e^{-Kx}$) from which the 'off rate' (K) could be calculated.

Protein Expression and Purification of IGF2R Domain 11 Mutants for SPR Studies

For expression, yeast colonies selected on histidine-deficient plates were grown at 30° C. in 10 mL of BMGY for 24 hr and induced by being transferred to 50 mL BMMY. For maintained induction, cultures were supplemented with methanol to a final concentration of 1% (v/v) every 24 hr for two days. Supernatants were then subjected to SDS-PAGE and western blot using anti-His$_6$ mouse monoclonal antibody conjugated to peroxidase (Roche Diagnostics, USA). Domain 11 secreting cultures were scaled up to 500 mL BMMY and grown for further 72 hr and supplemented with 1% methanol every 24 hr. Supernatants were cleared by centrifugation (6000 rpm for 20 min at 4° C. in a Beckman-Coulter Avanti-J2 refrigerated centrifuge), diluted 5-fold in 20 mM sodium phosphate pH 8.0 buffer and His-purified using a Ni-NTA superflow column (Qiagen) on an Äkta FPLC system (GE Life Sciences, UK) washed with 20 mM imidazole and eluted with 250 mM imidazole. The fractions containing the protein were pooled and, when required, diluted in 20 mM MES pH 6.0 and purified using a Resource S column on an Äkta FPLC system (GE Life Sciences, UK). Purified proteins were dialyzed and concentrated using centrifugal filter units of 5 kDa cut-off (Millipore). Protein concentration was determined spectrophotometrically (Nanodrop) using the theoretical extinction coefficient calculated by ProtParam and protein size and homogeneity was verified using 12% SDS-PAGE.

Structure-Informed Loop-Specific Site Directed Mutagenesis

The domain $11^{AB3}$:IGF2 structure (PDB: 2L29) was used to identify residues in the binding loops that could interact with IGF2. These were manually mutated in Pymol v1.5 to determine whether or not they might stabilise the complex. In addition the Robetta server was used to perform interface alanine scanning mutagenesis on the Domain $11^{AB3}$ complex to identify residues important for complex formation. A number of possible amino acids were introduced at each site to assess the residue's role in binding. M6P/IGF2R domain 11 sub-cloned from the pPICHis vector into pET26a (Novagen, Merck Chemicals Ltd, Nottingham, UK) was used as a template for site directed mutagenesis. The template was amplified in a thermocycler (PeqStar) using mutagenic primers and KOD DNA polymerase (Novagen) to introduce the mutations. Following amplification the parental DNA was digested with DpnI and transformed into *E. coli* 5α cells (NEB) for sequencing. The mutant proteins were expressed and refolded using existing protocols in *E. coli* BL21 (DE3) before the binding kinetics were analysed by SPR[3].

Protein Expression and Purification of Domain 11 Mutants for NMR Studies.

For NMR studies, domain $11^{AB5}$ was sub-cloned from the pPICHis vector into pET26a (Novagen, Merck Chemicals Ltd, Nottingham, UK) for expression in *E. coli* BL21 (DE3). The proteins were refolded using existing protocols and purified by gel filtration [3]. Uniformly $^{13}$C, $^{15}$N-labelled proteins were expressed in *E. coli* BL21 (DE3) grown in minimal media containing $^{15}$NH$_4$Cl and $^{13}$C glucose as the sole sources of carbon and nitrogen.

Expression and Purification of Domain $11^{WT}$, Domain $11^{AB5}$ and IGF2-Domain $11^{AB5}$ Complexes for NMR His$_6$-tagged domain $11^{WT}$ and domain $11^{AB5}$ (residues 1508-1654) cloned into pET26 (Novagen, Merck Chemicals Ltd, Nottingham, UK) were transformed into *E. coli* BL21 (DE3) CodonPlusm competent cells, purified as inclusion bodies and refolded according to well-established protocols [3]. Proteins were isotopically labelled using 1 g L$^{-1}$ $^{15}$N-ammonium chloride and/or 2 g L$^{-1}$ $^{13}$C$_6$-glucose (99%, Cambridge Isotope Laboratories) in M9 minimal media. Lyophilised unlabelled IGF2 obtained from Novozymes Biopharma, AU, was added to NMR samples of $^{15}$N-single (dynamics studies) and $^{15}$N, $^{13}$C-double labelled domain $11^{AB5}$ mutant (structural studies) in a 1:1 ratio at pH 4, which provided optimum stability for the complex. Structural calculations of the domain $11^{AB5}$ both free and complexed with IGF2 were as described for the domain $11^{AB3}$:IGF2 complex [3]. Validation was performed using the icing online server (version r76). The ensembles of NMR structures and associated NMR chemical shifts have been deposited with the protein database and BioMagResBank with the following accession codes: Free domain $11^{AB5}$ 2M6T and rcsb103281, IGF2 bound domain $11^{AB5}$, 2M68 and rcsb103260.

NMR Dynamics Studies

NOE, $^{15}$N-T$_1$ and $^{15}$N-T$_2$ NMR relaxation data were acquired at two fields (600 and 900 MHz) at 25° C. on a Varian VNMRS or INOVA spectrometer respectively, both fitted with cryogenically cooled probe heads for domain $11^{WT}$ and domain $11^{AB5}$. T$_1$ delays of 0.01, 0.02*, 0.03, 0.05, 0.07, 0.10, 0.15, 0.30, 0.40, 0.6, 0.8, 1.0, 1.5, 2.0 and 2.5 s (*600 MHz only, **900 MHz only) and T2 delays of 0.1-2.1 s with intervals of 0.2 s were gathered using BioPack pulse sequences provided by VnmrJ 2.2. $T_1$ and $T_2$ experiments were run in duplicate. Automatic spectral compression (ASCOM) [30] was applied to increase signal:noise without increasing the length of the experiments. NOE ratios were calculated between peak heights in HSQC spectra recorded both with and without NOE proton saturation. At the beginning of each transient a 5 s ultra-low power pulse was employed for those spectra without NOE and a 3 s proton saturation pulse with a 2 s delay (total 5 s) for those experiments with NOE. Data collected was processed (NMRPipe, [31]) and assigned (Analysis 2.1.5 [32]) before being exported for curve fitting and model free analysis (relax 1.3.9 [33, 34]. Relaxation rates were calculated by an eleven parameter grid search, followed by simplex minimisation curve fitting to a two-parameter ($I_0$, $R_x$) exponential decay. Monte Carlo error analysis used the standard deviation of simulated curves back calculated from fitted parameters across replicated spectra or from the Sparky 3.113 (Goddard T. D.). RMSD calculation of noise in a peak-free region of non-replicated spectra. Relaxation datasets recorded at 600 and 900 MHz were validated using self-consistency tests within relax. Extended model free analysis [35-37] was performed within relax 1.3.9 which involved AIC model-free model selection [38] and elimination of failed models followed by Monte Carlo simulations [39]. After initial calculation of local $\tau_m$ values, isotropic (sphere) and anisotropic (prolate/oblate spheroids, ellipsoid) diffusion models were optimised followed by AIC selection of the best model.

Surface Plasmon Resonance (SPR) and Binding Analysis

Final kinetic analysis of mutants by SPR was conducted using a Biacore T200 biosensor at 25° C. in either HBS-EP (10 mM HEPES pH 7.4, 150 mM NaCl, 3 mM EDTA, and 0.005% (v/v) surfactant P20) or MES-EP (20 mM MES pH 6.5, 150 mM NaCl, 3 mM EDTA, and 0.005% (v/v) surfactant P20) at a flow-rate of 40 µL min$^{-1}$. For analysis of the domain 11:IGF2 interaction, approximately 20-50 RU of biotinylated IGF2 (GroPep, Aus) or IGF1 were immobilized on each flow cell of a CM5 chip by affinity capture to streptavidin and recombinant domain 11 at concentrations ranging from 64 nM to 0.125 nM was injected. For the analysis of the Fc-domain $11^{AB5}$ interaction, approximately 50 RU of a biotinylated IGF2:biotinylated ubiquitin mixture (1:8 proportion) was immobilized on the CM5-streptavidin chip. This interaction was also analysed by immobilizing the Fc-domain $11^{AB5}$ and Fc-domain $11^{AB5-RHH}$ (or Fc-domain $11^{I1572A}$ as control) by Human Antibody Capture (monoclonal mouse anti-human IgG antibody immobilised on a CM5 chip by amine coupling, GE Healthcare) with and without human IgG1 Fc fragment (Bethyl Laboratories, UK) in the control flow cell. Increasing concentrations of IGF2$^{1-67}$, proIGF2$^{1-104}$, proIGF2$^{1-156}$ and IGF1 ranging from 0.125 to 32 nM were injected. T200 BiaEvaluation software (GE Healthcare) was used to fit the resulting curves according to a 1:1 binding model. Steady state affinities were determined using the kinetic data, taking the response average at 5 seconds before injection end and for 5 seconds average. Thermodynamic data was performed across the temperature range of 10° C. to 30° C., van't Hoff and Erying plots generated and ΔH, −TΔS and ΔG values determined as previously described[23].

Fc-Fusion Protein Expression and Purification

Fc-domain $11^{AB5}$ fusion protein was cloned as previously described [40], produced by transient transfection of HEK293T cells with pHLSec-AB5-hIgG1 and utilising Corning Cellstack10's to scale-up cell culture. Purified Fc-domain $11^{AB5}$ was analysed for the presence of aggregates by chemical crosslinking with bis[sulfosuccinimidyl] suberate (BS3). 100-200 ng of concentrated Fc-domain $11^{AB5}$ was diluted into PBS and incubated in the presence or absence of 0.5 mM BS3 for 30 min at room temperature. The reaction was quenched by the addition of SDS-PAGE sample buffer and samples were analysed by SDS-PAGE and western blotting using an anti-IGF2 antibody (AF-292, R&D). For bulk production in Chinese Hamster Ovary cells GS knockout (CHOK1SV GS-KO cells, Lonza Biologics, PLC), three IgG2 Fc-fusion constructs were first transiently expressed, Fc-domain 7-13$^{T926-P1189}$, Fc-domain $11^{AB5-RHH}$, and a tandem construct of domain $11^{AB5-RHH}$. Prior evaluation of in silico antigenicity utilised Epibase™ HLA class II allotypes against amino acid sequences of Fc constructs, including linkers, showed that domain $11^{AB5}$ was less antigenic and so was selected for bulk production. Bulk cultures from stable selected CHOK1SV GS-KO resulted in protein A affinity purified yields in the range of 27 to 187 mg/L. SDS-Page and size exclusion HPLC confirmed a single Fc product with endotoxin levels <0.74 EU/mg. For Fc-domain $11^{AB5}$:IGF2 co-precipitation, an aliquot of 400 µL of media of cells treated with Fc-domain $11^{AB5}$ or Fc-domain $11^{I1572A}$ or a previously incubated mixture of recombinant IGF2 and Fc-domain $11^{AB5}$ was incubated overnight at 4° C. with Protein A/G Agarose (Immunoprecipitation, Protein A, Roche). Agarose beads were washed according to the manufacturer's instructions, resuspended in 2× sample buffer, boiled and the supernatant used for western blot analysis as described below.

Fc-Domain $11^{AB5}$:IGF2 Co-Precipitation

An aliquot of 400 µL of media of cells treated with Fc-domain $11^{AB5}$ or Fc-domain $11^{I1572A}$ or a previously incubated mixture of proIGF2 and Fc-domain $11^{AB5}$ was incubated overnight at 4° C. with Protein A/G Agarose (Immunoprecipitation kit (Protein A), Roche). Agarose beads were washed according to the manufacturer's instructions, resuspended in 2× sample buffer, boiled and the supernatant used for western blot analysis as described previously.

IGF2 Induced Hypoglycaemia

All animal experiments were approved by the animal use ethical committee of Oxford University and fully complied with UK Home Office guidelines (PPL 30/2695). Wild-type C57BL/6J and 129S2 mice were used throughout. Mice were anaesthetised using a rising concentration of isoflurane in oxygenated air and maintained using 2% isoflurane with 2 L min$^{-1}$ oxygen. Blood glucose measurements were taken using an Advantage diabetic glucose meter (Roche Diagnostics, Burgess Hill, UK). In order to test the direct inhibition of IGF2-induced hypoglycaemia by Fc-domain $11^{AB5}$, blood glucose levels were allowed to normalise for 30 min prior to taking a baseline blood glucose reading, then either 1 mg kg$^{-1}$ IGF2 only (R&D systems), or 1 mg kg$^{-1}$ IGF2 premixed with 11.7 mg kg$^{-1}$ Fc-domain $11^{AB5}$, Fc-domain $11^{RHH}$, or Fc-domain $11^{I1572A}$ (1:1 molar ratio) was injected. Blood glucose measurements were taken every 10 min for the following hour. For the Fc-domain $11^{AB5}$ mouse preloading experiment, 11.7 mg kg$^{-1}$ Fc-domain $11^{AB5}$ or PBS, as negative control, was injected immediately after induction of anaesthesia, 30 mins later a baseline blood glucose reading was taken and 1 mg kg$^{-1}$ IGF2 (1:1 molar ratio) was injected, readings were then taken every 10 min for the following hour. For the mouse IGF2 preloading experiment, 1 mg kg$^{-1}$ IGF2 was injected immediately after induction of anaesthesia, 30 min later a baseline blood glucose reading was taken and either 11.7 mg kg$^{-1}$ Fc-domain 11$^{AB5}$ (1:1 molar ratio) or PBS was injected, readings were then taken every 10 min for the following hour.

In Vitro Cell Viability

The human hepatocellular carcinoma cell lines Hep 3B2.1-7 and Huh-7D12 were obtained from the ATCC (HB-8065) and the ECACC (Catalogue number 1042712), respectively. Hep 3B2.1-7 was grown in EMEM (Lonza) supplemented with 10% (v/v) fetal bovine serum, 100 U mL-1 penicillin, 100 µg mL-1 streptomycin, and 2 mM Lglutamine Huh-7D12 was grown in DMEM (Sigma) supplemented with 10% fetal bovine serum, 100 U mL-1 penicillin, 100 µg mL-1 streptomycin, and 2 mM L-glutamine. Cells were plated in 96-well plates at a density of 1-2×10$^4$ cells/well in serum free medium. After 24 hr, Fc-domain 11$^{AB5}$ (orange), Fc-domain 11$^{J1572A}$ as negative control (grey) or OSI-906 (purple) were added to each well to different final concentrations and the cells were incubated for further 48-72 hr. Cell viability was assayed at 48 and 72 hr after Fc-domain 11$^{AB5}$ treatment using the CellTiter 96® AQueous Non-Radioactive Cell Proliferation Assay (Promega). The half maximal inhibitory concentration (IC50) was calculated using graph prism.

Cell Proliferation Assay

EdU incorporation was used to measure cell proliferation (Invitrogen, C10338). Briefly, cells were plated at a density of 2×105 cells/well in 6-well plates and cultured in serum free media. After 24 hr of serum starvation, PBS (black) and 1.5 µM Fc-domain 11$^{J1572}$ (grey) as negative controls, 0.5 and 1.5 µM Fc-domain 11$^{AB5}$ (orange), 1 µM OSI-906 (purple) and 0.1 and 0.5 µM doxycycline (green) as positive controls were added to the different wells and cells were further cultured. After 48 hr, 10 µM EdU was added for 3 hr and cells were then washed and trypsinised, followed by fixation in 4% PFA and permeabilisation in TBS/5% Triton. The Alexa 555 dye was then attached to the EdU molecules by click chemistry following the manufacturer's instructions and the % of EdU incorporation under different conditions was then analysed by flow cytometry.

IGF2 Dependent Human Cancer Cell Xenografts

IGF2 sensitive autocrine cell line SKNMC-IGF2[67] was generated from the Ewing sarcoma cell line SKNMC by retroviral infection with constructs containing IRES-luciferase. Autocrine growth and signalling function of the SKNMC line, including inhibition by IGF2-TRAP, was confirmed in culture using an MTS reagent (Cell Titer 96 Aqueous One Solution cell proliferation assay, Promega). For xenografts, approximately 5×10$^6$ SKNMC-IGF2[67] cells harvested during the growth phase of sub-confluent cell cultures were then mixed with matrigel (50:50 v/v, 100 µl/mouse) and injected (sub-cutaneous) into CD-1® (Crl: NU-1 Foxn1nu) female mice, 24 hours after establishing ALZET® mini-pump placement delivering a single concentration 40 mg kg-1 per week either IGF2-TRAP or PBS vehicle control. Tumour growth was monitored with both caliper measurements and bioluminescence. The latter was performed with a Bruker Xtreme 2D optical system 15 minutes (10 second exposure) following luciferin injection (100 µl per 20 g body weight). Tumours were excised at 28 days or when size was >1000 mm3. Fixation in formalin, embedding in paraffin and Hematoxylin and Eosin (H&E) staining was done using standard protocols. Apoptotic area was quantified using automated image analysis of brightfield images in ImageJ, applying H AEC color deconvolution filter and automated thresholding. Serum was also collected at the time of culling.

IGF2-TRAP Synthetic Lethality Screen

For synthetic lethality screens (Target Discovery Institute, University of Oxford), either 2,500 or 5,000 SKNMC-IGF2104-IRES-luc cells were plated in medium containing 0.5% charcoal stripped FBS in 384 well plates and the IGF2-TRAP was added 24 h later to half of the plates. Using automated dispensing 307 oncology drugs that have been tested in man (TDI expanded Oncology Drug library) were added to cells 3 hrs later 10 µM, 1 µM, 100 nM and 10 nM, in the presence and absence of 250 nM IGF2-TRAP. After 48 hr of incubation, resazurin was added to a final concentration of 10 µg/mL and the fluorescence (Ex: 560 nm, Em: 590 nm) recorded at 2 hr. Normalisation was performed with untreated cells and cells treated with the fixed concentration of IGF2-TRAP alone. Pearson's product-moment correlation coefficient (r) was calculated to determine replicate correlation. For hit selection, we used a bespoke 'interaction score' metric (a variation on standard Δz-score analysis) followed by hit selection using the robust non-parametric Rank Product method.

The interaction score was calculated where v was the viability readout for the drug condition, $x^-$ was the sample mean of the negative controls and s was the sample standard deviation of the negative controls, z was calculated as z_treatment=(v−$x^-$)/s. z_(no_IT) was calculated from PBS control plates, comparing 'drug d' to same-plate negative controls 'cells+DMSO'. z_IT was calculated from treated plates, comparing 'drug d+IGF2-TRAP (IT)' to same-plate negative controls 'cells+IT+DMSO'. The magnitude of these z-scores reflects the degree of inhibition of cell viability by 'drug d±IT' relative to negative controls, also taking into account well-to-well variation. The interaction score is defined as z_(no_LT)−z_IT. Thus, a more negative interaction score represents a greater synergistic lethal effect: the inhibitory effect of the drug is potentiated by IT. Interaction scores were calculated for each replicate r_(d,1)/r_(d,2)/r_(d,3) independently. The rank product was calculated in each data set (16 data sets: cell density×drug library concentration×rezasurin incubation time) each replicate for each drug was ranked independently, with 1st rank assigned to the most negative interaction score. Using these ranks, a Rank Product RP(d) for drug d in each data set was calculated, where r_(d,i) is the rank of the ith replicate for drug d:

$$RP(d) = \sqrt[3]{((r\_(d, 1))(r\_(d, 2))(r\_(d, 3)))}$$

In a permutation test, the RP for each drug is compared to a simulated data set giving an estimated p-value of false positive. These p values, in the context of our experiment, informed us about effect size, direction and reliability, and allowed us to control the false discovery rate in contrast to many other hit selection protocols 43. Hits were selected where p<0.05.

For synthetic lethality hit validation, fresh stocks of the four drugs selected as hits were obtained (pictilisib, SYN-kinase and PF-04691502, Cayman Chemical). The interaction of the selected drugs and IGF2-TRAP were evaluated by Q-value calculated by the formula Q=FD+T/FD+(1−FD) FT, where FD+T represents the fraction affected by treatment with the drug plus IGF2-TRAP compared with the untreated control group, FD represents the fraction affected by the drug alone, and FT represents the fraction affected by the IGF2-TRAP alone. A value of Q>1.15 indicates a synergistic effect, Q<0.85 indicates an antagonistic effect, and Q between 0.85 and 1.15 indicates an additive effect [54].

Cell Assays, Protein Extraction and Immunoblotting

For analysis of IGF2 secretion by the different cell lines, cells were plated in 6-well plates in serum-free medium at a concentration of approximately 106 cells per well. The medium was collected after 48 hr, spun at 4000 g for 20 min and the supernatant filtered through a 0.22 μm filter. For signaling analysis, cells were plated in 6-well plates at a concentration of approximately 3-6×105 cells per well in serum-free medium. After 24 hr, Fc-domain $11^{AB5/AB5\text{-}RHH}$ (or PBS and Fc-domain $11^{I1572A}$ as negative controls) were added to each well to the corresponding concentration and the cells were incubated for further 48-72 hr. Cells were washed with PBS and lysed on ice in RIPA buffer (50 mM Tris HCl pH 8, 150 mM NaCl, 1% NP-40, 0.5% sodium deoxycholate, 0.1% SDS) containing protease and phosphatase inhibitors (Halt cocktail, Pierce). Lysates were cleared by centrifugation at 4° C. Protein levels were quantified using the CB-X assay (G-Biosciences) as per manufacturer's instructions. SDS-PAGE gel electrophoresis and protein transfer of either 20 μg of protein or 5 μL of serum were done following standard protocols. Antibodies used were anti hIGF2 (R&D Systems AF-292, 2 μg mL-1), anti pAktS473 (Cell Signaling 4060, 1:1000), anti β-actin (Ab-Cam 8227, 1:20000), anti pIGF1RY1135/1136/pIRY1150/1151 (Cell Signaling 3024, 1:1000), CaptureSelect Biotin Anti-hIgG-Fc (Life Technologies, 1:1000), anti mIGF1 (R&D Systems AF-791, 1 μg mL-1), anti mIGFBP2 (Millipore 06-107, 1/1000 dilution), anti mIGFBP3 (R&D Systems MAB775, 1 μg mL-1), anti mIGFBP5 (R&D Systems AF578, 0.1 μg mL-1), anti mIGFBP6 (R&D Systems AF776, 0.1 μg mL-1), anti mGH (R&D Systems BAF1566, 0.5 μg mL-1), anti hIGFBP3 (Santa Cruz Biotechnology Sc-9028, 1 μg mL-1), anti hALS (Novus Biologicals NBP1-89118, 1 μg mL-1). Secondary antibodies were from Dako, used at 1:2000, except Streptavidin HRP at 1:4000 (Thermo Scientific Pierce). Densitometry was performed using ImageJ (NIH) and was normalized to actin.

Results

M6P/IGF2R domain 11 has been previously expressed using *P. pastoris* to generate stable soluble protein suitable for surface plasmon resonance (SPR) and isothermal calorimetry (ITC) [23]. A yeast surface display system was adapted using the Agα1 system in *P. pastoris* [41]. By expressing an N-terminal flag-tagged domain 11, we measured the cell surface expression of the domain with anti-flag antibody and Alexa 488 labelled secondary antibody. Following incubation of live yeast expressing domain 11 with biotinylated human $IGF2^{1-67}$, IGF2 binding was quantified with Alexa647 labelled streptavidin. When incubated with a range of IGF2 concentrations, the system was sensitive enough to discriminate different affinities for domain $11^{WT}$, domain $11^{AB3}$ and a non-binding mutant domain $11^{I1572A}$. Yeast induced to express mutant domain 11s underwent flow sorting to select high affinity IGF2 binders to a low concentration of IGF2 (5 nM). Gates were set based on the binding of IGF2 to domain $11^{WT}$ and domain $11^{I1572A}$ (reduced binding mutant), prior to setting thresholds using domain $11^{E1544K}$ or domain $11^{AB3}$ (higher IGF2 affinity) [23]. Selected live yeast were cultured, mutant domain 11s sub-cloned in a soluble protein expression vector, cells plated and single selected clones screened in a 96 well format using a Biacore 3000 and $k_{off}$ ($y=Y_0 \cdot e^{-k_{off}x}$) determination. Yeast expressing soluble mutant $his_6$-domain 11s with slow $k_{off}$ were expanded and purified prior to real time kinetic quantification using a sensitive Biacore T200.

Screens of the AB loop ($^{1542}$YSKKGL$^{1547}$) library including the E1544K mutation led to the identification of a mutant (AB5) with ten-fold higher IGF2 affinity compared to domain $11^{WT}$ ($K_D$ 5.07 nM vs 46-64 nM, Table 1). Sequencing of clone AB5 identified the presence of five AB loop mutations ($^{1542}$YAKGWG$^{1547}$) compared to the three mutations of domain $11^{AB3}$ ($^{1542}$YSKSGV$^{1547}$) relative to wild-type domain 11 ($^{1542}$YSEKGL$^{1547}$). Of the mutants characterized, domain $11^{AB5}$ was the highest IGF2 affinity AB loop mutant that retained IGF2 specificity with respect to IGF1.

To determine how the mutations incorporated into domain $11^{AB5}$ altered the IGF2 binding site, high-resolution NMR structures of domain $11^{AB5}$, both in the free form and in complex with IGF2 were then solved. $^{15}$N-relaxation data for domain $11^{WT}$ and domain $11^{AB5}$ was also recorded at two field strengths (600 and 900 MHz). Domain $11^{AB5}$ showed the characteristic flattened β-barrel domain 11 fold and was well defined over this core secondary structure (RMSD=0.55 Å). All the hydrophobic residues in the binding site, including foundation residues, are conserved between domain $11^{WT,\ E1544K,\ AB3}$ and $^{AB5}$[3]. The hydrophobic residues (Y1542, F1567, I1572, Y1606, L1629 and the hydrophobic portion of K1631) and the foundation residues (V1574, L1626 and L1636) create a complementary binding surface for IGF2 and mutation of these residues reduces or abrogates IGF2 binding [23]. Despite these observations, the AB loop adopts a dramatically different structure in domain $11^{AB5}$. W1546, which substitutes for a G1546, has the aromatic side-chain rotated to pack into and extend the hydrophobic patch. The bulky tryptophan side chain causes a reorientation of adjacent residues within the binding site, forcing the displacement of Y1542 and F1567 on the AB and CD loops, respectively, and projecting the remainder of the AB loop between Y1542 and W1546 back away from the IGF2 binding region. In both the domain $11^{WT}$ and domain $11^{AB3}$ structures, this portion of AB is more closely associated with the hydrophobic patch, with the small G1546 side chain allowing facile rearrangement and conformational flexibility in both the AB loop and the neighbouring Y1542 and F1567. Globally, when compared to domain $11^{WT}$, accommodation of the tryptophan residue in domain $11^{AB5}$ displaces the β-A strand and causes a displacement of the GH-loop (at the opposite end of the protein) and the C-terminal α-helical turn.

Upon complex formation, the AB loop was observed to shift in domain $11^{AB3}$ to accommodate IGF2, whereas there is almost no rearrangement of the AB loop in domain $11^{AB5}$ as this superimposes closely with the bound form. The re-organisation in domain $11^{AB5}$, while allowing the original hydrophobic residues to contact IGF2, would also favour the interaction of W1546 with F19, the most important residue for the docking of IGF2 to domain 11 [3, 22]. The bulky side-chain of W1546 causes a reorientation of residues within the binding site, forcing the displacement of Y1542 and F1567 on the AB and CD loops, respectively while still allowing them to contact F19 of IGF2. Increased interaction via aromatic ring-stacking between Y1542, W1546 and F1567 also causes an overall increase in rigidity in domain $11^{AB5}$ in comparison to the more flexible domain $11^{WT}$, shown by an increase in $S^2$ and a decrease in $R_{ex}$ in the AB, BC and CD loops of domain $11^{AB5}$. The loss of flexibility stabilises the binding site of domain 11, providing a stable platform for the docking of IGF2. In addition to the five hydrophobic binding site residues of wild-type domain 11, there are also charged and polar residues that interact with IGF2. These are found among the more flexible regions of all four binding loops. The surface of IGF2 is negatively charged overall, and residue E1544 in human domain $11^{WT}$ is the only acidic residue in the binding site. Mutation from a negative to a positive charge at this position forms a salt bridge with D23 and therefore plays a major part in increasing binding affinity to IGF2. In domain $11^{AB3}$ the additional K1545S mutation may have also contributed to increased binding affinity since a hydrogen bond could be formed between Q18 of IGF2 and the hydroxyl group of the serine. In domain $11^{AB5}$, however, K1545G would be incapable of forming a hydrogen bond with Q18, implicating structural importance of the G1546W mutation for the gain in affinity.

We next looked at structural data for residues in the binding loops that could interact with IGF2, and mutated these in Pymol to predict whether or not they might stabilise the complex. In addition the Robetta server was used to perform interface alanine scanning mutagenesis on the AB3 complex to identify residues important for complex formation. These additional mutations and SPR affinity are shown in Table 1 and FIG. 1. Introduction of W1546F into the AB loop reduced the $k_{off}$ by two fold, yet retained the similar overall $K_D$ (4.35 nM) as a result of a reduced $k_{on}$. Mutations of FG loop residues P1599, 51600, and L1604 failed to enhance affinity, but K1601R, S1602H, S1602Q and G1603K all exhibited up to 2-fold improvement. Interestingly, S1602H, S1602N and G1603K all reduced $k_{off}$, suggesting that AB loop and FG loop mutants may also function in combination. Introduction of structurally predicted site directed mutations in the HI loop slightly improved affinity, although a number of single point mutations could be introduced that appeared to slow the $k_{off}$, such as Q1632A ($K_D$=3.76 nM) and K1631W ($K_D$=3.23 nM).

The affinity of IGF2 for domain $11^{AB5}$ was at least two fold higher than our highest previously detected mutant, and we had already detected functionally additive single point mutations of the FG and HI loops that enhanced domain $11^{AB5}$ affinity. We then systematically determined the potential for the HI loop to specifically stabilise the IGF2 binding interaction by introducing a library of mutants for four residues of the HI loop ($^{1630}$DKQT$^{1633}$) into domain $11^{WT}$, rather than domain $11^{AB5}$, leading to a predicted $1\times10^5$ fully representative clones of every possible amino acid combination. By validating flow sorting gates with domain $11^{AB3}$, we sub-cloned $2.2\times10^5$ flow sorted mutants with high binding to IGF2 into a soluble expression system. We purified soluble proteins and screened over >1000 clones (Table 3). One mutant amongst several false positives was identified ($^{1630}$HFQS$^{1633}$) with slower $k_{off}$ than domain $11^{WT}$ (Table 2). The majority of false positives also indicated that introducing a more specific kinetic screen with the T200 platform using purified recombinant protein was required.

In parallel we screened a domain $11^{AB3}$ cultures and obtained clones from a control culture with slow $k_{off}$ to IGF2 binding. Expressed proteins confirmed a number of mutants that bound IGF2 with apparent high affinity (Table 3). In particular, a four-fold reduction in $k_{off}$ was detected with the FG loop mutant, P1597H that was also associated with a ten-fold reduction in affinity compared to domain $11^{AB3}$ ($K_D$=1.23 nM vs 15.3 nM, respectively). Similarly, a two-fold reduction in $k_{off}$ was detected with P1597K that was also associated with a six-fold reduction in affinity compared to domain $11^{AB3}$ ($K_D$=2.78 nM vs 15.3 nM, respectively). Moreover, we unexpectedly detected a mutant in the hydrophobic CD loop (Q1569R) that had enhanced affinity ($K_D$=2.30 nM). This was a notable observation because of the known importance of hydrophobicity and shape complementarity of the CD loop component during evolution of the binding site [3], even though we knew that Q1569A had little impact on IGF2 affinity [23]. As a result of the combined structural predictions and directed evolution approaches described, we had evolved domain 11 with respect to higher IGF2 affinity in vitro with several novel and independent AB, CD, FG and HI loop mutants. Moreover, these specific mutations in CD, FG and HI loops, on either domain $11^{AB5}$ or domain $11^{AB3}$ AB loop backgrounds, modified the $k_{off}$ and overall affinity (FIG. 1 and Tables 1 and 3).

We next sought to determine whether individual loop mutations, identified on different AB loop mutagenic backgrounds, could be combined to either generate additive, subtractive or synergistic binding affinities and specificity for IGF2. In particular, CD loop (Q1596R), FG loop (P1597H/K, S1602H, G1603K) and HI (K1631W, $^{1630}$HFQS$^{1633}$) loop mutations appeared to each enhance affinity, with retained specificity for IGF2, and were selected as potential candidates to combine. Successive additions of the majority of mutations resulting in combinations of CD and FG mutations, additively improved the binding kinetics on either a domain $11^{AB3}$ or domain $11^{AB5}$ background (FIG. 2, 3 and Table 3).

The thermodynamic parameters for the domain 11-IGF2 interaction were obtained from the temperature dependence of the dissociation constant according to the van't Hoff equation for domain $11^{WT}$, AB loop mutants (domain $11^{AB3}$ and domain $11^{AB5}$), double loop mutants (domain $11^{AB5\ Q1569R}$ (AB+CD loops) and domain $11^{AB5\ P1597H\ S1602H}$ (AB+FG loops) and the triple loop mutant domain $11^{AB5\ Q1569R\ P1597H\ S1602H}$ [23, 42]. The interaction of IGF2 with domain $11^{WT}$ appeared driven by enthalpy ($\Delta H<0$), with a relatively unfavourable entropic contribution ($-T\Delta S>0$) (FIG. 4). Mutations in the AB loop appeared to have different effects. Domain $11^{AB5}$ retained the same thermodynamic profile as domain $11^{WT}$, whereas in domain $11^{AB3}$, the entropic contribution appeared more favourable as we had previously shown for the E1544K AB loop mutant [23]. Addition of mutations in domain $11^{AB5}$ CD or FG loops introduced more favourable changes in the entropic contribution and $k_{off}$ similar to domain $11^{AB3}$ (FIG. 4, 5). The CD loop mutation in domain $11^{AB5\ Q1569R}$ was the only mutant tested with both improvement in both enthalpy and entropy terms compared to domain $11^{WT}$. Moreover, introduction of mutations in FG loop appeared to generate a clearer contribution of entropy to the improved affinity, as both energetic terms contribute favourably to the free energy of binding of domain $11^{AB5\ P1597H\ S1602H}$ and of the triple loop mutant domain $11^{AB5\ Q1569R\ P1597H\ S1602H}$.

In the combined mutants, additive rather than synergistic effects were detected (FIG. 3). It was possible that combining loop mutants in a single domain might also disrupt of protein folding, attributed to epistatic interactions that modify the successful accommodation of additional mutations into stable folded protein. For example, addition of HI loop K1631W and $^{1630}$HFQS$^{1633}$ to the combined loop mutants, all failed to result in stable expressed protein, implicating a probable effect on protein folding on both domain $11^{AB3}$ and domain $11^{AB5}$ backgrounds. Introduction of multiple mutations (9 to 11) into domain $11^{AB5}$ appeared less tolerated in terms of protein yields, than similar mutations in domain $11^{AB3}$, potentially implicating the structural configuration adopted by the effect of W1546 in domain $11^{AB5}$ on protein folding of other loop mutants (Table 3). Four higher affinity IGF2 super-antagonists were identified.

For mutants on a domain $11^{AB5}$ background, the high affinity mutants appeared relatively independent of pH (domain $$11^{AB5(1542Y\underline{AKGWG}1547)\ Q1569R\ P1597H\ S1602H}$$

$K_D$=0.65 nM pH 7.4/=0.71 nM pH 6.5, domain $$11^{AB5(1542Y\underline{AKGWG}1547)\ Q1569R\ P1597H\ G1603K}$$

Figure 13:
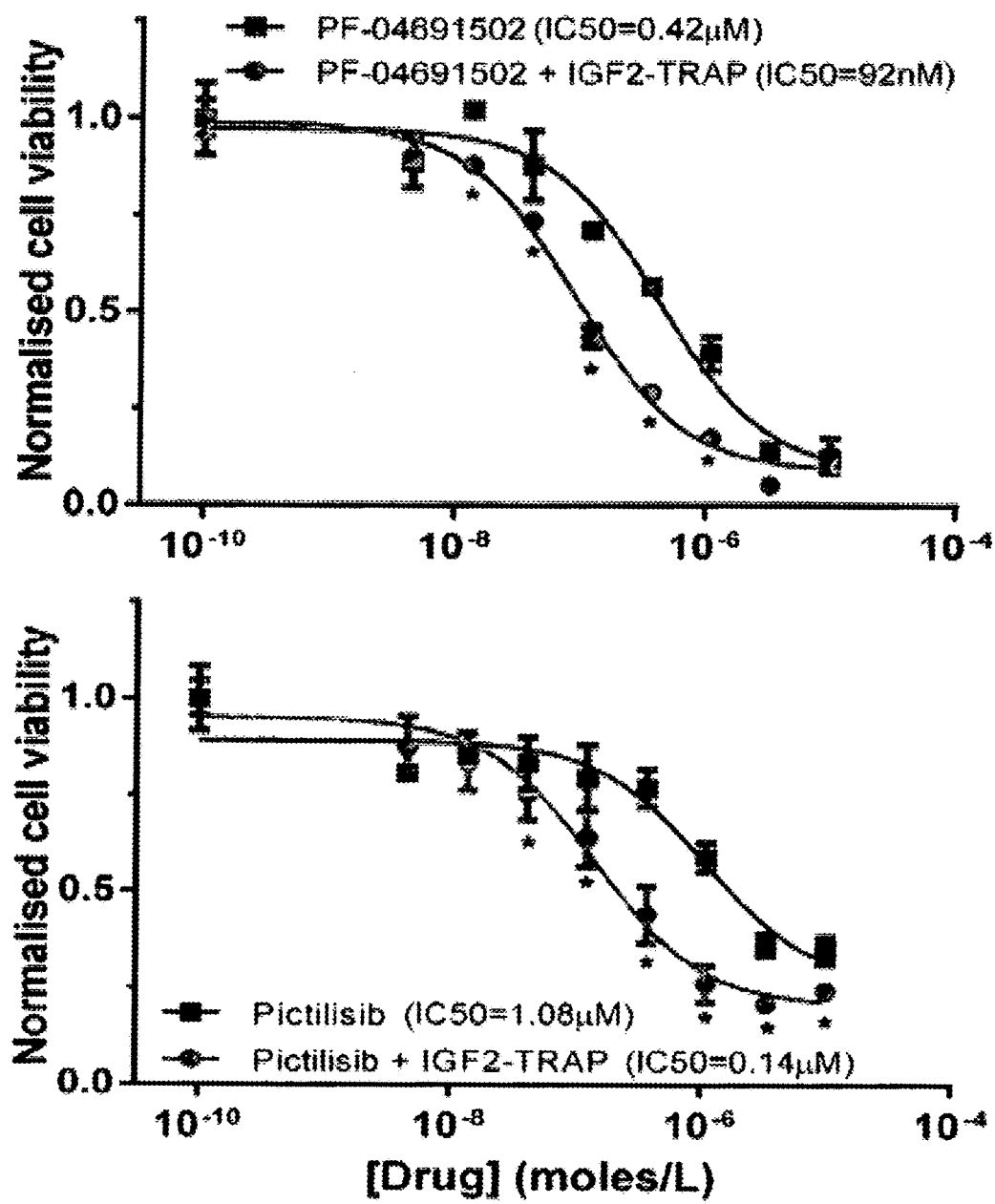
FIG. 13 shows IGF2-TRAP synergistic screening validation dose response curves for PI3 kinase inhibitors (PF-04691502 and Pictilisib) in the presence (light grey line) and absence (dark grey line) of the IGF2-TRAP in Ewing sarcoma cell line (SKNMC). IC50 values are shown. Leftward shift indicates synergism (P<0.0001 when comparing the IC50 of drug alone vs. drug+IGF2-TRAP using the F-test). Asterisks indicate the concentrations at which there are synergistic interactions (Q>1.15).

$K_D$=0.87 nM pH 7.4/=0.69 nM pH 6.5). For domain $11^{AB3}$, lower pH (Table 4) enhanced affinity of both mutants due to slower $k_{off}$ (domain $$11^{AB3(1542YS\underline{KS}G\underline{V}1547)\ Q1569R\ P1597H\ S1602H}$$

$K_D$=0.74 nM pH 7.4/=0.40 nM pH 6.5, domain $$11^{AB3(1542YS\underline{KS}G\underline{V}1547)\ Q1569R\ P1597H\ S1602H\ G1603K}$$

$K_D$=0.78 nM pH 7.4/=0.43 nM pH 6.5), such that there a 100 fold improved overall affinity of mutant domain 11 with retained IGF2 specificity compared to domain $11^{WT}$.

We next determined if the initial optimised AB loop mutant (domain $11^{AB5}$) could be translated into the basis of an improved IGF2 super-antagonist ligand trap. An IgG1 Fc-fusion with domain $11^{E1544K}$ functioned as an IGF2 signalling antagonist in cell lines based on signalling and cell proliferation responses [40]. We expressed and purified a human IgG1 Fc-fusion domain $11^{AB5}$. Fc-domain $11^{AB5}$ binding kinetics revealed an affinity and specificity for $IGF2^{1-67}$ close to that of the single soluble domain $11^{AB5}$, either when immobilised on a Biacore chip using an anti-human IgG antibody (3.89 nM, Table 5, FIG. 6) or when immobilising a low response units of IGF2 mixed with a neutral binder (ubiquitin). IGF2 in serum, and commonly in tumours, occurs as a range of differentially glycosylated pro-IGF2 isoforms attributed to incomplete processing by pro-protein convertases (PC4) [43]. We determined the binding kinetics of recombinant pro-IGF2 isoforms to Fc-domain $11^{AB5}$ and specificity relative to IGF1. Recombinant mature ($IGF2^{1-67}$ [7.5 kDa] and pro-IGF2 (pro-$IGF2^{1-104}$ [11 kDa] and pro-$IGF2^{1-156}$ [17 kDa]) binding kinetics were performed using Fc-domain $11^{AB5}$ and Fc-domain $11^{I1572A}$ control immobilised with antibody capture. We detected higher relative affinity binding of the pathological variants of IGF2, pro-$IGF2^{1-104}$ and pro-$IGF2^{1-156}$ isoforms, to Fc-domain $11^{AB5}$ and Fc-domain $11^{AB5-RHH}$, and surprisingly binding of Fc-domain $11^{I1572A}$ to both pro-$IGF2^{1-156}$ and to a lesser extent pro-$IGF2^{1-104}$ (FIG. 6, Table 5). Binding of Fc-domain 11 constructs was independent of the Fc-fragment, as the same affinity to pro-IGF2 isoforms was obtained when immobilised IgG1 human Fc was used in the control flow cell. Solution pull-downs confirmed the specific capture of recombinant $IGF2^{1-67}$, pro-$IGF2^{1-104}$ and pro-$IGF2^{1-156}$ (multiple forms) by Fc-domain $11^{AB5}$ (FIG. 7). In order to further test the functional effects, we selected human hepatocellular carcinoma cell lines (HuH7, Hep3B) that expressed IGF2, a colorectal cancer (HT29/219) cell line that did not express high levels of IGF2, but was dependent on IGF2 in culture and a NIH 3T3 cell line expressing human pro-$IGF2^{R104A}$ following retroviral integration of a human IGF2 construct with a mutation (R104A), known to impair proteolytic cleavage of the E-domain [43]. We validated IGF2 signalling and growth dependency of cell lines by addition of dual IGF1 receptor/insulin receptor kinase inhibitor OSI-906. Immuno-precipitation with domain $11^{AB5}$ identified both mature IGF2 and pro-IGF2 isoforms in spent serum free culture supernatants, confirming that Fc-domain $11^{AB5}$ bound human IGF2 isoforms generated by tumour cell lines (FIG. 8).

To test the inhibitory effects of Fc-domain $11^{AB5}$ in vivo, we added recombinant protein in serum free conditions, to Hep3B and Huh7 ($IC_{50}$, Hep3B=35.5 μM, Huh7=1.2 μM and HT29/219=1.7 μM). Proliferation was inhibited relative to OSI-06, in Hep3B, but apoptosis was promoted in Huh7 (FIG. 10). As expected, the inhibitory concentration $IC_{50}$ for Fc-domain $11^{AB5}$ in the context of autocrine IGF2 in the media varied between cell lines, and was at least 100 times higher than the apparent $K_D$ for the binding interaction to IGF1 receptor (10-15 nM). There was no effect of an Fc-domain $11^{I1572A}$ mutant control that lacked binding to IGF2.

We next reproduced the metabolic effects of exogenous addition of $IGF2^{1-67}$ to induce hypoglycaemia in mice, similar to the cancer syndrome of non-islet tumour associated hypoglycaemia (NICTH). Pre-loading, co-injection or post-loading of Fc-domain $11^{AB5}$ resulted in significant abrogation of the hypoglycaemic effects, an effect not detected with the Fc-domain $11^{I1572A}$ non-IGF2 binding control (FIG. 9A). Whereas the co-injection of $IGF2^{1-157}$ and Fc-domain $11^{AB5}$ or Fc-domain $11^{AB5-RHH}$ in a 1:1 or 1:0.5 molar ratio, respectively, resulted in abrogation of the $IGF2^{1-67}$ induced hypoglycaemia; when the IGF2 to Fc-domain 11 ratio was reduced, the advantages of a higher affinity mutant were evident. A molar ratio of 1:0.23 significantly counteracted IGF2-induced hypoglycaemia in the case of domain $11^{AB5-RHH}$, but not with Fc-domain $11^{AB5}$ (FIG. 9B). These data demonstrate that Fc-domain $11^{AB5}$ and Fc-domain $11^{AB5-RHH}$ function as IGF2 antagonists in vivo.

An alternative autocrine-IGF21-67 tumour model was developed using a Ewing sarcoma cell line (SKNMC) selected for IGF2 dependency. Growth of a retroviral transformed SKNMC cells expressing constitutive IGF21-67 and a luciferase reporter was inhibited by Fc-domain 11AB5-RHH in culture (FIG. 11). SKNMC-IGF21-67 xenografts are predicted to be dependent on autocrine-IGF21-67 supply as adult mice do not express IGF2. IgG2 Fc-domain 11AB5-RHH purified from CHO cells was infused using osmotic mini-pumps prior to SKNMC-IGF21-67 cell line injection. Reduced xenograft growth rates in mice was observed with Fc-domain 11AB5-RHH (FIG. 12B), with induced regions of tumour cell death that resulted in reduced bioluminescence signal to volume ratio. Circulating IGF21-67 was readily detected in serum following 28 days of SKNMC-IGF267 tumour growth, but was less evident in treated Fc-domain 11AB5-RHH mice, and without alteration in total serum IGF1, Growth Hormone or IGFBP levels (FIG. 12C).

A number of candidate additive and synergistic lethality interactions were observed in SKNMC-$IGF2^{104}$ treated with Fc-domain $11^{AB5-RHH}$ and an extended oncology compound library (222 agents plus 77 additional agents from the DTP Approved Oncology Drug Set contains oncology specific compounds that have been tested in man.). The high throughput screen compared the effects of the oncology drugs in the presence and absence of a fixed concentration of the Fc-domain $11^{AB5-RHH}$ (IGF2-TRAP) that resulted in partial reduction in cell viability (10-20%) at the assay end point of 72 hrs. Evaluation of the metrics of raw data (Pearson's r scores) indicated good replicate correlation, with average r≥0.92 for all plates with an average inhibitory effect of the IGF2-TRAP alone of □100. Drugs showing p<0.05 in the rank product method applied to their interaction score were selected. A number of hits were identified, including two independent PI3-kinase inhibitors, F-04691502 ([2-amino-8-[trans-4-(2-hydroxyethoxy)cyclohexyl]-6-(6-methoxypyridin-3-yl)-4-methylpyrido-[2,3-d]pyrimidin-7(8H)-one) (p=0.011) and Pictilisib (GDC-0941; 4-[2-(1H-indazol-4-yl)-6-[(4-methylsulfonylpiperazin-1-yl)methyl]thieno[3,2-d]pyrimidin-4-yl]morpholine) (p=0.017). These were further validated by comparison of the dose response curve both in the presence and absence of Fc-domain $11^{AB5-RHH}$ (IGF2-TRAP) (FIG. 13). The IC50 for PF-04691502 shifted from 0.42 µM to 92 nM in the presence of the Fc-domain $11^{AB5-RHH}$ (IGF2-TRAP), and from 1.1 µM to 0.14 µM in the case of pictilisib, both of which are significant based on an F-test. Such ten-fold differences following combination with Fc-domain $11^{AB5-RHH}$ (IGF2-TRAP) provide indication that antagonising IGF2 signalling can reveal clinically meaningful synergistic activity, for example, with PI3 kinase inhibitors.

Figure 14:
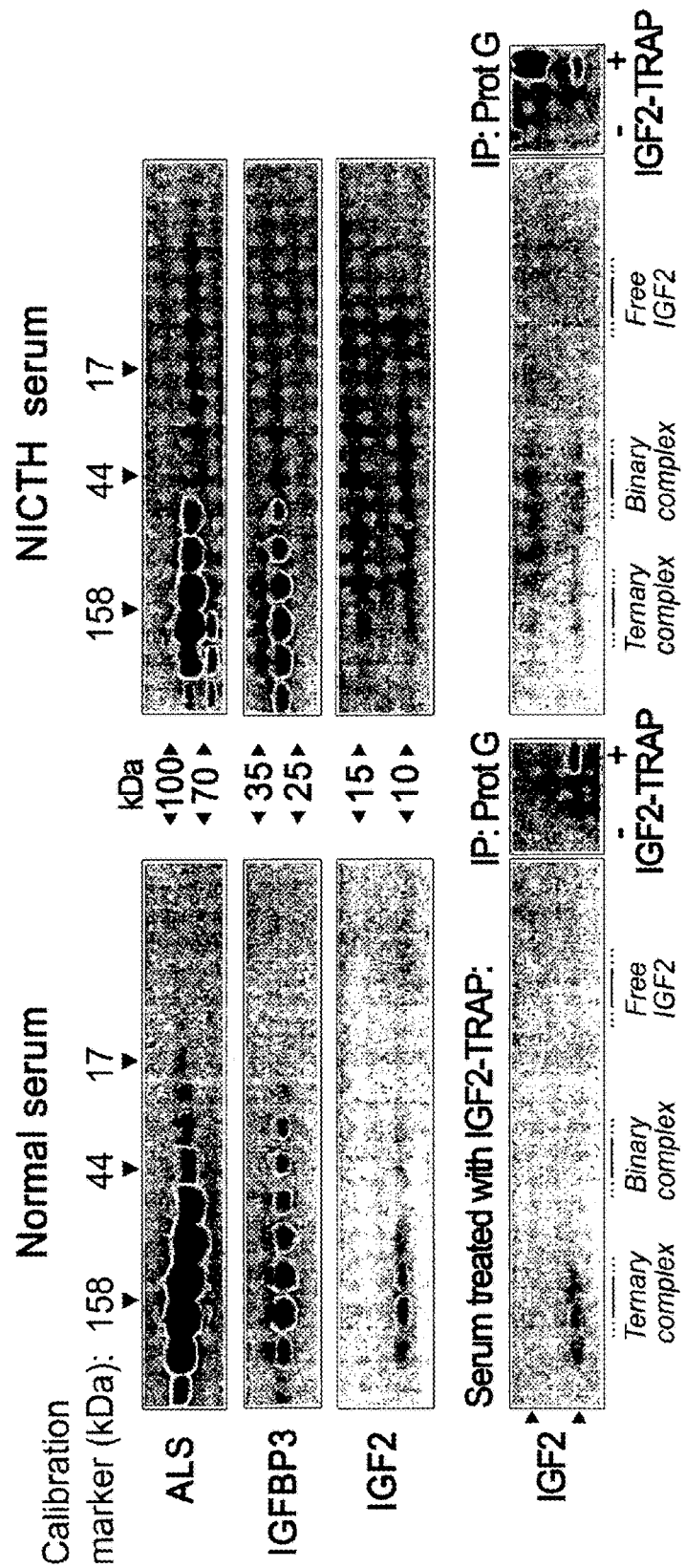
FIG. 14 IGF2-TRAP modifies the molecular distribution of IGF2 in human serum. Normal (left) and NICTH (right) sera were fractionated in a gel filtration column at neutral pH, alongside a molecular weight calibration marker, before and after incubation and depletion with IGF2-TRAP-loaded protein G beads. Elution fractions were analysed by western blot.

Changes in the molecular distribution of circulating IGF2 upon IGF2-TRAP treatment were analysed by neutral size fractionation of human serum (FIG. 14). In adult human serum, western blots of the fractions reveal that IGF2 is mainly the mature lower molecular weight isoform, and is predominantly present in a ternary complex with IGFBP3 and the acid labile subunit (ALS) (~150 kDa), and to a lesser extent in a binary complex with IGFBP3 (~40 kDa), with free IGF2 below the limit of detection. In this sample, IGF2-TRAP depleted IGF2 in the binary complex, and also partially decreased the amount IGF2 in the ternary complex (lower left panel, FIG. 14). Pull-downs confirmed that the depleted IGF2 specifically bound IGF2-TRAP. In a second experiment, serum from a patient with Non-Islet-Cell Tumour-associated Hypoglycaemia (NICTH) secondary to a GIST tumour was utilised. Western blotting of the fractions showed that IGF2 was present with additional larger molecular weight isoforms, predominantly in a binary complex. IGF2-TRAP depleted both lower and higher molecular weight isoforms of IGF2, and pull-downs confirmed specific binding to both isoforms (lower right panel, FIG. 14). These data suggest that IGF2-TRAP can target larger molecular weight pro-IGF2 isoforms associated with human cancer and NICTH (IGF syndrome).

The above experiments unexpectedly show that domain 11 of human IGF2R, despite having evolved over 150 million years, could be further evolved to an even higher affinity. In order to ensure correct folding of the β-barrel of the expressed protein, we adopted the yeast surface display technology and mutation strategies focused on the prior knowledge of specific IGF2 interacting residues in the binding site loops. We screened a library of binding loop mutants in two stages. Firstly, flow sorting with prior binding controls to select for high IGF2 affinity mutants. The advantages were the selection on the cell surface of correctly folded protein combined with live cell selection. Secondly, the expression of soluble protein derived from selected high affinity clones individually, so that selection was via a high throughput SPR based on defined criteria for selection on the $k_{off}$ of the interaction. The mutagenesis of domain 11 was focused on a number of interacting residues, informed by the high-resolution structure of these sites within the binding loops of domain 11:IGF2 [3].

Our starting premise was that mammals (human) had evolved an optimal domain 11 binding site, such that further evolutionary selection for higher affinity would likely to have been exhausted. Our data suggest that single mutations in loops CD, HI and FG may have resulted in relatively small (<2 fold) incremental gains in affinity, supporting a premise that the binding site has fully evolved in human. In the experimental situation described here-in, our evidence also suggests the contrary, as we have been able identify forms of domain 11 with up to 100 fold increase in affinity without compromising specificity for IGF2.

Comparison of the high solution NMR structures of the domain $11^{WT, AB3}$ and $^{AB5}$ reveals that structural perturbations within the binding site are localized to the AB loop[3]. Although the G1546W mutation in domain $11^{AB5}$ introduces a bulky side-chain into the AB loop and binding site, residues in the neighbouring CD and FG loops are only minimally perturbed. The observation that affinity for IGF2 can be dramatically increased whilst preserving the shape complementarity to T16 of IGF2 may be a critical factor underpinning the success of this method whilst retaining specificity for IGF2 over IGF1. Longer range effects transmitted via strand β-A to the C-terminal helix may reflect a structural coupling between the conformation of the AB loop and inter-domain conformational changes induced in the full length receptor, perhaps triggered by IGF2 binding.

The thermodynamic pay-offs between entropy (predominantly solvent exclusion) and enthalpy (charge attraction) of the interaction between IGF2 and domain 11 showed some consistent differences between domain 11 AB loop mutants, including the effects of CD and FG loop mutations. Previously we showed that the reduced $k_{off}$ associated with an AB loop E1544K was via improvement of the entropic barrier of the interaction compared to wild type domain 11 [23]. Mutation of the AB loop in the domain $11^{AB3}$ mutant would be consistent with rigidification and improved solvent exclusion as with domain $11^{E1544K}$. This effect was only unmasked in domain $11^{AB5}$ with respect to thermodynamic terms, after the introduction of additional mutations in the CD and FG loops. Thus the overall improvement in Gibbs free energy of the interaction (ΔG°) appeared to require combinations of mutations that reduced the entropic barrier (improved solvent exclusion).

The increased bioavailability of IGF2, and downstream activation of the IGF1 receptor pathway, accounts for the clinical phenotypes in overgrowth syndromes such as Beckwith-Weidemann syndrome, and more common somatic events in human cancer (GCID: GC11M002113). Systemic excess of pro-IGF2 (IGF2$^{87}$, IGF2$^{104}$) in NICTH, mediated via activation of the insulin receptor, is associated with large bulk tumours such as in sarcoma and hepatocellular carcinoma [44, 45] that express IGF2. There is no current specific treatment for NICTH. Local IGF2 supply appears to regulate early angiogenic stages of tumour progression and the later stages of transformation to carcinoma [46-48]. Increased IGF2 supply through IGF2 loss of imprinting, genomic amplification and decreased ligand clearance occurs frequently in common cancers, e.g. colon [16, 17, 20]. The clinical development of single agent/single receptor IGF1R inhibitors and anti-IGF1R humanised monoclonal antibodies have been limited, mainly because of incomplete IGF2 pathway inhibition and frequent bypass of IGF1R via IGF2 activation of isoform A of the insulin receptor (IR-A) [49]. In addition, frequent activation of a central feedback loop in the brain following IGF1 targeting also results in paradoxical increased systemic IGF1 supply [50]. Targeting either bioavailable IGF ligands or by dual IGF1R/IR-A receptor kinase inhibitors may circumvent many of the limitations of just targeting IGF1R alone [49, 50]. Few agents have been developed that solely target IGF2 without cross-reacting with IGF1, e.g. an antibody or soluble domain 11 [40, 51]. The specific high affinity IGF2 super-antagonists generated here may be adapted and tested in appropriate models, including human tumour models, in order to translate these findings to treatment in man.

REFERENCES

1. Pollak, M. Nat Rev Cancer, 2008. 8(12): p. 915-28.
2. Ghosh, P., N. M. Dahms, and S. Kornfeld Nat Rev Mol Cell Biol, 2003. 4(3): p. 202-12.
3. Williams, C., et al. Science, 2012. 338(6111): p. 1209-13.
4. Canfield, W. M. and S. Kornfeld J Biol Chem, 1989. 264(13): p. 7100-3.
5. Clairmont, K. B. and M. P. Czech J Biol Chem, 1989. 264(28): p. 16390-2.
6. Linnell, J., G. Groeger, and A. B. Hassan J Biol Chem, 2001. 276(26): p. 23986-91.
7. Lobel, P., N. M. Dahms, and S. Kornfeld J Biol Chem, 1988. 263(5): p. 2563-70.
8. Morgan, D. O., et al. Nature, 1987. 329(6137): p. 301-7.
9. Tong, P. Y., S. E. Tollefsen, and S. Kornfeld J Biol Chem, 1988. 263(6): p. 2585-8.
10. Yandell, C. A., et al. J Biol Chem, 1999. 274(38): p. 27076-82.
11. Lau, M. M., et al. Genes Dev, 1994. 8(24): p. 2953-63.
12. Ludwig, T., et al. Dev-Biol, 1996. 177(2): p. 517-35 issn: 0012-1606.
13. Wylie, A. A., et al. Am J Pathol, 2003. 162(1): p. 321-8.
14. Hughes, J., et al. PLoS One, 2013. in press.
15. Wang, Z. Q., et al. Nature, 1994. 372(6505): p. 464-7.
16. *Comprehensive molecular characterization of human colon and rectal cancer.* Nature, 2012. 487(7407): p. 330-7.
17. Bergman, D., et al. Gerontology, 2013. 59(3): p. 240-9.
18. De Souza, A. T., et al. Nat Genet, 1995. 11(4): p. 447-9.
19. Hankins, G. R., et al. Oncogene, 1996. 12(9): p. 2003-9.
20. Seshagiri, S., et al. Nature, 2012. 488(7413): p. 660-4.
21. Wutz, A., et al. Development, 2001. 128(10): p. 1881-7.
22. Brown, J., et al. EMBO J, 2008. 27(1): p. 265-76.
23. Zaccheo, O. J., et al. J Mol Biol, 2006. 359(2): p. 403-21.
24. Delaine, C., et al. J Biol Chem, 2007. 282(26): p. 18886-94.
25. Murray, P. J., et al. Anal Biochem, 1995. 229(2): p. 170-9.
26. Stammers, D. K., et al. FEBS Lett, 1991. 283(2): p. 298-302.
27. Wojciechowicz, D., et al. Mol Cell Biol, 1993. 13(4): p. 2554-63.
28. Wu, S. and G. J. Letchworth Biotechniques, 2004. 36(1): p. 152-4.
29. Chao, G., et al. Nat Protoc, 2006. 1(2): p. 755-68.
30. Lescop, E., et al. J Am Chem Soc, 2007. 129(10): p. 2756-7.
31. Delaglio, F., et al. J Biomol NMR, 1995. 6(3): p. 277-93.
32. Vranken, W. F., et al. Proteins, 2005. 59(4): p. 687-96.
33. d'Auvergne, E. J. and P. R. Gooley J Biomol NMR 2008 40(2): p. 121-33.
34. d'Auvergne, E. J. and P. R. Gooley. J Biomol NMR 2008 40(2): p. 107-19.
35. Clore, G. M., et al. Journal of the American Chemical Society, 1990. 112(12): p. 4989-4991.
36. Lipari, G. and A. Szabo Journal of the American Chemical Society, 1982. 104(17): p. 4546-4559.
37. Lipari, G. and A. Szabo Journal of the American Chemical Society, 1982. 104(17): p. 4559-4570.
38. d'Auvergne, E. J. and P. R. Gooley J Biomol NMR 2003 25(1): p. 25-39.
39. d'Auvergne, E. J. and P. R. Gooley J Biomol NMR 2006 35(2): p. 117-35.
40. Prince, S. N., et al. Mol Cancer Ther, 2007. 6(2): p. 607-17.
41. Mergler, M., K. Wolf, and M. Zimmermann Appl Microbiol Biotechnol 2004. 63(4): p. 418-21.
42. Tinoco, I., K. Sauer, and J. C. Wang, *Physical chemistry: prinicples and applications in biological sciences.* 1978, Englewood Cliffs, N.J.: Prentice-Hall. xv, 624 p.
43. Duguay, S. J., et al. J Biol Chem, 1998. 273(29): p. 18443-51.
44. Fukuda, I., et al. Growth Horm IGF Res, 2006. 16(4): p. 211-6.
45. Rikhof, B., et al. Ann Oncol, 2009. 20(9): p. 1582-8.
46. Church, D. N., et al. Oncogene, 2012. 31(31): p. 3635-46.
47. Haley, V. L., et al. EMBO Mol Med, 2012. 4(8): p. 705-18.
48. Christofori, G., P. Naik, and D. Hanahan, Nature, 1994. 369(6479): p. 414-8.
49. Yee, D. J Natl Cancer Inst, 2012. 104(13): p. 975-81.
50. Pollak, M. Clin Cancer Res, 2012. 18(1): p. 40-50.
51. Chen, W., et al. Mol Cancer Ther, 2012. 11(7): p. 1400-10.
52. Zakeri B et al PNAS (2012) 109 12 E690-E697.
53. Terpe et al (2003) Appl. Microbiol. Biotechnol. 6 523-533
54. Ling C et al (2012) Cancer gene therapy 19(10):697-706

TABLE 1

| Loop | Mutant Domain 11 | Kinetics | | | | Steady state | |
|---|---|---|---|---|---|---|---|
| | | $K_D$ (nM) | $k_{on}$ ($\times 10^6$ M$^{-1}$s$^{-1}$) | $k_{off}$ (s$^{-1}$) | Chi$^2$ (RU$^2$) | $K_D$ (nM) | Chi$^2$ (RU$^2$) |
| AB | WT | 46 ± 1.8 | 5.0 | 0.23 | 0.33 | 64 ± 1.0 | 0.24 |
| | AB3 | 15.3 ± 2.0 | 2.76 | 0.044 | 0.41 | 15.5 ± 3.3 | 0.77 |
| | AB5 | 5.07 ± 0.87 | 4.21 | 0.0208 | 0.87 | 6.44 ± 1.06 | 0.14 |
| | W1546F | 4.35 ± 0.49 | 4.5 | 0.0180 | 0.767 | 5.00 ± 0.93 | 0.129 |
| FG | P1599A* | >70 | Nd | >0.1 | — | >70 | — |
| | P1599V* | >100 | Nd | >0.1 | — | >100 | — |
| | P1599G* | >200 | Nd | >0.2 | — | >200 | — |
| | S1600A | 89.10 ± 5.1 | 2.39 | 0.2126 | nd | 84.65 ± 15.20 | 0.04 |
| | S1600V | >200 | Nd | >0.2 | nd | >200 | — |
| | S1600L | >200 | Nd | >0.2 | nd | >200 | — |
| | S1600Y | >200 | Nd | >0.2 | nd | >200 | — |

TABLE 1-continued

| Loop | Mutant Domain 11 | Kinetics $K_D$ (nM) | $k_{on}$ (×10⁶ M⁻¹s⁻¹) | $k_{off}$ (s⁻¹) | Chi² (RU²) | Steady state $K_D$ (nM) | Chi² (RU²) |
|---|---|---|---|---|---|---|---|
|  | S1600N | 24.44 ± 8.70 | 3.95 | 0.0910 | 0.15 | 29.67 ± 9.54 | 0.01 |
|  | K1601A | 6.80 ± 0.65 | 3.26 | 0.0220 | 0.51 | 8.51 ± 0.39 | 0.04 |
|  | K1601R | 4.75 ± 0.08 | 5.28 | 0.0251 | 0.37 | 5.78 ± 0.18 | 0.07 |
|  | S1602A | 16.48 ± 3.83 | 1.57 | 0.0250 | 0.63 | 19.92 ± 3.77 | 0.17 |
|  | S1602H | 3.19 ± 1.00 | 3.61 | 0.0112 | 1.24 | 5.44 ± 1.41 | 0.96 |
|  | S1602N | 4.75 ± 0.52 | 2.38 | 0.0112 | 0.56 | 7.93 ± 2.29 | 0.46 |
|  | S1602Q | 3.61 ± 1.19 | 5.88 | 0.0191 | 0.57 | 5.11 ± 0.73 | 0.13 |
|  | G1603A | 8.69 ± 1.48 | 2.14 | 0.0183 | 0.45 | 12.09 ± 0.69 | 0.16 |
|  | G1603K | 2.73 ± 0.95 | 4.66 | 0.0121 | 1.18 | 4.54 ± 0.91 | 1.18 |
|  | L1604A | 48.34 ± 8.4 | 0.79 | 0.0397 | 0.26 | 59.96 ± 19.8 | 0.01 |
| HI | K1631A | >200 | — | — | — | >200 | — |
|  | K1631R | 12.29 ± 2.81 | 7.18 | 0.0867 | 0.23 | 13.51 ± 2.65 | 0.08 |
|  | K1631E | >100 | — | >0.1 | — | >100 | — |
|  | K1631W | 2.94 ± 0.37 | 1.18 | 0.0034 | 1.47 | 12.16 ± 2.35 | 3.16 |
|  | Q1632A | 3.76 ± 0.54 | 4.50 | 0.0167 | 0.57 | 4.84 ± 0.22 | 0.12 |
|  | Q1632K | 11.07 ± 2.10 | 1.96 | 0.0212 | 0.34 | 12.84 ± 0.63 | 0.05 |
|  | Q1632E | 39.83 ± 7.10 | 0.52 | 0.0202 | 2.11 | 52.41 ± 4.29 | 0.06 |
|  | Q1632L | 5.75 ± 1.05 | 3.18 | 0.0175 | 1.17 | 9.34 ± 1.69 | 2.00 |
|  | T1633A | 26.41 ± 9.49 | 0.80 | 0.0196 | 0.21 | 53.55 ± 10.0 | 0.19 |

TABLE 2

| Mutant Domain 11 | Kinetics $K_D$ (nM) | $k_{on}$ (×10⁶ M⁻¹s⁻¹) | $k_{off}$ (s⁻¹) | Chi² (RU²) | Steady state $K_D$ (nm) | Chi² (RU²) |
|---|---|---|---|---|---|---|
| WT | 46 ± 1.8 | 5.0 | 0.23 | 0.33 | 64 ± 1.0 | 0.24 |
| AB3 | 15.3 ± 2.0 | 2.76 | 0.044 | 0.41 | 15.5 ± 3.3 | 0.77 |
| AB3 + 62B (FG-P1597H) | 1.23 ± 0.32 | 10.6 | 0.013 | 1.62 | 1.76 ± 0.47 | 1.43 |
| AB3 + 73E (CD-Q1569R) | 2.30 ± 0.27 | 13.6 | 0.031 | 1.54 | 3.15 ± 0.41 | 0.25 |
| WT + 23D (HI-HFQS)* | 176 | 0.25 | 0.065 | 0.56 | 220.5 | 0.45 |
| WT + 26C (HI-DMQT)* | 130 | 1.89 | 0.24 | 0.17 | 127 | 0.19 |
| WT + 27G (HI-NMAL)* | 195 | 2.0 | 0.25 | 0.19 | 194 | 0.13 |
| WT + 312G (HI-VKLM)* | 119 | 1.07 | 0.15 | 0.27 | 135 | 0.45 |
| AB5 + 51F (HI-NRQS)* | 13.5 | 7.4 | 0.10 | 0.31 | 6.94 | 0.26 |

*Protein quality poor based on absorption spectra

TABLE 3

| Domain 11 Mutant | Kinetics $K_D$ (nM) | $k_{on}$ (×10⁶ M⁻¹s⁻¹) | $k_{off}$ (s⁻¹) | Steady State $K_D$ (nM) | Number of mutations |
|---|---|---|---|---|---|
| AB3 | 15.3 ± 2.0 | 2.76 | 0.044 | 15.5 ± 3.3 | 3 |
| AB3 Q1569R | 2.30 ± 0.27 | 13.6 | 0.031 | 3.15 ± 0.41 | 4 |
| AB3 P1597H | 1.23 ± 0.32 | 10.6 | 0.013 | 1.76 ± 0.47 | 4 |
| AB3 P1597K | 2.78 ± 0.61 | 10.5 | 0.0287 | 3.59 ± 0.77 | 4 |
| AB3 Q1569R P1597H | 0.90 ± 0.29 | 18.9 | 0.0153 | 1.73 ± 0.4 | 5 |
| AB3 Q1569R P1597K | 1.34 ± 0.47 | 20.0 | 0.0241 | 2.27 ± 1.04 | 5 |
| AB3 P1597H K1631W | 17.55 ± 1.88 | 19.7 | 0.3478 | 18.67 ± 2.23 | 5 |
| AB3 P1597H HI²³ᴰ | nd | nd | 0.012 | nd | 8 |
| AB3 P1597K S1602H | 3.73 | 2.74 | 0.0102 | 5.332 | 5 |
| AB3 Q1569R P1597H S1602H | 0.74 ± 0.22 | 14.1 | 0.010 | 1.53 ± 0.46 | 6 |
| AB3 Q1569R P1597K S1602H | 0.79 ± 0.25 | 20.1 | 0.016 | 1.39 ± 0.48 | 6 |
| AB3 Q1569R P1597H K1631W | np | np | np | np | 6 |
| AB3 Q1569R P1597K K1631W | np | np | np | np | 6 |
| AB3 Q1569R P1597H S1602H G1603K | 0.62 ± 0.03 | 17.5 | 0.0108 | 1.31 ± 0.16 | 7 |
| AB3 Q1569R P1597K S1602H G1603K | 0.78 ± 0.22 | 20.8 | 0.0171 | 1.62 ± 0.41 | 7 |
| AB3 Q1569R P1597H S1602H K1631W | np | np | np | np | 7 |

TABLE 3-continued

| Domain 11 Mutant | $K_D$ (nM) | $k_{on}$ (×10$^6$ M$^{-1}$s$^{-1}$) | $k_{off}$ (s$^{-1}$) | Steady State $K_D$ (nM) | Number of mutations |
|---|---|---|---|---|---|
| AB5 | 5.07 ± 0.87 | 4.21 | 0.0208 | 6.44 ± 1.06 | 5 |
| AB5 Q1569R | 2.24 ± 0.44 | 8.04 | 0.0175 | 3.22 ± 0.55 | 6 |
| AB5 P1597H | 1.90 ± 0.60 | 3.68 | 0.0070 | 2.79 ± 0.52 | 6 |
| AB5 P1597A | 9.07 ± 1.08 | 1.90 | 0.0174 | 12.44 ± 0.69 | 6 |
| AB5 P1597K | 1.94 ± 0.39 | 9.54 | 0.0120 | 2.21 ± 0.14 | 6 |
| AB5 P1597L | 3.86 ± 1.68 | 4.18 | 0.0150 | 4.85 ± 1.82 | 6 |
| AB5 P1597N | 4.13 ± 1.74 | 4.72 | 0.0180 | 5.36 ± 2.24 | 6 |
| AB5 P1597Q | 3.83 ± 2.42 | 6.53 | 0.0203 | 4.51 ± 2.66 | 6 |
| AB5 P1597S | 4.19 ± 1.80 | 5.00 | 0.0193 | 4.90 ± 1.88 | 6 |
| AB5 HI$^{23D}$ | np | np | 0.012 | np | 9 |
| AB5 Q1569R P1597H | 1.95 ± 0.60 | 3.2 | 0.0058 | 5.40 ± 0.98 | 7 |
| AB5 Q1569R P1597K | 0.95 | 9.59 | 0.0091 | 1.69 | 7 |
| AB5 P1597H S1602H | 1.17 ± 0.2 | 3.50 | 0.0046 | 2.93 ± 0.47 | 7 |
| AB5 P1597K S1602H | 4.62 | 2.09 | 0.0096 | 7.85 | 7 |
| AB5 P1597H HI$^{2-3D}$ | np | np | np | np | 10 |
| AB5 Q1569R P1597H S1602H | 0.65 ± 0.11 | 5.90 | 0.0038 | 2.0 ± 0.50 | 8 |
| AB5 Q1569R P1597K S1602H | 0.92 ± 0.13 | 7.87 | 0.0073 | 2.11 ± 0.55 | 8 |
| AB5 Q1569R P1597H G1603K | 0.87 ± 0.09 | 6.67 | 0.0058 | 2.01 ± 0.30 | 8 |
| AB5 Q1569R P1597H Q1632L | np | np | np | np | 8 |
| AB5 Q1569R P1597K K1631W | 1.02 ± 0.06 | 11.20 | 0.0115 | 1.95 ± 0.47 | 8 |
| AB5 Q1569R P1597K K1631W | np | np | np | np | 8 |
| AB5 Q1569R P1597H HI2-3D | np | np | np | np | 11 |
| AB5 Q1569R P1597H S1602H G1603K | np | np | 0.005 | np | 9 |
| AB5 Q1569R P1597K S1602H G1603K | np | np | 0.008 | np | 9 |
| AB5 Q1569R P1597H S1602H K1631W | np | np | np | np | 9 |
| AB5 Q1569R P1597K S1602H K1631W | np | np | np | np | 9 |
| AB5 Q1569R P1597K S1602H Q1632L | np | np | np | np | 9 |
| AB5 Q1569R P1597H S1602H G1603K K1631W | np | np | np | np | 10 |
| AB5 Q1569R P1597K S1602H G1603K K1631W | np | np | np | np | 10 |

TABLE 4

| Mutant | $K_D$ (nM) | $k_{on}$ (×10$^6$ M$^{-1}$s$^{-1}$) | $k_{off}$ (s$^{-1}$) |
|---|---|---|---|
| WT | 35.06 ± 10.45 | 2.68 | 0.1441 |
| AB3 | 11.85 ± 0.20 | 3.43 | 0.0381 |
| AB3 Q1569R P1597H | 0.47 ± 0.06 | 19.9 | 0.0091 |
| AB3 Q1569R P1597H S1602H | 0.40 ± 0.07 | 16.1 | 0.0064 |
| AB3 Q1569R P1597H S1602H G1603K | 0.43 ± 0.03 | 24.3 | 0.0087 |
| AB5 | 4.38 ± 0.78 | 4.17 | 0.0180 |
| AB5 Q1569R P1597H | 1.46 ± 0.29 | 2.37 | 0.0034 |
| AB5 Q1569R P1597H S1602H | 0.71 ± 0.10 | 4.41 | 0.0030 |
| AB5 P1597H S1602H | 0.62 ± 0.34 | 5.32 | 0.0029 |
| AB5 P1597H S1602H G1603K | 0.69 ± 0.06 | 7.54 | 0.0051 |

TABLE 5

| IGF form | $K_D$ (nM) | $k_{on}$ (×10$^6$ M$^{-1}$s$^{-1}$) | $k_{off}$ (s$^{-1}$) |
|---|---|---|---|
| Interaction with Fc-domain 11$^{AB5}$ | | | |
| IGF2$^{1-67}$ | 3.89 | 6.47 | 0.025 |
| IGF2$^{1-104}$ | 0.54 | 12.87 | 0.0069 |
| IGF2$^{1-156}$ | 0.21* | 4.19* | 0.0009 |
| IGF1 | — | — | — |
| Interaction with Fc-domain 11$^{AB5-RHH}$ | | | |
| IGF2$^{1-67}$ | 0.54 | 2.60 | 0.0014 |
| IGF2$^{1-104}$ | 0.39 | 1.29 | 0.0005 |
| IGF2$^{1-156}$ | 1.13* | 0.23* | 0.0003 |
| IGF1 | — | — | — |
| Interaction with Fc-domain 11$^{I1572A}$ | | | |
| IGF2$^{1-67}$ | — | — | — |
| IGF2$^{1-104}$ | 4.41 | 0.52 | 0.002 |
| IGF2$^{1-156}$ | 2.71* | 0.29* | 0.0008 |
| IGF1 | — | — | — |

*Note,
kinetic analysis may be inaccurate because concentration of the recombinant IGF2$^{1-156}$ (Gropep). This consists of a mixture of three isoforms, the full-length protein and truncated peptides (151 and 141 residues long).

| | Sequences |
|---|---|
| 1 | mgaaagrsph lgpaparrpq rsllllqlll lvaapgstqa qaapfpelcs ytweavdtkn |
| 61 | nvlykinicg svdivqcgps savcmhdlkt rtyhsvgdsv lrsatrslle fnttvscdqq |
| 121 | gtnhrvqssi aflcgktlgt pefvtatecv hyfewrttaa ckkdifkank evpcyvfdee |
| 181 | lrkhdlnpli klsgaylvdd sdpdtslfin vcrdidtlrd pgsqlracpp gtaaclvrgh |
| 241 | qafdvgqprd glklvrkdrl vlsyvreeag kldfcdghsp avtitfvcps erregtipkl |
| 301 | taksncryei ewiteyachr dylesktcsl sgeqqdvsid ltplaqsggs syisdgkeyl |
| 361 | fylnvcgete iqfcnkkqaa vcqvkksdts qvkaagryhn qtlrysdgdl tliyfggdec |
| 421 | ssgfqrmsvi nfecnktagn dgkgtpvftg evdctyfftw dteyacvkek edllcgatdg |
| 481 | kkrydlsalv rhaepeqnwe avdgsqtete kkhffinich rvlqegkarg cpedaavcav |
| 541 | dkngsknlgk fisspmkekg niqlsysdgd dcghgkkikt nitlvckpgd lesapvlrts |
| 601 | geggcfyefe wrtaaacvls ktegenctvf dsqagfsfdl spltkkngay kvetkkydfy |
| 661 | invcgpvsvs pcqpdsgacq vaksdektwn lglsnaklsy ydgmiqlnyr ggtpynnerh |
| 721 | tpratlitfl cdrdagvgfp eyqeednsty nfrwytsyac peeplecvvt dpstleqydl |
| 781 | sslakseggl ggnwyamdns gehvtwrkyy invcrplnpv pgcnryasac qmkyekdqgs |
| 841 | ftevvsisnl gmaktgpvve dsgsllleyv ngsacttsdg rqttyttrih lvcsrgrlns |
| 901 | hpifslnwec vvsflwntea acpiqtttdt dqacsirdpn sgfvfnlnpl nssqgynvsg |
| 961 | igkifmfnvc gtmpvcgtil gkpasgceae tqteelknwk parpvgieks lqlstegfit |
| 1021 | ltykgplsak gtadafivrf vcnddvysgp lkflhqdids gqgirntyfe fetalacvps |
| 1081 | pvdcqvtdla gneydltgls tvrkpwtavd tsvdgrkrtf ylsvcnplpy ipgcqgsavg |
| 1141 | sclvsegnsw nlgvvqmspq aaangslsim yvngdkcgnq rfstritfec aqisgspafq |
| 1201 | lqdgceyvfi wrtveacpvv rvegdncevk dprhgnlydl kplglndtiv sageytyyfr |
| 1261 | vcgklssdvc ptsdkskvvs scqekrepqg fhkvaglltq kltyengllk mnftggdtch |
| 1321 | kvyqrstaif fycdrgtqrp vflketsdcs ylfewrtqya cppfdltecs fkdgagnsfd |
| 1381 | lsslsrysdn weaitgtgdp ehylinvcks lapqagtepc ppeaaacllg gskpvnlgrv |
| 1441 | rdgpqwrdgi ivlkyvdgdl cpdgirkkst tirftcsesq vnsrpmfisa vedceytfaw |
| 1501 | ptatacpmks <u>nehddcqvtn pstqhlfdls slsqraqfta aysekqlvym sicqenencp</u> |
| 1561 | <u>pgvgacfgqt risvgkankr lryvdqvlql vykdgspcps ksglsyksvi sfvcrpeagp</u> |
| 1621 | <u>tnrpmlisld kqtctlffsw htplaceqat</u> ecsvrngssi vdlsplihrt ggyeaydese |
| 1681 | ddasdtnpdf yinicqplnp mhavpcpaga avckvpidgp pidigrvagp pilnpianei |
| 1741 | ylnfesstpc ladkhfnyts liafhckrgv smgtpkllrt secdfvfewe tpvvcpdevr |
| 1801 | mdgctltdeq llysfnlssl ststfkvtrd srtysvgvct favgpeqggc kdggvcllsg |
| 1861 | tkgasfgrlq smkldyrhqd eavvlsyvng drcppetddg vpcvfpfifn gksyeeciie |
| 1921 | sraklwcstt adydrdhewg fcrhsnsyrt ssiifkcded edigrpqvfs evrgcdvtfe |
| 1981 | wktkvvcppk kleckfvqkh ktydlrllss ltgswslvhn gvsyyinlcq kiykgplgcs |
| 2041 | erasicrrtt tgdvqvlglv htqklgvigd kvvvtyskgy pcggnktass vieltctktv |
| 2101 | grpafkrfdi dsctyyfswd sraacavkpq evqmvngtit npingksfsl gdiyfklfra |
| 2161 | sgdmrtngdn ylyeiqlssi tssrnpacsg anicqvkpnd qhfsrkvgts dktkyylqdg |
| 2221 | dldvvfasss kcgkdktksv sstiffhcdp lvedgipefs hetadcqylf swytsavcpl |
| 2281 | gvgfdsenpg ddgqmhkgls ersqavgavl slllvaltcc llalllykke rretvisklt |
| 2341 | tccrrssnvs ykyskvnkee etdenetewl meeiqlpppr qgkegqengh ittksvkals |

-continued

| Sequences |
|---|

2401  slhgddqdse devltipevk vhsgrgagae sshpvrnaqs nalqereddr vglvrgekar 2461  kgksssaqqk tvsstklvsf hddsdedllh i
Domain 11 (1511-1650) is underlined
SEQ ID NO: 1 Human IGF2R

```
   1  cgagcccagt cgagccgcgc tcacctcggg ctcccgctcc gtctccacct ccgcctttgc
  61  cctggcggcg cgaccccgtc ccggcgcggc ccccagcagt cgcgcgccgt tagcctcgcg
 121  cccgccgcgc agtccgggcc cggcgcgatg ggggccgccg ccggccggag cccccacctg
 181  gggcccgcgc ccgccgccg cccgcagcgc tctctgctcc tgctgcagct gctgctgctc
 241  gtcgctgccc cggggtccac gcaggcccag gccgccccgt tccccgagct gtgcagttat
 301  acatgggaag ctgttgatac caaaaataat gtactttata aaatcaacat ctgtggaagt
 361  gtggatattg tccagtgcgg gccatcaagt gctgtttgta tgcacgactt gaagacacgc
 421  acttatcatt cagtgggtga ctctgttttg agaagtgcaa ccagatctct cctggaattc
 481  aacacaacag tgagctgtga ccagcaaggc acaaatcaca gagtccagag cagcattgcc
 541  ttcctgtgtg ggaaaaccct gggaactcct gaatttgtaa ctgcaacaga atgtgtgcac
 601  tactttgagt ggaggaccac tgcagcctgc aagaaagaca tatttaaagc aaataaggag
 661  gtgccatgct atgtgtttga tgaagagttg aggaagcatg atctcaatcc tctgatcaag
 721  cttagtggtg cctacttggt ggatgactcc gatccggaca cttctctatt catcaatgtt
 781  tgtagagaca tagacacact acgagaccca ggttcacagc tgcgggcctg tcccccccggc
 841  actgccgcct gcctggtaag aggacaccag gcgtttgatg ttggccagcc ccgggacgga
 901  ctgaagctgg tgcgcaagga caggcttgtc ctgagttacg tgagggaaga ggcaggaaag
 961  ctagactttt gtgatggtca cagccctgcg gtgactatta catttgtttg cccgtcggag
1021  cggagagagg gcaccattcc caaactcaca gctaaatcca actgccgcta tgaaattgag
1081  tggattactg agtatgcctg ccacagagat tacctggaaa gtaaaacttg ttctctgagc
1141  ggcgagcagc aggatgtctc catagacctc acaccacttg cccagagcgg aggttcatcc
1201  tatatttcag atggaaaaga atatttgttt tatttgaatg tctgtggaga aactgaaata
1261  cagttctgta taaaaaaaca agctgcagtt tgccaagtga aaagagcga tacctctcaa
1321  gtcaaagcag caggaagata ccacaatcag accctccgat attcggatgg agacctcacc
1381  ttgatatatt tggaggtga tgaatgcagc tcagggtttc agcggatgag cgtcataaac
1441  tttgagtgca ataaaaccgc aggtaacgat gggaaggaa ctcctgtatt cacaggggag
1501  gttgactgca cctacttctt cacatgggac acggaatacg cctgtgttaa ggagaaggaa
1561  gacctcctct gcggtgccac cgacgggaag aagcgctatg acctgtccgc gctggtccgc
1621  catgcagaac cagagcagaa ttgggaagct gtggatggca gtcagacgga aacagagaag
1681  aagcatttt tcattaatat ttgtcacaga gtgctgcagg aaggcaaggc acgagggtgt
1741  cccgaggacg cggcagtgtg tgcagtggat aaaaatggaa gtaaaaatct gggaaaattt
1801  atttcctctc ccatgaaaga gaaaggaaac attcaactct cttattcaga tggtgatgat
1861  tgtggtcatg gcaagaaaat taaaactaat atcacacttg tatgcaagcc aggtgatctg
1921  gaaagtgcac cagtgttgag aacttctggg gaaggcggtt gcttttatga gtttgagtgg
1981  cgcacagctg cggcctgtgt gctgtctaag acagaagggg agaactgcac ggtctttgac
2041  tcccaggcag ggttttcttt tgacttatca cctctcacaa agaaaaatgg tgcctataaa
```

-continued

| | Sequences |
|---|---|
| 2101 | gttgagacaa agaagtatga cttttatata aatgtgtgtg gcccggtgtc tgtgagcccc |
| 2161 | tgtcagccag actcaggagc ctgccaggtg gcaaaaagtg atgagaagac ttggaacttg |
| 2221 | ggtctgagta atgcgaagct ttcatattat gatgggatga tccaactgaa ctacagaggc |
| 2281 | ggcacaccct ataacaatga aagacacaca ccgagagcta cgctcatcac ctttctctgt |
| 2341 | gatcgagacg cgggagtggg cttccctgaa tatcaggaag aggataactc cacctacaac |
| 2401 | ttccggtggt acaccagcta tgcctgcccg gaggagcccc tggaatgcgt agtgaccgac |
| 2461 | ccctccacgc tggagcagta cgacctctcc agtctggcaa aatctgaagg tggccttgga |
| 2521 | ggaaactggt atgccatgga caactcaggg gaacatgtca cgtggaggaa atactacatt |
| 2581 | aacgtgtgtc ggcctctgaa tccagtgccg ggctgcaacc gatatgcatc ggcttgccag |
| 2641 | atgaagtatg aaaaagatca gggctccttc actgaagtgg tttccatcag taacttggga |
| 2701 | atggcaaaga ccggcccggt ggttgaggac agcggcagcc tccttctgga atacgtgaat |
| 2761 | gggtcggcct gcaccaccag cgatggcaga cagaccacat ataccacgag gatccatctc |
| 2821 | gtctgctcca ggggcaggct gaacagccac cccatctttt ctctcaactg ggagtgtgtg |
| 2881 | gtcagtttcc tgtggaacac agaggctgcc tgtcccattc agacaacgac ggatacagac |
| 2941 | caggcttgct ctataaggga tcccaacagt ggatttgtgt ttaatcttaa tccgctaaac |
| 3001 | agttcgcaag gatataacgt ctctggcatt gggaagattt ttatgtttaa tgtctgcggc |
| 3061 | acaatgcctg tctgtgggac catcctggga aaacctgctt ctggctgtga ggcagaaacc |
| 3121 | caaactgaag agctcaagaa ttggaagcca gcaaggccag tcggaattga gaaaagcctc |
| 3181 | cagctgtcca cagagggctt catcactctg acctacaaag ggcctctctc tgccaaaggt |
| 3241 | accgctgatg cttttatcgt ccgctttgtt tgcaatgatg atgtttactc agggcccctc |
| 3301 | aaattcctgc atcaagatat cgactctggg caagggatcc gaaacactta ctttgagttt |
| 3361 | gaaaccgcgt tggcctgtgt tccttctcca gtggactgcc aagtcaccga cctggctgga |
| 3421 | aatgagtacg acctgactgg cctaagcaca gtcaggaaac cttggacggc tgttgacacc |
| 3481 | tctgtcgatg ggagaaagag gactttctat ttgagcgttt gcaatcctct cccttacatt |
| 3541 | cctggatgcc agggcagcgc agtggggtct tgcttagtgt cagaaggcaa tagctggaat |
| 3601 | ctgggtgtgg tgcagatgag tccccaagcc gcggcgaatg gatctttgag catcatgtat |
| 3661 | gtcaacggtg acaagtgtgg gaaccagcgc ttctccacca ggatcacgtt tgagtgtgct |
| 3721 | cagatatcgg gctcaccagc atttcagctt caggatggtt gtgagtacgt gtttatctgg |
| 3781 | agaactgtgg aagcctgtcc cgttgtcaga gtggaagggg acaactgtga ggtgaaagac |
| 3841 | ccaaggcatg gcaacttgta tgacctgaag ccccctgggcc tcaacgacac catcgtgagc |
| 3901 | gctggcgaat acacttatta cttccgggtc tgtgggaagc tttcctcaga cgtctgcccc |
| 3961 | acaagtgaca agtccaaggt ggtctcctca tgtcaggaaa agcgggaacc gcagggattt |
| 4021 | cacaaagtgg caggtctcct gactcagaag ctaacttatg aaaatggctt gttaaaaatg |
| 4081 | aacttcacgg ggggggacac ttgccataag gtttatcagc gctccacagc catcttcttc |
| 4141 | tactgtgacc gcggcaccca gcggccagta tttctaaagg agacttcaga ttgttcctac |
| 4201 | ttgtttgagt ggcgaacgca gtatgcctgc ccacctttcg atctgactga atgttcattc |
| 4261 | aaagatgggg ctggcaactc cttcgacctc tcgtccctgt caaggtacag tgacaactgg |
| 4321 | gaagccatca ctgggacggg gacccggga cactacctca tcaatgtctg caagtctctg |
| 4381 | gccccgcagg ctggcactga gccgtgccct ccagaagcag ccgcgtgtct gctgggtggc |

-continued

| | Sequences |
|---|---|
| 4441 | tccaagcccg tgaacctcgg cagggtaagg gacggacctc agtggagaga tggcataatt |
| 4501 | gtcctgaaat acgttgatgg cgacttatgt ccagatggga ttcggaaaaa gtcaaccacc |
| 4561 | atccgattca cctgcagcga gagccaagtg aactccaggc ccatgttcat cagcgccgtg |
| 4621 | gaggactgtg agtacacctt tgcctggccc acagccacag cctgtcccat gaagagcaac |
| 4681 | gagcatgatg actgccaggt caccaaccca agcacaggac acctgtttga tctgagctcc |
| 4741 | ttaagtggca gggcgggatt cacagctgct tacagcgaga aggggttggt ttacatgagc |
| 4801 | atctgtgggg agaatgaaaa ctgccctcct ggcgtggggg cctgctttgg acagaccagg |
| 4861 | attagcgtgg gcaaggccaa caagaggctg agatacgtgg accaggtcct gcagctggtg |
| 4921 | tacaaggatg ggtccccttg tccctccaaa tccggcctga gctataagag tgtgatcagt |
| 4981 | ttcgtgtgca ggcctgaggc cgggccaacc aataggccca tgctcatctc cctggacaag |
| 5041 | cagacatgca ctctcttctt ctcctggcac acgccgctgg cctgcgagca agcgaccgaa |
| 5101 | tgttccgtga ggaatggaag ctctattgtt gacttgtctc cccttattca tcgcactggt |
| 5161 | ggttatgagg cttatgatga gagtgaggat gatgcctccg ataccaaccc tgatttctac |
| 5221 | atcaatattt gtcagccact aaatcccatg cacgcagtgc cctgtcctgc cggagccgct |
| 5281 | gtgtgcaaag ttcctattga tggtccccc atagatatcg gccgggtagc aggaccacca |
| 5341 | atactcaatc caatagcaaa tgagatttac ttgaattttg aaagcagtac tccttgctta |
| 5401 | gcggacaagc atttcaacta cacctcgctc atcgcgtttc actgtaagag aggtgtgagc |
| 5461 | atgggaacgc ctaagctgtt aaggaccagc gagtgcgact ttgtgttcga atgggagact |
| 5521 | cctgtcgtct gtcctgatga agtgaggatg gatggctgta ccctgacaga tgagcagctc |
| 5581 | ctctacagct tcaacttgtc cagccttttcc acgagcacct ttaaggtgac tcgcgactcg |
| 5641 | cgcacctaca gcgttggggt gtgcaccttt gcagtcgggc cagaacaagg aggctgtaag |
| 5701 | gacggaggag tctgtctgct ctcaggcacc aaggggggcat cctttggacg gctgcaatca |
| 5761 | atgaaactgg attacaggca ccaggatgaa gcggtcgttt taagttacgt gaatggtgat |
| 5821 | cgttgccctc cagaaaccga tgacggcgtc ccctgtgtct tcccttcat attcaatggg |
| 5881 | aagagctacg aggagtgcat catagagagc agggcgaagc tgtggtgtag cacaactgcg |
| 5941 | gactacgaca gagaccacga gtggggcttc tgcagacact caaacagcta ccggacatcc |
| 6001 | agcatcatat ttaagtgtga tgaagatgag gacattggga ggccacaagt cttcagtgaa |
| 6061 | gtgcgtgggt gtgatgtgac atttgagtgg aaaacaaaag ttgtctgccc tccaaagaag |
| 6121 | ttggagtgca aattcgtcca gaaacacaaa acctacgacc tgcggctgct ctcctctctc |
| 6181 | accgggtcct ggtccctggt ccacaacgga gtctcgtact atataaatct gtgccagaaa |
| 6241 | atatataaag ggcccctggg ctgctctgaa agggccagca tttgcagaag gaccacaact |
| 6301 | ggtgacgtcc aggtcctggg actcgttcac acgcagaagc tgggtgtcat aggtgacaaa |
| 6361 | gttgttgtca cgtactccaa aggttatccg tgtggtggaa ataagaccgc atcctccgtg |
| 6421 | atagaattga cctgtacaaa gacggtgggc agacctgcat tcaagaggtt tgatatcgac |
| 6481 | agctgcactt actacttcag ctgggactcc cgggctgcct gcgccgtgaa gcctcaggag |
| 6541 | gtgcagatgg tgaatgggac catcaccaac cctataaatg caagagctt cagcctcgga |
| 6601 | gatatttatt ttaagctgtt cagagcctct ggggacatga ggaccaatgg ggacaactac |
| 6661 | ctgtatgaga tccaactttc ctccatcaca agctccagaa acccggcgtg ctctggagcc |

-continued

| | Sequences |
|---|---|
| 6721 | aacatatgcc aggtgaagcc caacgatcag cacttcagtc ggaaagttgg aacctctgac |
| 6781 | aagaccaagt actaccttca agacggcgat ctcgatgtcg tgtttgcctc ttcctctaag |
| 6841 | tgcggaaagg ataagaccaa gtctgtttct tccaccatct tcttccactg tgaccctctg |
| 6901 | gtggaggacg ggatccccga gttcagtcac gagactgccg actgccagta cctcttctct |
| 6961 | tggtacacct cagccgtgtg tcctctgggg gtgggctttg acagcgagaa tcccggggac |
| 7021 | gacgggcaga tgcacaaggg gctgtcagaa cggagccagg cagtcggcgc ggtgctcagc |
| 7081 | ctgctgctgg tggcgctcac ctgctgcctg ctggccctgt tgctctacaa gaaggagagg |
| 7141 | agggaaacag tgataagtaa gctgaccact tgctgtagga gaagttccaa cgtgtcctac |
| 7201 | aaatactcaa aggtgaataa ggaagaagag acagatgaga atgaaacaga gtggctgatg |
| 7261 | gaagagatcc agctgcctcc tccacggcag ggaaaggaag ggcaggagaa cggccatatt |
| 7321 | accaccaagt cagtgaaagc cctcagctcc ctgcatgggg atgaccagga cagtgaggat |
| 7381 | gaggttctga ccatcccaga ggtgaaagtt cactcgggca ggggagctgg ggcagagagc |
| 7441 | tcccacccag tgagaaacgc acagagcaat gcccttcagg agcgtgagga cgatagggtg |
| 7501 | gggctggtca ggggtgagaa ggcgaggaaa gggaagtcca gctctgcaca gcagaagaca |
| 7561 | gtgagctcca ccaagctggt gtccttccat gacgcagcg acgaggacct cttacacatc |
| 7621 | tgactccgca gtgcctgcag gggagcacgg agccgcggga cagccaagca cctccaacca |
| 7681 | aataagactt ccactcgatg atgcttctat aattttgcct ttaacagaaa cttctcaaaag |
| 7741 | ggaagagttt ttgtgatggg ggagagggtg aaggaggtca ggccccactc cttcctgatt |
| 7801 | gtttacagtc attggaataa ggcatggctc agatcggcca cagggcggta ccttgtgccc |
| 7861 | agggttttgc cccaagtcct catttaaaag cataaggccg gacgcatctc aaaacagagg |
| 7921 | gctgcattcg aagaaaccct tgctgcttta gtcccgatag ggtatttgac cccgatatat |
| 7981 | tttagcattt taattctctc ccctatttta ttgactttga caattactca ggtttgagaa |
| 8041 | aaaggaaaaa aaaacagcca ccgtttcttc ctgccagcag gggtgtgatg taccagtttg |
| 8101 | tccatcttga gatggtgagg ctgtcagtgt atggggcagc ttccggcggg atgttgaact |
| 8161 | ggtcattaat gtgtcccctg agttggagct cattctgtct cttttctctt ttgctttctg |
| 8221 | tttcttaagg gcacacacac gtgcgtgcga gcacacacac acatacgtgc acagggtccc |
| 8281 | cgagtgccta ggttttggag agtttgcctg ttctatgcct ttagtcagga atggctgcac |
| 8341 | cttttttgcat gatatcttca agcctgggcg tacagagcac atttgtcagt attttttgccg |
| 8401 | gctggtgaat tcaaacaacc tgcccaaaga ttgatttgtg tgtttgtgtg tgtgtgtgtg |
| 8461 | tgtgtgtgtg tgtgtgagtg gagttgaggt gtcagagaaa atgaattttt tccagatttg |
| 8521 | gggtataggt ctcatctctt caggttctca tgataccacc tttactgtgc ttattttttt |
| 8581 | aagaaaaaag tgttgatcaa ccattcgacc tataagaagc cttaatttgc acagtgtgtg |
| 8641 | acttacagaa actgcatgaa aaatcatggg ccagagcctc ggccctagca ttgcacttgg |
| 8701 | cctcatgctg gagggaggct gggcgggtac agcgcggagg aggagggagg ccaggcgggc |
| 8761 | atggcgtgga ggaggaggga ggccgggcgg tcacagcatg gaggaggagg gaggcgctgc |
| 8821 | tggtgttctt attctggcgg cagcgccttt cctgccatgt ttagtgaatg acttttctcg |
| 8881 | cattgtagaa ttgtatatag actctggtgt tctattgctg agaagcaaac cgccctgcag |

| | Sequences |
|---|---|
| 8941 | catccctcag cctgtaccgg tttggctggc ttgtttgatt tcaacatgag tgtatttttt |
| 9001 | aaaattgatt tttctcttca ttttttttc aatcaacttt actgtaatat aaagtattca |
| 9061 | acaatttcaa taaagataa attattaaaa |

SEQ ID NO: 2 Human IGF2R coding sequence

```
  1    nehddcqvtn pstghlfdls slsgragfta aysekglvym sicgenencp pgvgacfgqt
 61    risvgkankr lryvdqvlql vykdgspcps ksglsyksvi sfvcrpeagp tnrpmlisld
121    kqtctlffsw htplacegat
```

SEQ ID NO: 3 Human IGF2R domain 11

---

The invention claimed is:

1. A mutant IGF2 binding domain comprising the amino acid sequence of residues 1511 to 1650 of human IGF2R (SEQ ID NO: 1) with residue P1597 of said amino acid sequence substituted for H or K and either;

(i) residue E1544 substituted for K, residue K1545 substituted for S, and residue L1547 substituted for V; or (ii) residue S1543 substituted for A, residue E1544 substituted for K, residue K1545 substituted for G, residue G1546 substituted for W, and residue L1547 substituted for G.

2. A mutant IGF2 binding domain according to claim 1 wherein residue P1597 of said amino acid sequence is substituted for H.

3. A mutant IGF2 binding domain according to claim 1 wherein residue P1597 of said amino acid sequence is substituted for K.

4. A polypeptide comprising two or more mutant IGF2 binding domains according to claim 1.

5. A polypeptide comprising a mutant IGF2 binding domain according to claim 1 and domain 13 of human IGF2R.

6. A polypeptide comprising a mutant IGF2 binding domain according to claim 1 and an immunoglobulin Fc domain.

7. A polypeptide comprising a mutant IGF2 binding domain according to claim 1 and an affinity tag.

8. A pharmaceutical composition comprising a mutant IGF2 binding domain according to claim 1 and a pharmaceutically acceptable carrier.

9. A method of producing a pharmaceutical composition comprising;

admixing a mutant IGF2 binding domain according to claim 1 with a pharmaceutically acceptable excipient.

10. A mutant IGF2 binding domain comprising the amino acid sequence of residues 1511 to 1650 of human IGF2R (SEQ ID NO: 1) with residue P1597 of said amino acid sequence substituted for H; residue E1544 substituted for K, residue K1545 substituted for S, and residue L1547 substituted for V.

* * * * *

SEQUENCE LISTING

<160> NUMBER OF SEQ ID NOS: 22

<210> SEQ ID NO 1
<211> LENGTH: 2491
<212> TYPE: PRT
<213> ORGANISM: Artificial Sequence
<220> FEATURE:
<223> OTHER INFORMATION: Human IGF2R sequence variant

<400> SEQUENCE: 1

```
Met Gly Ala Ala Ala Gly Arg Ser Pro His Leu Gly Pro Ala Pro Ala
1               5                   10                  15

Arg Arg Pro Gln Arg Ser Leu Leu Leu Gln Leu Leu Leu Leu Leu Val
            20                  25                  30

Ala Ala Pro Gly Ser Thr Gln Ala Gln Ala Ala Pro Phe Pro Glu Leu
        35                  40                  45

Cys Ser Tyr Thr Trp Glu Ala Val Asp Thr Lys Asn Asn Val Leu Tyr
    50                  55                  60

Lys Ile Asn Ile Cys Gly Ser Val Asp Ile Val Gln Cys Gly Pro Ser
65                  70                  75                  80

Ser Ala Val Cys Met His Asp Leu Lys Thr Arg Thr Tyr His Ser Val
                85                  90                  95

Gly Asp Ser Val Leu Arg Ser Ala Thr Arg Ser Leu Leu Glu Phe Asn
            100                 105                 110

Thr Thr Val Ser Cys Asp Gln Gln Gly Thr Asn His Arg Val Gln Ser
        115                 120                 125

Ser Ile Ala Phe Leu Cys Gly Lys Thr Leu Gly Thr Pro Glu Phe Val
    130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
                165                 170                 175

Phe Asp Glu Glu Leu Arg Lys His Asp Leu Asn Pro Leu Ile Lys Leu
            180                 185                 190

Ser Gly Ala Tyr Leu Val Asp Asp Ser Asp Pro Asp Thr Ser Leu Phe
        195                 200                 205

Ile Asn Val Cys Arg Asp Ile Asp Thr Leu Arg Asp Pro Gly Ser Gln
    210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
```

```
                245                 250                 255
Lys Asp Arg Leu Val Leu Ser Tyr Val Arg Glu Glu Ala Gly Lys Leu
            260                 265                 270

Asp Phe Cys Asp Gly His Ser Pro Ala Val Thr Ile Thr Phe Val Cys
        275                 280                 285

Pro Ser Glu Arg Arg Glu Gly Thr Ile Pro Lys Leu Thr Ala Lys Ser
290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
            340                 345                 350

Ile Ser Asp Gly Lys Glu Tyr Leu Phe Tyr Leu Asn Val Cys Gly Glu
        355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
        435                 440                 445

Thr Gly Glu Val Asp Cys Thr Tyr Phe Phe Thr Trp Asp Thr Glu Tyr
    450                 455                 460

Ala Cys Val Lys Glu Lys Glu Asp Leu Leu Cys Gly Ala Thr Asp Gly
465                 470                 475                 480

Lys Lys Arg Tyr Asp Leu Ser Ala Leu Val Arg His Ala Glu Pro Glu
                485                 490                 495

Gln Asn Trp Glu Ala Val Asp Gly Ser Gln Thr Glu Thr Glu Lys Lys
            500                 505                 510

His Phe Phe Ile Asn Ile Cys His Arg Val Leu Gln Glu Gly Lys Ala
        515                 520                 525

Arg Gly Cys Pro Glu Asp Ala Ala Val Cys Ala Val Asp Lys Asn Gly
    530                 535                 540

Ser Lys Asn Leu Gly Lys Phe Ile Ser Ser Pro Met Lys Glu Lys Gly
545                 550                 555                 560

Asn Ile Gln Leu Ser Tyr Ser Asp Gly Asp Asp Cys Gly His Gly Lys
                565                 570                 575

Lys Ile Lys Thr Asn Ile Thr Leu Val Cys Lys Pro Gly Asp Leu Glu
            580                 585                 590

Ser Ala Pro Val Leu Arg Thr Ser Glu Gly Gly Cys Phe Tyr Glu
        595                 600                 605

Phe Glu Trp Arg Thr Ala Ala Ala Cys Val Leu Ser Lys Thr Glu Gly
    610                 615                 620

Glu Asn Cys Thr Val Phe Asp Ser Gln Ala Gly Phe Ser Phe Asp Leu
625                 630                 635                 640

Ser Pro Leu Thr Lys Lys Asn Gly Ala Tyr Lys Val Glu Thr Lys Lys
                645                 650                 655

Tyr Asp Phe Tyr Ile Asn Val Cys Gly Pro Val Ser Val Ser Pro Cys
            660                 665                 670
```

-continued

```
Gln Pro Asp Ser Gly Ala Cys Gln Val Ala Lys Ser Asp Glu Lys Thr
        675                 680                 685
Trp Asn Leu Gly Leu Ser Asn Ala Lys Leu Ser Tyr Tyr Asp Gly Met
        690                 695                 700
Ile Gln Leu Asn Tyr Arg Gly Gly Thr Pro Tyr Asn Asn Glu Arg His
705                 710                 715                 720
Thr Pro Arg Ala Thr Leu Ile Thr Phe Leu Cys Asp Arg Asp Ala Gly
                725                 730                 735
Val Gly Phe Pro Glu Tyr Gln Glu Glu Asp Asn Ser Thr Tyr Asn Phe
                740                 745                 750
Arg Trp Tyr Thr Ser Tyr Ala Cys Pro Glu Glu Pro Leu Glu Cys Val
        755                 760                 765
Val Thr Asp Pro Ser Thr Leu Glu Gln Tyr Asp Leu Ser Ser Leu Ala
        770                 775                 780
Lys Ser Glu Gly Gly Leu Gly Gly Asn Trp Tyr Ala Met Asp Asn Ser
785                 790                 795                 800
Gly Glu His Val Thr Trp Arg Lys Tyr Tyr Ile Asn Val Cys Arg Pro
                805                 810                 815
Leu Asn Pro Val Pro Gly Cys Asn Arg Tyr Ala Ser Ala Cys Gln Met
                820                 825                 830
Lys Tyr Glu Lys Asp Gln Gly Ser Phe Thr Glu Val Val Ser Ile Ser
        835                 840                 845
Asn Leu Gly Met Ala Lys Thr Gly Pro Val Val Glu Asp Ser Gly Ser
850                 855                 860
Leu Leu Leu Glu Tyr Val Asn Gly Ser Ala Cys Thr Thr Ser Asp Gly
865                 870                 875                 880
Arg Gln Thr Thr Tyr Thr Thr Arg Ile His Leu Val Cys Ser Arg Gly
                885                 890                 895
Arg Leu Asn Ser His Pro Ile Phe Ser Leu Asn Trp Glu Cys Val Val
                900                 905                 910
Ser Phe Leu Trp Asn Thr Glu Ala Ala Cys Pro Ile Gln Thr Thr Thr
        915                 920                 925
Asp Thr Asp Gln Ala Cys Ser Ile Arg Asp Pro Asn Ser Gly Phe Val
        930                 935                 940
Phe Asn Leu Asn Pro Leu Asn Ser Ser Gln Gly Tyr Asn Val Ser Gly
945                 950                 955                 960
Ile Gly Lys Ile Phe Met Phe Asn Val Cys Gly Thr Met Pro Val Cys
                965                 970                 975
Gly Thr Ile Leu Gly Lys Pro Ala Ser Gly Cys Glu Ala Glu Thr Gln
                980                 985                 990
Thr Glu Glu Leu Lys Asn Trp Lys Pro Ala Arg Pro Val Gly Ile Glu
        995                 1000                1005
Lys Ser Leu Gln Leu Ser Thr Glu Gly Phe Ile Thr Leu Thr Tyr
        1010                1015                1020
Lys Gly Pro Leu Ser Ala Lys Gly Thr Ala Asp Ala Phe Ile Val
        1025                1030                1035
Arg Phe Val Cys Asn Asp Asp Val Tyr Ser Gly Pro Leu Lys Phe
        1040                1045                1050
Leu His Gln Asp Ile Asp Ser Gly Gln Gly Ile Arg Asn Thr Tyr
        1055                1060                1065
Phe Glu Phe Glu Thr Ala Leu Ala Cys Val Pro Ser Pro Val Asp
        1070                1075                1080
```

-continued

```
Cys Gln Val Thr Asp Leu Ala Gly Asn Glu Tyr Asp Leu Thr Gly
    1085                1090                1095

Leu Ser Thr Val Arg Lys Pro Trp Thr Ala Val Asp Thr Ser Val
    1100                1105                1110

Asp Gly Arg Lys Arg Thr Phe Tyr Leu Ser Val Cys Asn Pro Leu
    1115                1120                1125

Pro Tyr Ile Pro Gly Cys Gln Gly Ser Ala Val Gly Ser Cys Leu
    1130                1135                1140

Val Ser Glu Gly Asn Ser Trp Asn Leu Gly Val Val Gln Met Ser
    1145                1150                1155

Pro Gln Ala Ala Ala Asn Gly Ser Leu Ser Ile Met Tyr Val Asn
    1160                1165                1170

Gly Asp Lys Cys Gly Asn Gln Arg Phe Ser Thr Arg Ile Thr Phe
    1175                1180                1185

Glu Cys Ala Gln Ile Ser Gly Ser Pro Ala Phe Gln Leu Gln Asp
    1190                1195                1200

Gly Cys Glu Tyr Val Phe Ile Trp Arg Thr Val Glu Ala Cys Pro
    1205                1210                1215

Val Val Arg Val Glu Gly Asp Asn Cys Glu Val Lys Asp Pro Arg
    1220                1225                1230

His Gly Asn Leu Tyr Asp Leu Lys Pro Leu Gly Leu Asn Asp Thr
    1235                1240                1245

Ile Val Ser Ala Gly Glu Tyr Thr Tyr Tyr Phe Arg Val Cys Gly
    1250                1255                1260

Lys Leu Ser Ser Asp Val Cys Pro Thr Ser Asp Lys Ser Lys Val
    1265                1270                1275

Val Ser Ser Cys Gln Glu Lys Arg Glu Pro Gln Gly Phe His Lys
    1280                1285                1290

Val Ala Gly Leu Leu Thr Gln Lys Leu Thr Tyr Glu Asn Gly Leu
    1295                1300                1305

Leu Lys Met Asn Phe Thr Gly Gly Asp Thr Cys His Lys Val Tyr
    1310                1315                1320

Gln Arg Ser Thr Ala Ile Phe Phe Tyr Cys Asp Arg Gly Thr Gln
    1325                1330                1335

Arg Pro Val Phe Leu Lys Glu Thr Ser Asp Cys Ser Tyr Leu Phe
    1340                1345                1350

Glu Trp Arg Thr Gln Tyr Ala Cys Pro Pro Phe Asp Leu Thr Glu
    1355                1360                1365

Cys Ser Phe Lys Asp Gly Ala Gly Asn Ser Phe Asp Leu Ser Ser
    1370                1375                1380

Leu Ser Arg Tyr Ser Asp Asn Trp Glu Ala Ile Thr Gly Thr Gly
    1385                1390                1395

Asp Pro Glu His Tyr Leu Ile Asn Val Cys Lys Ser Leu Ala Pro
    1400                1405                1410

Gln Ala Gly Thr Glu Pro Cys Pro Pro Glu Ala Ala Ala Cys Leu
    1415                1420                1425

Leu Gly Gly Ser Lys Pro Val Asn Leu Gly Arg Val Arg Asp Gly
    1430                1435                1440

Pro Gln Trp Arg Asp Gly Ile Ile Val Leu Lys Tyr Val Asp Gly
    1445                1450                1455

Asp Leu Cys Pro Asp Gly Ile Arg Lys Lys Ser Thr Thr Ile Arg
    1460                1465                1470

Phe Thr Cys Ser Glu Ser Gln Val Asn Ser Arg Pro Met Phe Ile
```

-continued

```
            1475                1480                1485

Ser Ala Val Glu Asp Cys Glu Tyr Thr Phe Ala Trp Pro Thr Ala
    1490                1495                1500

Thr Ala Cys Pro Met Lys Ser Asn Glu His Asp Cys Gln Val
    1505                1510                1515

Thr Asn Pro Ser Thr Gly His Leu Phe Asp Leu Ser Ser Leu Ser
    1520                1525                1530

Gly Arg Ala Gly Phe Thr Ala Ala Tyr Ser Glu Lys Gly Leu Val
    1535                1540                1545

Tyr Met Ser Ile Cys Gly Glu Asn Glu Asn Cys Pro Pro Gly Val
    1550                1555                1560

Gly Ala Cys Phe Gly Gln Thr Arg Ile Ser Val Gly Lys Ala Asn
    1565                1570                1575

Lys Arg Leu Arg Tyr Val Asp Gln Val Leu Gln Leu Val Tyr Lys
    1580                1585                1590

Asp Gly Ser Pro Cys Pro Ser Lys Ser Gly Leu Ser Tyr Lys Ser
    1595                1600                1605

Val Ile Ser Phe Val Cys Arg Pro Glu Ala Gly Pro Thr Asn Arg
    1610                1615                1620

Pro Met Leu Ile Ser Leu Asp Lys Gln Thr Cys Thr Leu Phe Phe
    1625                1630                1635

Ser Trp His Thr Pro Leu Ala Cys Glu Gln Ala Thr Glu Cys Ser
    1640                1645                1650

Val Arg Asn Gly Ser Ser Ile Val Asp Leu Ser Pro Leu Ile His
    1655                1660                1665

Arg Thr Gly Gly Tyr Glu Ala Tyr Asp Glu Ser Glu Asp Asp Ala
    1670                1675                1680

Ser Asp Thr Asn Pro Asp Phe Tyr Ile Asn Ile Cys Gln Pro Leu
    1685                1690                1695

Asn Pro Met His Ala Val Pro Cys Pro Ala Gly Ala Ala Val Cys
    1700                1705                1710

Lys Val Pro Ile Asp Gly Pro Pro Ile Asp Ile Gly Arg Val Ala
    1715                1720                1725

Gly Pro Pro Ile Leu Asn Pro Ile Ala Asn Glu Ile Tyr Leu Asn
    1730                1735                1740

Phe Glu Ser Ser Thr Pro Cys Leu Ala Asp Lys His Phe Asn Tyr
    1745                1750                1755

Thr Ser Leu Ile Ala Phe His Cys Lys Arg Gly Val Ser Met Gly
    1760                1765                1770

Thr Pro Lys Leu Leu Arg Thr Ser Glu Cys Asp Phe Val Phe Glu
    1775                1780                1785

Trp Glu Thr Pro Val Val Cys Pro Asp Glu Val Arg Met Asp Gly
    1790                1795                1800

Cys Thr Leu Thr Asp Glu Gln Leu Leu Tyr Ser Phe Asn Leu Ser
    1805                1810                1815

Ser Leu Ser Thr Ser Thr Phe Lys Val Thr Arg Asp Ser Arg Thr
    1820                1825                1830

Tyr Ser Val Gly Val Cys Thr Phe Ala Val Gly Pro Glu Gln Gly
    1835                1840                1845

Gly Cys Lys Asp Gly Gly Val Cys Leu Leu Ser Gly Thr Lys Gly
    1850                1855                1860

Ala Ser Phe Gly Arg Leu Gln Ser Met Lys Leu Asp Tyr Arg His
    1865                1870                1875
```

-continued

```
Gln Asp Glu Ala Val Val Leu Ser Tyr Val Asn Gly Asp Arg Cys
    1880            1885                1890

Pro Pro Glu Thr Asp Asp Gly Val Pro Cys Val Phe Pro Phe Ile
    1895            1900                1905

Phe Asn Gly Lys Ser Tyr Glu Glu Cys Ile Ile Glu Ser Arg Ala
    1910            1915                1920

Lys Leu Trp Cys Ser Thr Thr Ala Asp Tyr Asp Arg Asp His Glu
    1925            1930                1935

Trp Gly Phe Cys Arg His Ser Asn Ser Tyr Arg Thr Ser Ser Ile
    1940            1945                1950

Ile Phe Lys Cys Asp Glu Asp Glu Asp Ile Gly Arg Pro Gln Val
    1955            1960                1965

Phe Ser Glu Val Arg Gly Cys Asp Val Thr Phe Glu Trp Lys Thr
    1970            1975                1980

Lys Val Val Cys Pro Pro Lys Lys Leu Glu Cys Lys Phe Val Gln
    1985            1990                1995

Lys His Lys Thr Tyr Asp Leu Arg Leu Leu Ser Ser Leu Thr Gly
    2000            2005                2010

Ser Trp Ser Leu Val His Asn Gly Val Ser Tyr Tyr Ile Asn Leu
    2015            2020                2025

Cys Gln Lys Ile Tyr Lys Gly Pro Leu Gly Cys Ser Glu Arg Ala
    2030            2035                2040

Ser Ile Cys Arg Arg Thr Thr Thr Gly Asp Val Gln Val Leu Gly
    2045            2050                2055

Leu Val His Thr Gln Lys Leu Gly Val Ile Gly Asp Lys Val Val
    2060            2065                2070

Val Thr Tyr Ser Lys Gly Tyr Pro Cys Gly Gly Asn Lys Thr Ala
    2075            2080                2085

Ser Ser Val Ile Glu Leu Thr Cys Thr Lys Thr Val Gly Arg Pro
    2090            2095                2100

Ala Phe Lys Arg Phe Asp Ile Asp Ser Cys Thr Tyr Tyr Phe Ser
    2105            2110                2115

Trp Asp Ser Arg Ala Ala Cys Ala Val Lys Pro Gln Glu Val Gln
    2120            2125                2130

Met Val Asn Gly Thr Ile Thr Asn Pro Ile Asn Gly Lys Ser Phe
    2135            2140                2145

Ser Leu Gly Asp Ile Tyr Phe Lys Leu Phe Arg Ala Ser Gly Asp
    2150            2155                2160

Met Arg Thr Asn Gly Asp Asn Tyr Leu Tyr Glu Ile Gln Leu Ser
    2165            2170                2175

Ser Ile Thr Ser Ser Arg Asn Pro Ala Cys Ser Gly Ala Asn Ile
    2180            2185                2190

Cys Gln Val Lys Pro Asn Asp Gln His Phe Ser Arg Lys Val Gly
    2195            2200                2205

Thr Ser Asp Lys Thr Lys Tyr Tyr Leu Gln Asp Gly Asp Leu Asp
    2210            2215                2220

Val Val Phe Ala Ser Ser Ser Lys Cys Gly Lys Asp Lys Thr Lys
    2225            2230                2235

Ser Val Ser Ser Thr Ile Phe Phe His Cys Asp Pro Leu Val Glu
    2240            2245                2250

Asp Gly Ile Pro Glu Phe Ser His Glu Thr Ala Asp Cys Gln Tyr
    2255            2260                2265
```

| | | | | | | | | | | | |
|---|---|---|---|---|---|---|---|---|---|---|---|
| Leu | Phe | Ser | Trp | Tyr | Thr | Ser | Ala | Val | Cys | Pro | Leu | Gly | Val | Gly |
| 2270 | | | | | 2275 | | | | | 2280 | |

Leu Phe Ser Trp Tyr Thr Ser Ala Val Cys Pro Leu Gly Val Gly
2270                2275              2280

Phe Asp Ser Glu Asn Pro Gly Asp Asp Gly Gln Met His Lys Gly
2285                2290              2295

Leu Ser Glu Arg Ser Gln Ala Val Gly Ala Val Leu Ser Leu Leu
2300                2305              2310

Leu Val Ala Leu Thr Cys Cys Leu Leu Ala Leu Leu Leu Tyr Lys
2315                2320              2325

Lys Glu Arg Arg Glu Thr Val Ile Ser Lys Leu Thr Thr Cys Cys
2330                2335              2340

Arg Arg Ser Ser Asn Val Ser Tyr Lys Tyr Ser Lys Val Asn Lys
2345                2350              2355

Glu Glu Glu Thr Asp Glu Asn Glu Thr Glu Trp Leu Met Glu Glu
2360                2365              2370

Ile Gln Leu Pro Pro Pro Arg Gln Gly Lys Glu Gly Gln Glu Asn
2375                2380              2385

Gly His Ile Thr Thr Lys Ser Val Lys Ala Leu Ser Ser Leu His
2390                2395              2400

Gly Asp Asp Gln Asp Ser Glu Asp Glu Val Leu Thr Ile Pro Glu
2405                2410              2415

Val Lys Val His Ser Gly Arg Gly Ala Gly Ala Glu Ser Ser His
2420                2425              2430

Pro Val Arg Asn Ala Gln Ser Asn Ala Leu Gln Glu Arg Glu Asp
2435                2440              2445

Asp Arg Val Gly Leu Val Arg Gly Glu Lys Ala Arg Lys Gly Lys
2450                2455              2460

Ser Ser Ser Ala Gln Gln Lys Thr Val Ser Ser Thr Lys Leu Val
2465                2470              2475

Ser Phe His Asp Asp Ser Asp Glu Asp Leu Leu His Ile
2480                2485              2490

<210> SEQ ID NO 2
<211> LENGTH: 9090
<212> TYPE: DNA
<213> ORGANISM: Artificial Sequence
<220> FEATURE:
<223> OTHER INFORMATION: Human IGF2R sequence variant

<400> SEQUENCE: 2

```
cgagcccagt cgagccgcgc tcacctcggg ctcccgctcc gtctccacct ccgcctttgc    60
cctggcggcg cgaccccgtc ccggcgcggc cccccagcagt cgcgcgccgt tagcctcgcg    120
cccgccgcgc agtccgggcc cggcgcgatg ggggccgccg ccggccggag cccccacctg    180
gggcccgcgc ccgccgccg cccgcagcgc tctctgctcc tgctgcagct gctgctgctc    240
gtcgctgccc cggggtccac gcaggcccag gccgccccgt tccccgagct gtgcagttat    300
acatgggaag ctgttgatac caaaaataat gtactttata aaatcaacat ctgtggaagt    360
gtggatattg tccagtgcgg gccatcaagt gctgtttgta tgcacgactt gaagacacgc    420
acttatcatt cagtgggtga ctctgttttg agaagtgcaa ccagatctct cctggaattc    480
aacacaacag tgagctgtga ccagcaaggc acaaatcaca gagtccagag cagcattgcc    540
ttcctgtgtg ggaaaaccct gggaactcct gaatttgtaa ctgcaacaga atgtgtgcac    600
tactttgagt ggaggaccac tgcagcctgc aagaaagaca tatttaaagc aaataaggag    660
gtgccatgct atgtgtttga tgaagagttg aggaagcatg atctcaatcc tctgatcaag    720
```

```
cttagtggtg cctacttggt ggatgactcc gatccggaca cttctctatt catcaatgtt    780
tgtagagaca tagacacact acgagaccca ggttcacagc tgcgggcctg tcccccggc     840
actgccgcct gcctggtaag aggacaccag gcgtttgatg ttggccagcc ccgggacgga    900
ctgaagctgg tgcgcaagga caggcttgtc ctgagttacg tgagggaaga ggcaggaaag    960
ctagactttt gtgatggtca cagccctgcg gtgactatta catttgtttg cccgtcggag   1020
cggagagagg gcaccattcc caaactcaca gctaaatcca actgccgcta tgaaattgag   1080
tggattactg agtatgcctg ccacagagat tacctggaaa gtaaaacttg ttctctgagc   1140
ggcgagcagc aggatgtctc catagacctc acaccacttg cccagagcgg aggttcatcc   1200
tatatttcag atggaaaaga atatttgttt tatttgaatg tctgtggaga aactgaaata   1260
cagttctgta ataaaaaaca agctgcagtt tgccaagtga aaagagcga tacctctcaa    1320
gtcaaagcag caggaagata ccacaatcag accctccgat attcggatgg agacctcacc   1380
ttgatatatt ttggaggtga tgaatgcagc tcagggtttc agcggatgag cgtcataaac   1440
tttgagtgca ataaaaccgc aggtaacgat gggaaaggaa ctcctgtatt cacaggggag   1500
gttgactgca cctacttctt cacatgggac acggaatacg cctgtgttaa ggagaaggaa   1560
gacctcctct gcggtgccac cgacgggaag aagcgctatg acctgtccgc gctggtccgc   1620
catgcagaac cagagcagaa ttgggaagct gtggatggca gtcagacgga aacagagaag   1680
aagcattttt tcattaatat ttgtcacaga gtgctgcagg aaggcaaggc acgagggtgt   1740
cccgaggacg cggcagtgtg tgcagtggat aaaaatggaa gtaaaaatct gggaaaattt   1800
atttcctctc ccatgaaaga gaaggaaac attcaactct cttattcaga tggtgatgat   1860
tgtggtcatg gcaagaaaat taaaactaat atcacacttg tatgcaagcc aggtgatctg   1920
gaaagtgcac cagtgttgag aacttctggg gaaggcggtt gcttttatga gtttgagtgg   1980
cgcacagctg cggcctgtgt gctgtctaag acagaagggg agaactgcac ggtctttgac   2040
tcccaggcag ggttttcttt tgacttatca cctctcacaa agaaaaatgg tgcctataaa   2100
gttgagacaa agaagtatga ctttttatata aatgtgtgtg gcccggtgtc tgtgagcccc   2160
tgtcagccag actcaggagc ctgccaggtg gcaaaaagtg atgagaagac ttggaacttg   2220
ggtctgagta atgcgaagct ttcatattat gatgggatga tccaactgaa ctacagaggc   2280
ggcacaccct ataacaatga aagacacaca ccgagagcta cgctcatcac ctttctctgt   2340
gatcgagacg cgggagtggg cttccctgaa tatcaggaag aggataactc cacctacaac   2400
ttccggtggt acaccagcta tgcctgcccg gaggagcccc tggaatgcgt agtgaccgac   2460
ccctccacgc tggagcagta cgacctctcc agtctggcaa aatctgaagg tggccttgga   2520
ggaaactggt atgccatgga caactcaggg gaacatgtca cgtggaggaa atactacatt   2580
aacgtgtgtc ggcctctgaa tccagtgccg ggctgcaacc gatatgcatc ggcttgccag   2640
atgaagtatg aaaagatca gggctccttc actgaagtgg tttccatcag taacttggga   2700
atggcaaaga ccggcccggt ggttgaggac agcggcagcc tccttctgga atacgtgaat   2760
gggtcggcct gcaccaccag cgatggcaga cagaccacat ataccacgag gatccatctc   2820
gtctgctcca ggggcaggct gaacagccac cccatctttt ctctcaactg ggagtgtgtg   2880
gtcagtttcc tgtggaacac agaggctgcc tgtcccattc agacaacgac ggatacagac   2940
caggcttgct ctataaggga tcccaacagt ggatttgtgt ttaatcttaa tccgctaaac   3000
agttcgcaag gatataacgt ctctggcatt gggaagattt ttatgtttaa tgtctgcggc   3060
acaatgcctg tctgtgggac catcctggga aaacctgctt ctggctgtga ggcagaaacc   3120
```

```
caaactgaag agctcaagaa ttggaagcca gcaaggccag tcggaattga gaaaagcctc    3180
cagctgtcca cagagggctt catcactctg acctacaaag ggcctctctc tgccaaaggt    3240
accgctgatg cttttatcgt ccgctttgtt tgcaatgatg atgtttactc agggcccctc    3300
aaattcctgc atcaagatat cgactctggg caagggatcc gaaacactta ctttgagttt    3360
gaaaccgcgt tggcctgtgt tccttctcca gtggactgcc aagtcaccga cctggctgga    3420
aatgagtacg acctgactgg cctaagcaca gtcaggaaac cttggacggc tgttgacacc    3480
tctgtcgatg ggagaaagag gactttctat ttgagcgttt gcaatcctct cccttacatt    3540
cctggatgcc agggcagcgc agtggggtct tgcttagtgt cagaaggcaa tagctggaat    3600
ctgggtgtgg tgcagatgag tccccaagcc gcggcgaatg gatctttgag catcatgtat    3660
gtcaacggtg acaagtgtgg gaaccagcgc ttctccacca ggatcacgtt tgagtgtgct    3720
cagatatcgg gctcaccagc atttcagctt caggatggtt gtgagtacgt gtttatctgg    3780
agaactgtgg aagcctgtcc cgttgtcaga gtggaagggg acaactgtga ggtgaaagac    3840
ccaaggcatg gcaacttgta tgacctgaag cccctgggcc tcaacgacac catcgtgagc    3900
gctggcgaat acacttatta cttccgggtc tgtgggaagc tttcctcaga cgtctgcccc    3960
acaagtgaca agtccaaggt ggtctcctca tgtcaggaaa agcgggaacc gcagggattt    4020
cacaaagtgg caggtctcct gactcagaag ctaacttatg aaaatggctt gttaaaaatg    4080
aacttcacgg ggggggacac ttgccataag gtttatcagc gctccacagc catcttcttc    4140
tactgtgacc gcggcaccca gcggccagta tttctaaagg agacttcaga ttgttcctac    4200
ttgtttgagt ggcgaacgca gtatgcctgc ccaccttttcg atctgactga atgttcattc    4260
aaagatgggg ctggcaactc cttcgacctc tcgtccctgt caaggtacag tgacaactgg    4320
gaagccatca ctgggacggg ggacccggag cactacctca tcaatgtctg caagtctctg    4380
gccccgcagg ctggcactga gccgtgccct ccagaagcag ccgcgtgtct gctgggtggc    4440
tccaagcccg tgaacctcgg cagggtaagg gacggacctc agtggagaga tggcataatt    4500
gtcctgaaat acgttgatgg cgacttatgt ccagatggga ttcggaaaaa gtcaaccacc    4560
atccgattca cctgcagcga gagccaagtg aactccaggc ccatgttcat cagcgccgtg    4620
gaggactgtg agtacacctt tgcctggccc acagccacag cctgtcccat gaagagcaac    4680
gagcatgatg actgccaggt caccaaccca agcacaggac acctgtttga tctgagctcc    4740
ttaagtggca gggcgggatt cacagctgct tacagcgaga aggggttggt ttacatgagc    4800
atctgtgggg agaatgaaaa actgccctcct ggcgtggggg cctgctttgg acagaccagg    4860
attagcgtgg gcaaggccaa caagaggctg agatacgtgg accaggtcct gcagctggtg    4920
tacaaggatg ggtccccttg tccctccaaa tccggcctga gctataagag tgtgatcagt    4980
ttcgtgtgca ggcctgaggc cgggccaacc aataggccca tgctcatctc cctggacaag    5040
cagacatgca ctctcttctt ctcctggcac acgccgctgg cctgcgagca agcgaccgaa    5100
tgttccgtga ggaatggaag ctctattgtt gacttgtctc cccttattca tcgcactggt    5160
ggttatgagg cttatgatga gagtgaggat gatgcctccg ataccaaccc tgatttctac    5220
atcaatattt gtcagccact aaatcccatg cacgcagtgc cctgtcctgc cggagccgct    5280
gtgtgcaaag ttcctattga tggtcccccc atagatatcg gccgggtagc aggaccacca    5340
atactcaatc caatagcaaa tgagatttac ttgaattttg aaagcagtac tccttgctta    5400
gcggacaagc atttcaacta cacctcgctc atcgcgtttc actgtaagag aggtgtgagc    5460
```

```
atgggaacgc ctaagctgtt aaggaccagc gagtgcgact ttgtgttcga atgggagact      5520
cctgtcgtct gtcctgatga agtgaggatg gatggctgta ccctgacaga tgagcagctc      5580
ctctacagct tcaacttgtc cagcctttcc acgagcacct ttaaggtgac tcgcgactcg      5640
cgcacctaca gcgttgggt gtgcacctttt gcagtcgggc cagaacaagg aggctgtaag      5700
gacggaggag tctgtctgct ctcaggcacc aaggggcat cctttggacg gctgcaatca      5760
atgaaactgg attacaggca ccaggatgaa gcggtcgttt taagttacgt gaatggtgat      5820
cgttgccctc agaaaccga tgacggcgtc ccctgtgtct tccccttcat attcaatggg      5880
aagagctacg aggagtgcat catagagagc agggcgaagc tgtggtgtag cacaactgcg      5940
gactacgaca gagaccacga gtggggcttc tgcagacact caaacagcta ccggacatcc      6000
agcatcatat ttaagtgtga tgaagatgag acattggga ggccacaagt cttcagtgaa      6060
gtgcgtgggt gtgatgtgac atttgagtgg aaaacaaaag ttgtctgccc tccaaagaag      6120
ttggagtgca aattcgtcca gaaacacaaa acctacgacc tgcggctgct ctcctctctc      6180
accgggtcct ggtccctggt ccacaacgga gtctcgtact atataaatct gtgccagaaa      6240
atatataaag ggcccctggg ctgctctgaa agggccagca tttgcagaag gaccacaact      6300
ggtgacgtcc aggtcctggg actcgttcac acgcagaagc tgggtgtcat aggtgacaaa      6360
gttgttgtca cgtactccaa aggttatccg tgtggtggaa ataagaccgc atcctccgtg      6420
atagaattga cctgtacaaa gacggtgggc agacctgcat tcaagaggtt tgatatcgac      6480
agctgcactt actacttcag ctgggactcc cgggctgcct gcgccgtgaa gcctcaggag      6540
gtgcagatgg tgaatgggac catcaccaac cctataaatg gcaagagctt cagcctcgga      6600
gatatttatt ttaagctgtt cagagcctct ggggacatga ggaccaatgg gacaactac      6660
ctgtatgaga tccaactttc ctccatcaca agctccagaa accggcgtg ctctggagcc      6720
aacatatgcc aggtgaagcc caacgatcag cacttcagtc ggaaagttgg aacctctgac      6780
aagaccaagt actaccttca agacggcgat ctcgatgtcg tgtttgcctc ttcctctaag      6840
tgcggaaagg ataagaccaa gtctgttct tccaccatct tcttccactg tgaccctctg      6900
gtggaggacg ggatccccga gttcagtcac gagactgccg actgccagta cctcttctct      6960
tggtacacct cagccgtgtg tcctctgggg gtgggctttg acagcgagaa tcccggggac      7020
gacgggcaga tgcacaaggg gctgtcagaa cggagccagg cagtcggcgc ggtgctcagc      7080
ctgctgctgg tggcgctcac ctgctgcctg ctggccctgt tgctctacaa gaaggagagg      7140
agggaaacag tgataagtaa gctgaccact tgctgtagga aagttccaa cgtgtcctac      7200
aaatactcaa aggtgaataa ggaagaagag acagatgaga atgaaacaga gtggctgatg      7260
gaagagatcc agctgcctcc tccacggcag ggaaaggaag ggcaggagaa cggccatatt      7320
accaccaagt cagtgaaagc cctcagctcc ctgcatgggg atgaccagga cagtgaggat      7380
gaggttctga ccatcccaga ggtgaaagtt cactcgggca ggggagctgg ggcagagagc      7440
tcccacccag tgagaaacgc acagagcaat gcccttcagg agcgtgagga cgatagggtg      7500
gggctggtca ggggtgagaa ggcgaggaaa gggaagtcca gctctgcaca gcagaagaca      7560
gtgagctcca ccaagctggt gtccttccat gacgacagcg acgaggacct cttacacatc      7620
tgactccgca gtgcctgcag gggagcacgg agccgcggga cagccaagca cctccaacca      7680
aataagactt ccactcgatg atgcttctat aattttgcct ttaacagaaa cttttcaaaag      7740
ggaagagttt ttgtgatggg ggagagggtg aaggaggtca ggccccactc cttcctgatt      7800
gtttacagtc attggaataa ggcatggctc agatcggcca cagggcggta ccttgtgccc      7860
```

```
agggttttgc cccaagtcct catttaaaag cataaggccg gacgcatctc aaaacagagg   7920
gctgcattcg aagaaaccct tgctgcttta gtcccgatag ggtatttgac cccgatatat   7980
tttagcattt taattctctc cccctattta ttgactttga caattactca ggtttgagaa   8040
aaaggaaaaa aaaacagcca ccgtttcttc ctgccagcag gggtgtgatg taccagtttg   8100
tccatcttga gatggtgagg ctgtcagtgt atggggcagc ttccggcggg atgttgaact   8160
ggtcattaat gtgtcccctg agttggagct cattctgtct ctttctctt ttgctttctg   8220 tttcttaagg gcacacacac gtgcgtgcga gcacacacac acatacgtgc acagggtccc   8280
cgagtgccta ggttttggag agtttgcctg ttctatgcct ttagtcagga atggctgcac   8340 cttttttgcat gatatcttca agcctgggcg tacagagcac atttgtcagt attttttgccg   8400 gctggtgaat tcaaacaacc tgcccaaaga ttgatttgtg tgtttgtgtg tgtgtgtgtg   8460
tgtgtgtgtg tgtgtgagtg gagttgaggt gtcagagaaa atgaattttt tccagatttg   8520
gggtataggt ctcatctctt caggttctca tgataccacc tttactgtgc ttatttttttt   8580 aagaaaaaag tgttgatcaa ccattcgacc tataagaagc cttaatttgc acagtgtgtg   8640
acttacagaa actgcatgaa aaatcatggg ccagagcctc ggccctagca ttgcacttgg   8700
cctcatgctg gagggaggct gggcgggtac agcgcggagg aggagggagg ccaggcgggc   8760
atggcgtgga ggaggaggga ggccgggcgg tcacagcatg gaggaggagg gaggcgctgc   8820
tggtgttctt attctggcgg cagcgccttt cctgccatgt ttagtgaatg acttttctcg   8880
cattgtagaa ttgtatatag actctggtgt tctattgctg agaagcaaac cgccctgcag   8940
catccctcag cctgtaccgg tttggctggc ttgtttgatt tcaacatgag tgtattttt   9000 aaaattgatt tttctcttca tttttttttc aatcaacttt actgtaatat aaagtattca   9060
acaatttcaa taaagataa attattaaaa                                    9090
```

<210> SEQ ID NO 3
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 3

```
Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Glu Lys Gly Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Pro Cys Pro Ser Lys Ser Gly Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140
```

-continued

```
<210> SEQ ID NO 4
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 4

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
             20                  25                  30

Ala Lys Gly Trp Gly Val Tyr Met Ser Ile Cys Gly Glu Asn Glu Asn
         35                  40                  45

Cys Pro Pro Gly Val Gly Ala Cys Phe Gly Arg Thr Arg Ile Ser Val
     50                  55                  60

Gly Lys Ala Asn Lys Arg Leu Arg Tyr Val Asp Gln Val Leu Gln Leu
 65                  70                  75                  80

Val Tyr Lys Asp Gly Ser His Cys Pro Ser Lys His Gly Leu Ser Tyr
                 85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 5
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 5

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
             20                  25                  30

Ala Lys Gly Trp Gly Val Tyr Met Ser Ile Cys Gly Glu Asn Glu Asn
         35                  40                  45

Cys Pro Pro Gly Val Gly Ala Cys Phe Gly Arg Thr Arg Ile Ser Val
     50                  55                  60

Gly Lys Ala Asn Lys Arg Leu Arg Tyr Val Asp Gln Val Leu Gln Leu
 65                  70                  75                  80

Val Tyr Lys Asp Gly Ser Lys Cys Pro Ser Lys His Gly Leu Ser Tyr
                 85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 6
<211> LENGTH: 140
<212> TYPE: PRT
```

```
<213> ORGANISM: Artificial Sequence
<220> FEATURE:
<223> OTHER INFORMATION: Human IGF2R sequence variant

<400> SEQUENCE: 6

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
                20                  25                  30

Ala Lys Gly Trp Gly Val Tyr Met Ser Ile Cys Gly Glu Asn Glu Asn
            35                  40                  45

Cys Pro Pro Gly Val Gly Ala Cys Phe Gly Arg Thr Arg Ile Ser Val
50                  55                  60

Gly Lys Ala Asn Lys Arg Leu Arg Tyr Val Asp Gln Val Leu Gln Leu
65                  70                  75                  80

Val Tyr Lys Asp Gly Ser His Cys Pro Ser Lys Ser Lys Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 7
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 7

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
                20                  25                  30

Ala Lys Gly Trp Gly Val Tyr Met Ser Ile Cys Gly Glu Asn Glu Asn
            35                  40                  45

Cys Pro Pro Gly Val Gly Ala Cys Phe Gly Arg Thr Arg Ile Ser Val
50                  55                  60

Gly Lys Ala Asn Lys Arg Leu Arg Tyr Val Asp Gln Val Leu Gln Leu
65                  70                  75                  80

Val Tyr Lys Asp Gly Ser Lys Cys Pro Ser Lys Ser Lys Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 8
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 8
```

```
Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Lys Ser Gly Val Val Tyr Met Ser Ile Cys Gly Glu Asn Glu Asn
        35                  40                  45

Cys Pro Pro Gly Val Gly Ala Cys Phe Gly Arg Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser His Cys Pro Ser Lys His Gly Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
            115                 120                 125

Ser Trp His Thr Pro Leu Ala Cys Glu Gln Ala Thr
            130                 135                 140
```

<210> SEQ ID NO 9
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 9

```
Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Lys Ser Gly Val Val Tyr Met Ser Ile Cys Gly Glu Asn Glu Asn
        35                  40                  45

Cys Pro Pro Gly Val Gly Ala Cys Phe Gly Arg Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Lys Cys Pro Ser Lys His Gly Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
            115                 120                 125

Ser Trp His Thr Pro Leu Ala Cys Glu Gln Ala Thr
            130                 135                 140
```

<210> SEQ ID NO 10
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 10

```
Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
```

```
                    20                  25                  30
Ser Lys Ser Gly Val Val Tyr Met Ser Ile Cys Gly Glu Asn Glu Asn
            35                  40                  45

Cys Pro Pro Gly Val Gly Ala Cys Phe Gly Arg Thr Arg Ile Ser Val
        50                  55                  60

Gly Lys Ala Asn Lys Arg Leu Arg Tyr Val Asp Gln Val Leu Gln Leu
 65                  70                  75                  80

Val Tyr Lys Asp Gly Ser His Cys Pro Ser Lys His Lys Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 11
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 11

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
                20                  25                  30

Ser Lys Ser Gly Val Val Tyr Met Ser Ile Cys Gly Glu Asn Glu Asn
            35                  40                  45

Cys Pro Pro Gly Val Gly Ala Cys Phe Gly Arg Thr Arg Ile Ser Val
        50                  55                  60

Gly Lys Ala Asn Lys Arg Leu Arg Tyr Val Asp Gln Val Leu Gln Leu
 65                  70                  75                  80

Val Tyr Lys Asp Gly Ser Lys Cys Pro Ser Lys His Lys Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 12
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (33)..(37)
<223> OTHER INFORMATION: Xaa can be any amino acid
<220> FEATURE:
<221> NAME/KEY: VARIANT
<222> LOCATION: (59)..(59)
<223> OTHER INFORMATION: Xaa can be any amino acid
<220> FEATURE:
<221> NAME/KEY: VARIANT
<222> LOCATION: (87)..(87)
<223> OTHER INFORMATION: Xaa can be any amino acid
```

```
<220> FEATURE:
<221> NAME/KEY: VARIANT
<222> LOCATION: (92)..(93)
<223> OTHER INFORMATION: Xaa can be any amino acid
<220> FEATURE:
<221> NAME/KEY: VARIANT
<222> LOCATION: (121)..(121)
<223> OTHER INFORMATION: Xaa can be any amino acid

<400> SEQUENCE: 12

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Xaa Xaa Xaa Xaa Xaa Val Tyr Met Ser Ile Cys Gly Glu Asn Glu Asn
        35                  40                  45

Cys Pro Pro Gly Val Gly Ala Cys Phe Gly Xaa Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Xaa Cys Pro Ser Lys Xaa Xaa Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Xaa Gln Thr Cys Thr Leu Phe Phe
            115                 120                 125

Ser Trp His Thr Pro Leu Ala Cys Glu Gln Ala Thr
            130                 135                 140

<210> SEQ ID NO 13
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (87)..(87)
<223> OTHER INFORMATION: Xaa may be substituted for an uncharged polar
      residue, such as ser, asn or gln, an aliphatic residue such as
      leu, or a basic residue, such as lys, arg or his

<400> SEQUENCE: 13

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Glu Lys Gly Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Xaa Cys Pro Ser Lys Ser Gly Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
            115                 120                 125

Ser Trp His Thr Pro Leu Ala Cys Glu Gln Ala Thr
```

<210> SEQ ID NO 14
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (59)..(59)
<223> OTHER INFORMATION: Xaa may be substitute for a different residue
<220> FEATURE:
<221> NAME/KEY: VARIANT
<222> LOCATION: (87)..(87)
<223> OTHER INFORMATION: Xaa may be substituted for an uncharged polar
residue, such as ser, asn or gln, an aliphatic residue such as
leu, or a basic residue, such as lys, arg or his
<220> FEATURE:
<221> NAME/KEY: VARIANT
<222> LOCATION: (92)..(93)
<223> OTHER INFORMATION: Xaa may be substituted for a different residue

<400> SEQUENCE: 14

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Glu Lys Gly Leu Val Tyr Met Ser Ile Cys Gly Glu Asn Glu Asn
        35                  40                  45

Cys Pro Pro Gly Val Gly Ala Cys Phe Gly Xaa Thr Arg Ile Ser Val
50                  55                  60

Gly Lys Ala Asn Lys Arg Leu Arg Tyr Val Asp Gln Val Leu Gln Leu
65                  70                  75                  80

Val Tyr Lys Asp Gly Ser Xaa Cys Pro Ser Lys Xaa Xaa Leu Ser Tyr
                85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 15
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (33)..(33)
<223> OTHER INFORMATION: Xaa may be substituted for a diffenret residue
gly, ala, val, leu or ile

<400> SEQUENCE: 15

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Xaa Glu Lys Gly Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
50                  55                  60

```
Gly Lys Ala Asn Lys Arg Leu Arg Tyr Val Asp Gln Val Leu Gln Leu
 65                  70                  75                  80

Val Tyr Lys Asp Gly Ser Pro Cys Pro Ser Lys Ser Gly Leu Ser Tyr
                 85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 16
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (34)..(34)
<223> OTHER INFORMATION: Xaa may be substituted for an aliphtic residue
      such as ala, val, leu or ile, a basic residue such as lys, arg or
      his, a sulphur containing residue such as cys or met, or a
      hydroxyl residue such as ser or thr

<400> SEQUENCE: 16

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
             20                  25                  30

Ser Xaa Lys Gly Leu Val Tyr Met Ser Ile Cys Gly Glu Asn Glu Asn
         35                  40                  45

Cys Pro Pro Gly Val Gly Ala Cys Phe Gly Gln Thr Arg Ile Ser Val
     50                  55                  60

Gly Lys Ala Asn Lys Arg Leu Arg Tyr Val Asp Gln Val Leu Gln Leu
 65                  70                  75                  80

Val Tyr Lys Asp Gly Ser Pro Cys Pro Ser Lys Ser Gly Leu Ser Tyr
                 85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
    130                 135                 140

<210> SEQ ID NO 17
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (35)..(35)
<223> OTHER INFORMATION: Xaa may be sustituted for a different residue,
      most preferably gly or ser

<400> SEQUENCE: 17

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
```

```
            20                  25                  30
Ser Glu Xaa Gly Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
 50                  55                  60

Gly Lys Ala Asn Lys Arg Leu Arg Tyr Val Asp Gln Val Leu Gln Leu
 65                  70                  75                  80

Val Tyr Lys Asp Gly Ser Pro Cys Pro Ser Lys Ser Gly Leu Ser Tyr
                 85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
        130                 135                 140

<210> SEQ ID NO 18
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (36)..(36)
<223> OTHER INFORMATION: Xaa may be substitute for a different residue,
      most preferably a hydrophobic residue, such as trp

<400> SEQUENCE: 18

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
                 20                  25                  30

Ser Glu Lys Xaa Leu Val Tyr Met Ser Ile Cys Gly Glu Asn Glu Asn
        35                  40                  45

Cys Pro Pro Gly Val Gly Ala Cys Phe Gly Gln Thr Arg Ile Ser Val
 50                  55                  60

Gly Lys Ala Asn Lys Arg Leu Arg Tyr Val Asp Gln Val Leu Gln Leu
 65                  70                  75                  80

Val Tyr Lys Asp Gly Ser Pro Cys Pro Ser Lys Ser Gly Leu Ser Tyr
                 85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
        130                 135                 140

<210> SEQ ID NO 19
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (37)..(37)
<223> OTHER INFORMATION: Xaa may be substitute for a different residue,
      most preferably an aliphatic residue, such as gly or val

<400> SEQUENCE: 19
```

-continued

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ser Glu Lys Gly Xaa Val Tyr Met Ser Ile Cys Gly Glu Asn Glu Asn
            35                  40                  45

Cys Pro Pro Gly Val Gly Ala Cys Phe Gly Gln Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Pro Cys Pro Ser Lys Ser Gly Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
            115                 120                 125

Ser Trp His Thr Pro Leu Ala Cys Glu Gln Ala Thr
    130                 135                 140

<210> SEQ ID NO 20
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 20

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr
            20                  25                  30

Ala Lys Gly Trp Gly Val Tyr Met Ser Ile Cys Gly Glu Asn Glu Asn
            35                  40                  45

Cys Pro Pro Gly Val Gly Ala Cys Phe Gly Gln Thr Arg Ile Ser Val
    50                  55                  60

Gly Lys Ala Asn Lys Arg Leu Arg Tyr Val Asp Gln Val Leu Gln Leu
65                  70                  75                  80

Val Tyr Lys Asp Gly Ser Pro Cys Pro Ser Lys Ser Gly Leu Ser Tyr
                85                  90                  95

Lys Ser Val Ile Ser Phe Val Cys Arg Pro Glu Ala Gly Pro Thr Asn
                100                 105                 110

Arg Pro Met Leu Ile Ser Leu Asp Lys Gln Thr Cys Thr Leu Phe Phe
            115                 120                 125

Ser Trp His Thr Pro Leu Ala Cys Glu Gln Ala Thr
    130                 135                 140

<210> SEQ ID NO 21
<211> LENGTH: 140
<212> TYPE: PRT
<213> ORGANISM: Artificial Sequence
<220> FEATURE:
<223> OTHER INFORMATION: Human IGF2R sequence variant

<400> SEQUENCE: 21

Asn Glu His Asp Asp Cys Gln Val Thr Asn Pro Ser Thr Gly His Leu
1               5                   10                  15

Phe Asp Leu Ser Ser Leu Ser Gly Arg Ala Gly Phe Thr Ala Ala Tyr

```
              20                  25                  30
Ser Lys Ser Gly Val Val Tyr Met Ser Ile Cys Gly Glu Asn Glu Asn
         35                  40                  45

Cys Pro Pro Gly Val Gly Ala Cys Phe Gly Gln Thr Arg Ile Ser Val
 50                  55                  60

Gly Lys Ala Asn Lys Arg Leu Arg Tyr Val Asp Gln Val Leu Gln Leu
 65                  70                  75                  80

Val Tyr Lys Asp Gly Ser Pro Cys Pro Ser Lys Ser Gly Leu Ser Tyr
             85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
        130                 135                 140

<210> SEQ ID NO 22
<211> LENGTH: 140
<212> TYPE: PRT
<213> ORGANISM: Artificial Sequence
<220> FEATURE:
<223> OTHER INFORMATION: Human IGF2R sequence variant
<220> FEATURE:
<221> NAME/KEY: VARIANT
<222> LOCATION: (33)..(37)
<223> OTHER INFORMATION: Xaa can be any amino acid
<220> FEATURE:
<221> NAME/KEY: VARIANT
<222> LOCATION: (59)..(59)
<223> OTHER INFORMATION: Xaa can be any amino acid
<220> FEATURE:
<221> NAME/KEY: VARIANT
<222> LOCATION: (87)..(87)
<223> OTHER INFORMATION: Xaa can be any amino acid
<220> FEATURE:
<221> NAME/KEY: VARIANT
<222> LOCATION: (92)..(93)
<223> OTHER INFORMATION: Xaa can be any amino acid

<400> SEQUENCE: 22

Asn Glu His Asp Asp Cys Gln Val Thr Asn Pro Ser Thr Gly His Leu
 1               5                  10                  15

Phe Asp Leu Ser Ser Leu Ser Gly Arg Ala Gly Phe Thr Ala Ala Tyr
             20                  25                  30

Xaa Xaa Xaa Xaa Xaa Val Tyr Met Ser Ile Cys Gly Glu Asn Glu Asn
         35                  40                  45

Cys Pro Pro Gly Val Gly Ala Cys Phe Gly Xaa Thr Arg Ile Ser Val
 50                  55                  60

Gly Lys Ala Asn Lys Arg Leu Arg Tyr Val Asp Gln Val Leu Gln Leu
 65                  70                  75                  80

Val Tyr Lys Asp Gly Ser Xaa Cys Pro Ser Lys Xaa Xaa Leu Ser Tyr
             85                  90                  95

Lys Ser Val Ile Ser Phe Val Cys Arg Pro Glu Ala Gly Pro Thr Asn
            100                 105                 110

Arg Pro Met Leu Ile Ser Leu Asp Lys Gln Thr Cys Thr Leu Phe Phe
        115                 120                 125

Ser Trp His Thr Pro Leu Ala Cys Glu Gln Ala Thr
        130                 135                 140
```